US010166280B2

(12) United States Patent
Tam et al.

(10) Patent No.: US 10,166,280 B2
(45) Date of Patent: Jan. 1, 2019

(54) POLYPEPTIDES AND IMMUNIZING COMPOSITIONS CONTAINING *BACILLUS* POLYPEPTIDES AND METHODS OF USE

(71) Applicant: EPITOPIX LLC, Willmar, MN (US)

(72) Inventors: Patricia E. Tam, Golden Valley, MN (US); Michael Nathan Harris, Los Alamos, NM (US); Timothy James Tripp, Eden Prairie, MN (US); Sandra Lobo, Sandy Hook, CT (US)

(73) Assignee: EPITOPIX, LLC, Willmar, MN (US)

( * ) Notice: Subject to any disclaimer, the term of this patent is extended or adjusted under 35 U.S.C. 154(b) by 0 days.

(21) Appl. No.: 15/617,541

(22) Filed: Jun. 8, 2017

(65) Prior Publication Data

US 2018/0064799 A1 Mar. 8, 2018

Related U.S. Application Data

(60) Provisional application No. 62/347,454, filed on Jun. 8, 2016.

(51) Int. Cl.
*C07K 1/00* (2006.01)
*A61K 39/07* (2006.01)
*C07K 14/32* (2006.01)
*A61K 39/00* (2006.01)

(52) U.S. Cl.
CPC .............. *A61K 39/07* (2013.01); *C07K 14/32* (2013.01); *A61K 2039/55561* (2013.01); *A61K 2039/55566* (2013.01); *A61K 2039/57* (2013.01); *A61K 2039/70* (2013.01)

(58) Field of Classification Search
CPC .................................................. A61K 39/07
See application file for complete search history.

(56) References Cited

U.S. PATENT DOCUMENTS

| 4,167,560 A | 9/1979 | Wohler, Jr. |
| 4,452,775 A | 6/1984 | Kent |
| 4,626,416 A | 12/1986 | De Voe |
| 4,663,161 A | 5/1987 | Mannino |
| 4,681,761 A | 7/1987 | Mietzner |
| 4,748,018 A | 5/1988 | Stolle |
| 4,871,488 A | 10/1989 | Mannino |
| 4,981,685 A | 1/1991 | Healey |
| 5,141,743 A | 8/1992 | Schryvers |
| 5,292,869 A | 3/1994 | Schryvers |
| 5,439,808 A | 8/1995 | Blake |
| 5,534,256 A | 7/1996 | Potter |
| 5,538,733 A | 7/1996 | Emery |
| 5,554,372 A | 9/1996 | Hunter |
| 5,587,166 A | 12/1996 | Donachie |
| 5,688,682 A | 11/1997 | Mulks |
| 5,830,479 A | 11/1998 | Emery |
| 5,885,589 A | 3/1999 | Foged |
| 5,906,826 A | 5/1999 | Emery |
| 6,027,736 A | 2/2000 | Emery |
| 6,348,198 B1 | 2/2002 | Schryvers et al. |
| 6,432,412 B1 | 8/2002 | Emery |
| 6,682,754 B2 | 1/2004 | Emery |
| 6,692,739 B1 | 2/2004 | Patti |
| 6,720,160 B2 | 4/2004 | Wolde-Mariam |
| 6,869,607 B1 | 3/2005 | Buschle |
| 6,984,503 B1 | 1/2006 | Wang |
| 7,026,157 B1 | 4/2006 | Stojiljkovic |
| 7,138,124 B2 | 11/2006 | Emery |
| 7,138,125 B2 | 11/2006 | Emery |
| 7,147,857 B2 | 12/2006 | Emery |
| 7,148,191 B2 | 12/2006 | Egyed |
| 7,153,527 B2 | 12/2006 | Gradle |
| 7,160,549 B2 | 1/2007 | Emery |
| 7,341,732 B2 | 3/2008 | Emery |
| 7,371,393 B2 | 5/2008 | Emery |
| 7,413,743 B2 | 8/2008 | Emery |
| 7,943,150 B2 | 5/2011 | Emery |
| 7,943,151 B2 | 5/2011 | Emery |
| 8,007,803 B2 | 8/2011 | Emery |
| 8,007,811 B2 | 8/2011 | Emery |
| 8,025,885 B2 | 9/2011 | Emery |
| 8,119,147 B2 | 2/2012 | Emery |
| 8,282,941 B2 | 10/2012 | Emery |
| 8,329,192 B2 | 12/2012 | Straub |
| 8,425,916 B2 | 4/2013 | Emery |
| 8,575,315 B2 | 11/2013 | Emery |
| 8,637,048 B2 | 1/2014 | Emery |
| 8,709,760 B2 | 4/2014 | Emery |
| 8,961,979 B2 | 2/2015 | Emery |
| 8,993,252 B2 | 3/2015 | Emery |

(Continued)

FOREIGN PATENT DOCUMENTS

| AU | 2002239820 | 12/2007 |
| BR | PI0206293-3 | 1/2015 |

(Continued)

OTHER PUBLICATIONS

U.S. Appl. No. 12/272,021, filed Nov. 17, 2008, Emery.
U.S. Appl. No. 13/362,894, filed Jan. 31, 2012, Emery.
U.S. Appl. No. 13/362,992, filed Jan. 31, 2012, Emery.
Acheson, "Protective Immunity to Shiga-Like Toxin I Following Oral Immunization with Shiga-Like Toxin I B-Subunit-Producing *Vibrio cholerae* CVD 103-HgR," *Infect. Immun.*, Jan. 1996;64(1):355-357.
Alberti, "A porin from *Klebsiella pneumoniae*: sequence homology, threedimensional model, and complement binding," Mar. 1995 *Infect Immun.*, 63(3): 903-910.
Alurkar, "Immunomodulatory Properties of Porins of Some Members of the family *Enterobacteriaceae*, "*Infection and Immunity*, Jun. 1997; 65(6):2382-2388.

(Continued)

*Primary Examiner* — Albert M Navarro
(74) *Attorney, Agent, or Firm* — Mueting, Raasch & Gebhardt, PA

(57) ABSTRACT

The present invention provides isolated polypeptides isolatable from a *Bacillus* spp. Also provided by the present invention are compositions that include one or more of the polypeptides, and methods for making and methods for using the polypeptides.

6 Claims, 8 Drawing Sheets

Specification includes a Sequence Listing.

(56) References Cited

U.S. PATENT DOCUMENTS

| | | |
|---|---|---|
| 9,085,613 B2 | 7/2015 | Emery |
| 9,463,230 B2 | 10/2016 | Emery |
| 2002/0061569 A1 | 5/2002 | Haselbeck |
| 2003/0036639 A1 | 2/2003 | Emery |
| 2003/0064073 A1 | 4/2003 | Emery |
| 2003/0206922 A1 | 11/2003 | Emery |
| 2003/0211118 A1 | 11/2003 | Emery |
| 2004/0197350 A1 | 10/2004 | Emery |
| 2004/0197869 A1 | 10/2004 | Emery |
| 2004/0265329 A1 | 12/2004 | Emery |
| 2005/0037444 A1 | 2/2005 | Meinke |
| 2005/0186217 A1 | 5/2005 | Emery |
| 2005/0095682 A1 | 8/2005 | Emery |
| 2006/0024323 A1 | 2/2006 | Emery |
| 2006/0083753 A1 | 4/2006 | Emery |
| 2006/0165718 A1 | 7/2006 | Emery |
| 2006/0233824 A1 | 10/2006 | Emery |
| 2006/0269564 A1 | 11/2006 | Emery |
| 2007/0087011 A1 | 4/2007 | Emery |
| 2007/0098733 A1 | 5/2007 | Emery |
| 2008/0200650 A1 | 8/2008 | Emery |
| 2008/0293080 A1 | 11/2008 | Emery |
| 2009/0081236 A1 | 3/2009 | Emery |
| 2009/0123500 A1 | 5/2009 | Emery |
| 2009/0162402 A1 | 6/2009 | Emery |
| 2010/0111903 A1 | 5/2010 | Emery |
| 2010/0221253 A1 | 9/2010 | Emery |
| 2011/0200616 A1 | 8/2011 | Emery |
| 2011/0200637 A1 | 8/2011 | Emery |
| 2011/0206733 A1 | 8/2011 | Emery |
| 2012/0003269 A1 | 1/2012 | Emery |
| 2012/0195898 A1 | 8/2012 | Emery |
| 2012/0195899 A1 | 8/2012 | Emery |
| 2013/0217048 A1 | 8/2013 | Emery |
| 2017/0087238 A1 | 3/2017 | Emery |

FOREIGN PATENT DOCUMENTS

| | | | |
|---|---|---|---|
| CA | 2029906 | | 9/1990 |
| CA | 2433561 | | 4/2014 |
| CA | 2708949 | | 3/2016 |
| EP | 0287206 A1 | | 10/1988 |
| EP | 0287206 B1 | | 10/1988 |
| EP | 0287206 B2 | | 10/1988 |
| EP | 1353689 B9 | | 5/2006 |
| WO | WO 90/11349 A1 | | 10/1990 |
| WO | WO 90/12591 A1 | | 11/1990 |
| WO | WO 95/21627 A1 | | 8/1995 |
| WO | WO 96/01620 A1 | | 1/1996 |
| WO | WO 01/37810 A2 | | 5/2002 |
| WO | WO 02/053180 A2 | | 7/2002 |
| WO | WO 02/059148 A9 | | 10/2002 |
| WO | WO-02077183 A2 * | 10/2002 | ........... C07K 14/195 |
| WO | WO 17/011340 A2 | | 1/2017 |

OTHER PUBLICATIONS

Ames, "Resolution of bacterial proteins by polyacrylamide gel electrophoresis on slabs. Membrane, soluble, and periplasmic fractions," Jan. 1974 *J Biol Chem.*, 249(2):634-644. (No abstract available.).

Anwar, "Antibody response to acute *Pseudomonas aeruginosa* infection in a burn wound," *FEMS Microbiology Letters*, 1985; 29:225-230.

Arockiasamy, "Purification of Integral Outer-Membrane Protein OmpC, a Surface Antigen from *Salmonella typhi* for Structure-Function Studies: A Method Applicable to Enterobacterial Major Outer-Membrane Protein," *Analytical Biochemistry*, 2000, 283:64-70.

Arp, "Response of turkeys to *Escherichia coli*," 1994 *Poultry Digest*, 142, 146.

Ashkenazi, "Safety and Immunogenicity of Shigella Sonnei and Shigella Flexneri 2a 0-specific Polysaccharide Conjugates in Children," Jun. 1999 *J Infect. Dis.*, 179(6): 1565-1568.

Ausubel, eds., *Current Protocols in Molecular Biology*, John Wiley & Sons, Inc., 1998; cover pg., publication pg., and table of contents only (12 pgs.).

Babu, "Effects of Live Attenuated and Killed *Salmonella* Vaccine on TLymphocyte Mediated Immunity in Laying Hens," *Vet. Immunol. Immunopathol.*, Jan. 10, 2003;91(1):39-44.

Banerjee-Bhatnagar, "Expression ofNeisseria meningitidis iron-regulated outer membrane proteins, including a 70-kilodalton transferrin receptor, and their potential for use as vaccines," Sep. 1990 *Infect Immun.*, 58(9):2875-2881.

Bannerman, "The bovine innate immune response during experimentally induced *Pseudomonas aeruginosa* mastitis," *Vet. Immunopathol.*, 2005, 107:201-215.

Baumler, "IroN, a Novel Outer Membrane Siderophore Receptor Characteristic of *Salmonella enterica*" Mar. 1998 *Journal of Bacteriology*, 180(6):1446-1453.

Blaser, "*Campylobacter jejuni* Outer Membrane Proteins are Antigenic for Humans" *Infection and Immunity*, Mar. 1984; 43(3):986-993.

Bokete, "Genetic and Phenotypic Analysis of *Escherichia coli* with Enteropathogenic Characteristics Isolated from Seattle Children," Jun. 1997 *J. Infect. Dis.*, 175(6):1382-1389.

Bolin, "Passive Immunization with Antibodies Against Iron-Regulated Outer Membrane Proteins Protects Turkeys from *Escherichia coli* Septicemia," *Infect Immun.*, May 1987;55(5):1239-1242.

Boothby, "Characterization of antigens from mycoplasmas of animal origin," *Am J Vet Res.* Mar. 1983; 44(3):433-439.

Bos, "Biogenesis of the gram-negative bacterial outer membrane" 2004 *Current Opinion in Microbiology*, 7:610-616.

Bosworth, "Vaccination with Genetically Modified Shiga-Like Toxin IIe Prevents Edema Disease in Swine," *Infect. Immun.*, Jan. 1996;64(1):55-60.

Bouchet, "Immunological variants of the aerobactin-cloacin DF13 outer membrane protein receptor IutA among enteric bacteria," *Infect Immun.* Jul. 1994; 62(7):3017-3021.

Boulianne, "Production of functional chimaeric mouse/human antibody" 1984 *Nature*, 312(5995):643-646.

Bradley, "Bovine Mastitis: An Evolving Disease," 2002 *Vet. Journal*, 164/2:116-128.

Bragg, "Organization of proteins in the native and reformed outer membrane of *Escherichia coli*," *Biochim Biophys Acta.* Aug. 9, 1972;274(2):478-488. (No abstract available.).

Brogden, "Lysates of turkey-grown Pasteurella multocida: effects of solubilizing agents on the immunologic properties of membrane vesicles," Mar. 1983 *Am J Vet Res.*, 44(3):428-432.

Bruckmaier, "Changes of physiochemical indicators during mastitis and the effects of milk ejection on their sensitivity," 2004 *J. Dairy Res.*, 2004, 71/3:316-321 (abstract only).

Bruckmaier,"Immunomediator and milk protein gene expression in mammary tissue during endotoxin-induced mastitis," *Livestock Production Science*, 2005; 98(1/2):81-87, abstract only (1 pg).

Bruggeman, "Production of human antibody repertoires in transgenic mice" 1997 Curr. Opin. Biotechnol., 8(4):455-458.

Burvenich, "Severity of *E. coli* mastitis is mainly determined by cow factors," 2003 *Vet. Res.*, 34:521-564.

Butterton, "Coexpression of the B Subunit of Shiga Toxin 1 and EaeA from Enterohemorrhagic *Escherichia coli* in *Vibrio cholerae* Vaccine Strains," Jun. 1997 *Infect. Immun.*, 65(6):2127-2135.

Callaway, "Fecal prevalence and diversity of *Salmonella* species in lactating dairy cattle in four states" 2005 *J. Dairy Science*, 88(10): 3603-3608.

Calnek, Diseases of Poultry-9th ed., pp. 99-130, Iowa State University, Ames Iowa (1991).

CDC *Salmonella* Surveillance: Annual Summary, 2002. Atlanta, GA: US Department of Health and Human Services, CDC, 2003.

CDC *Shigella* Surveillance: Annual Summary, 2002. Atlanta, GA: US Department of Health and Human Services, CDC, 2003.

Charles, "Adjuvanted Subunit Vaccines for the Control of *Salmonella enteritidis* Infection in Turkeys," May 1994 *Am. J. Vet. Res.*, 55(5):636-642.

(56) References Cited

OTHER PUBLICATIONS

Chart, "Antigenic and Molecular Homology of the Ferric Enterobactin Receptor Protein of *Eschericia coli*," Jun. 1985 *J. Gen. Microbial.*, J31(6):1503-1509.

Chart, "Iron-regulated Outer-membrane Proteins of *Eschericia coli* Strains Associated with Enteric or Extraintestinal Diseases of Man and Animals," Jun. 1988 *J. Gen. Microbio.*, 134(6):1549-1559.

Choi-Kim, "Relationship between the iron regulated outer membrane proteins and the outer membrane proteins of in vivo grown Pasteurella multocida," Jun. 1991 *Vet Microbial.*, 28(1):75-92.

Chou, "Effect of Ferrous Sulfate, Sodium Metabisulfite, and Sodium Pyruvate on Survival of *Campylobacterjejuni*," Journal of Clinical Microbiology, Oct. 1983, 18(4): 986-987.

CMPT Mycology Plus, 0709-3 "Fusarium species", pp. 1-2, Sep. 2007.

Cohen, "Double-Blind Vaccine-Controlled Randomised Efficacy Trial of an Investigational *Shigella* Sonnei Conjugate Vaccine in Young Adults," Jan. 1997 *Lancet*, 18;349(9046):155-159.

Corbett, "Effect of Iron Deprivation on Outer Membrane Proteins of Pasteurella multocida," Abstract, published in the Abstracts of the 85th Annual Meeting of the American Society for Microbiology, Las Vegas, Nevada, Mar. 3-7, 1985 (13 pgs).

Coster, "Vaccination Against Shigellosis with Attenuated *Shigellaflexneri* 2a Strain SC602," Jul. 1999 *Infect. Immun.*, 67(7):3437-3443.

Coulton, "Protein II influences ferrichrome-iron transport in *Escherichia coli* K12," Jan. 1979 *J GenMicrobiol.*,JJ0(1):211-220.

Courcol, "Siderophore production by *Staphylococcus aureus* and identification of iron-regulated proteins," May 1997 *Infect. Immun.*, 65(5):1944-1948.

Crichton, "Chapter 3. Microbial iron uptake and intracellular release" In: *Inorganic Biochemistry of Iron Metabolism*, Burgess, (ed)., 1991, Ellis Horwood Limited, Chichester, England, Title page and pp. 59-76.

Crist,*Mastits and its Control*, [online]. University of Kentucky, College of Agriculture. [retrieved on Jul. 15, 2002]. Retrieved from the Internet: <URL:http://www.ca.uky.edu/agc/pubs/asc/asc140/asc140.htm>; 22 pgs.

Crosa, "The relationship of plasmid-mediated iron transport and bacterial virulence," *Annu Rev Microbial.* 1984;38:69-89. Review. (No abstract available.).

Crosa, "Genetics and Molecular Biology of Siderophore-Mediated Iron Transport in Bacteria," *Microbial. Rev.*, Dec. 1989; 53(4):517-530.

Curtiss, "Live Oral Avirulent *Salmonella* Vaccines," Nov. 1993 *Vet. Microbial.*, 37(3-4):397-405.

Danve, "Transferrin-binding proteins isolated from Neisseria meningitidis elicit protective and bactericidal antibodies in laboratory animals," Sep. 1993 *Vaccine*, 11(12):1214-1220.

Daugherty, "Polymerase chain reaction facilitates the cloning, CDRgrafting, and rapid expression of a murine monoclonal antibody directed against the CD18 component of leukocyte integrins" Mar. 1991 *Nucleic Acids Res.*, 19(9): 2471-2476.

Davies, "Characterisation of bovine strains of *Pasteurella multocida* and comparison with isolates of avian, ovine and porcine origin," 2004 *Vet. Microbiology*, 99:145-158.

Davison, "Field Observations with *Salmonella enteritidis* Bacterins," Oct.-Dec. 1999 *Avian Dis.*, 43(4):664-669.

Dziaba, "An Attempt to Immunize Pigs Against Colibacteriosis Under Field Conditions," 1984 *Medycyna Weterynaryjna*, 40(8):455-457 (English abstract on p. 457).

El-Shobaki, "Mucosal transferrin and ferritin factors in the regulation of iron absorption," Dec. 1977 *Res Exp Med (Berl).*, 171(3):243-253.

Erdei, "Lactoferrin binds to porins OmpF and OmpC in *Escherichia coli*," Apr. 1994 *Infection and Immunity*, 62(4):1236-1240.

E-TOXATE® (Technical Bulletin No. 210). SIGMA Chemical Company, St. Louis, MO, 1998. pp. 1-4.

"Explanation of the HMIS® Ratings" [online], American Coatings Association, Washington, DC, [retrieved on Oct. 4, 2012], retrieved from the Internet: <URL:http://www.paint.org/component/docman/cat_view/49-hmis.html>, 2 pgs.

Fabian, "Heme transfer to the bacterial cell envelope occurs via a secreted hemophore in the Gram-positive pathogen Bacillus anthracis" 2009 *J Biol Chem.*, 284:32138-32146.

Feng, "P55, an immunogenic but nonprotective 55-kilodalton Borrelia burgdorferi protein in murine Lyme disease," Jan. 1996 *Infect Immun.*, 64(1):363-365.

Ferguson, "Siderophore-mediated iron transport: crystal structure of FhuA with bound lipopolysaccharide," *Science.* Dec. 18, 1998;282(5397):2215-2220.

Field, "Influence of Iron on Growth, Morphology, Outer Membrane Protein Composition, and Synthesis of Siderophores in *Campylobacterjejuni*" Oct. 1986 *Infect. Immun.*, 54(1):126-132.

Filip, "Solubilization of the cytoplasmic membrane of *Escherichia coli* by the ionic detergent sodium-lauryl sarcosinate," Sep. 1973 *JBacteriol.*, ll5(3):717-722.

Finkelstein, "Role of iron in microbe-host interactions," *Rev Infect Dis.* Sep.-Oct. 1983;5 Suppl 4: S759-776.

Francis, "Immunological priming with synthetic peptides of foot-and-mouth disease virus," Nov. 1985 *J Gen Virol.*, 66 (Pt 11):2347-2354.

Fukutome, "Intestinal Mucosa!Immune Response in Chickens Following Intraocular Immunization with Liposome-Associated *Salmonella enterica* Serovar Enteritidis Antigen," *Dev. Comp. Immunol.*, 2001 Jun.-Jul.;25(5-6):475-484.

Furugouri, "Iron binding substances in the intestinal mucosa of neonatal piglets," *J Nutr.* Mar. 1977; 107(3):487-494.

Gast, "Deposition of Phage Type 4 and 13a *Salmonella enteritidis* Strains in the Yolk and Albumen of Eggs Laid by Experimentally Infected Hens," *Avian Dis.*, Jul.-Sep. 2000;44(3):706-710.

Germanier, "Isolation and Characterization of *Gal E* Mutant Ty 21a of *Salmonella typhi*: A Candidate Strain for a Live, Oral Typhoid Vaccine," May 1975 *J Infect. Dis.*, 131(5):553-558.

Gilleland, Jr., "Use of a purified outer membrane protein F (porin) preparation of Pseudomonas aeruginosa as a protective vaccine in mice," *Infect Immun.* Apr. 1984; 44(1):49-54.

Gilleland, Jr., "Perspectives on the potential for successful development of outer membrane protein vaccines," *Eur J ClinMicrobial.* Jun. 1987; 6(3): 231-233. Review. (No abstract available.).

Gilmour, "Vaccine containing iron-regulated proteins of Pasteurella haemolytica A2 enhances protection against experimental pasteurellosis in lambs," Feb. 1991 *Vaccine*, 9(2):137-140.

Glisson, "In vivo antigen expression by Pasteurella multocida," Apr.-Jun. 1991 *Avian Dis.*, 35(2):392-396.

Glisson, "Cross-Protection Studies with Pasteurella multocida Bacterins Prepared from Bacteria propagated in Iron-Depleted Medium," Oct.-Dec. 1993 *Avian Dis.*, 37(4):1074-1079.

Goding, "*Monoclonal Antibodies: Principles and Practice*," Academic Press, 162-165 (1986).

Greenbaum, 2007 *Molecular Recognition*, 20/2:75-82.

Greenspan, 1999 *Nature Biotechnology*, 17:936•937.

Griffiths, "Naturally occurring antibodies in human sera that react with the iron-regulated outer membrane proteins of *Escherichia coli*," Mar. 1985 *Infect Immun.*, 47(3):808-813.

Griffiths, "Pathogenic *Escherichia coli* express new outer membrane proteins when growing in vivo," 1983 *FEMS Microbiology Letters*, 16:95-99.

Gruet, "Bovine mastits and intramammary drug delivery: review and perspectives," 2001 *Advanced Drug Delivery Reviews*, 50:245-259.

Haddadi, "*E. coli* proteolytic activity in milk and casein breakdown," 2005 *Reprod Nutr. Dev.*, 45:485-496 (abstract only).

Hancock, "Iron transport in *Escherichia coli* K-12: involvement of the colicin B receptor and of a citrate-inducible protein," *J. of Bacterial.*, 127(3):1370-1375 (1976).

Harlow, "*Antibodies: A Laboratory Manual*," Cold Spring Harbor Laboratory, 689 (1988).

Hassan, "Development and Evaluation of an Experimental Vaccination Program Using a Live Avirulent *Salmonella typhimurium* Strain to Protect Immunized Chickens Against Challenge with

(56) References Cited

OTHER PUBLICATIONS

Homologous and Heterologous *Salmonella* Serotypes," Dec. 1994 *Infect. Immun.*, 62(12):5519-5527.
Heinrichs, "Identification and characterization of SirA, an iron-regulated protein from *Staphylococcus aureus*," *J. Bacteriol.* Mar. 1999; 181( 5):1436-1443.
Helenius, "Solubilization of membranes by detergents," Nar 1975 *Biochim Biophys Acta.*, 415( 1):29-79. Review.
Herbert, Dictionary of Immunology, 4th Editin. Academic Press, 1995, pp. 58-59.
Hermans, "Poultry as a host for the zoonotic pathogen *Campylobacter jejuni*" 2012 *Vector Borne Zoonotic Dis.*, 12:2, 89-98.
Hirst, "Iron-regulated outer membrane proteins of *Aeromonas salmonicida* are important protective antigens in Atlantic salmon against furunculosis, "*Fish & Shellfish Immunology*, 1994; 4:29-45.
Hjelmeland, Solubilization of native membrane proteins, *Methods Enzymol.* 1990; 182:253-264.
Hohmarm, "phoP/phoQ-Deleted *Salmonella typhi* (Ty800) is a Safe and Immunogenic Single-Dose Typhoid Fever Vaccine in Volunteers," Jun. 1996 *J. Infect. Dis.*,173(6):1408-1414.
Hope, "An Overview of the *Salmonella enteritidis* Risk Assessment for Shell Eggs and Egg Products," Apr. 2002 *Risk Anal.*, 22(2):203-218.
House, "Evaluation of an autogenous *Salmonella* bacterin and a modified live *Salmonella* serotype Choleraesuis vaccine on a commercial dairy farm," *Am J Vet Res.* Dec. 2001;62(12):1897-1902.
Hudson, "Lymphokines and Cytokines," In: *Practical Immunology*, Oxford, Blackwell Scientific Publications, London, UK, 1989, 3rd Edition, 423-441.
Humphrey, "Contamination of Egg Shell and Contents with *Salmonella enteritidis*: aReview," Jan. 1994 *Int. J. Food Microbial.*, 21(1-2):31-40.
Hussain, "A Lithium Chloride-Extracted, Broad-Spectrum-Adhesive 42-Kilodalton Protein of *Staphylococcus epidermidis* is Omithine Carbamoyltransferase," [online] Dec. 1999 *Infection and Immunity*, 7(12):6688-6690. [retrieved on Jul. 12, 2002]. Retrieved from the Internet: <URL:http://iai.asm.org/cgi/content/full/67112/6688?view=full&pmid=10569792>. 8 pgs.
Ikeda, "Antigenically Related Iron-Regulated Outer Membrane Proteins Produced by Different Somatic Serotypes of Pasteurella Multocida," *Irifect. Immun.*, Sep. 1988; 56(9):2499-2502.
Jiang, "Ligand-Specific Opening of a Gated-Porin Channel in the Outer Membrane of Living Bacteria," *Science*, May 1997, 276:1261-1264.
Johansen, "Prevention of Edema Disease in Pigs by Vaccination with Verotoxin 2e Toxoid," *Can. J. Vet. Res.*, 1997; 61:280-285.
Jones, "Replacing the complementarity-determining regions in a human antibody with those from a mouse" 1986, *Nature* 321(6069):522-525.
Jousimies, "Genetic Analysis of *Salmonella minnesota* R mutants with defects in the biosynthesis of the Lipopolysaccharide core," Sep. 1974*J Bacteriol.*, 119(3):753-759.
Keler, "Metachromatic Assay for the Quantitative Determination of Bacterial Endotoxins," 1986 *Analyt. Biochem.*, 156:189-193.
Khan, "Reducing Colonization of *Salmonella enteritidis* in Chicken by Targeting Outer Membrane Proteins," 2003 *J. Appl. Microbial.*, 95(1):142-145.
Kizil, "Identification and Characterization of TspA, a Major CD4+ T-Cell- and B-Cell-Stimulating *Neisseria-Specific* Antigen," [online]. [retrieved on Jul. 15, 2002]. Retrieved from the Internet: <URL:http://iai.asm.org/ cgi/content/full/671713533?maxtoshow=&HITS=1O&hits=1O&RESULTFORMAT=&searchid=1026752040493_2258&stored_search=&FIRSTINDEX=O&volume=67&firstpage=3533&joumalcode=iai>. 19 pgs.
Klebba, "Kinetics of biosynthesis of iron-regulated membrane proteins in *Escherichia coli*," Mar. 1982 *J Bacteriol.*, 149(3):880-888.
Koebnik, "Structure and function of bacterial outer membrane proteins: barrels ina nutshell," *Molecular Microbiology*, 2000, 37/2:239-253.

Kohler, "Continuous cultures of fused cells secreting antibody of predefined specificity," Aug. 1975 *Nature*, 256 (5517):495-497.
Konadu, "Preparation, Characterization, and Immunological Properties in Mice of *Escherichia coli* 0157 0-Specific Polysaccharide-Protein Conjugate Vaccines," Nov. 1994 *Infect. Immun.*, 62(11):5048-5054.
Kotloff, "Safety, Immunogenicity, and Transmissibility in Humans of CVD 1203, a Live Oral *Shigella flexneri* 2a Vaccine Candidate Attenuated by Deletions in aroA and virG, "Nov. 1996 *Infect. Immun.*, 64(11):4542-4548.
Laemmli, "Cleavage of structural proteins during the assembly of the head of bacteriophage T4," Aug. 1970 *Nature*, 227(259):680-685.
Lainson, "Identification and localization of an iron-regulated 35 kDa protein of Pasteurella haemolytica serotype A2," Feb. 1991 *J Gen. Microbio.*,., 137(2): 219-226.
Lalmanach, "Host Cytokine Response and Resistance to *Salmonella* Infection," Jul. 1999*Microbes Infect.*, 1(9):719-726.
Lau, "Protein secretion and lipopolysaccharide assembly in *Escherichia coli*" 2008 *Dissertation Abstracts International*, 68:12B.
Lee, "Elevated Milk Soluble CD14 in Bovine Mammary Glands Challenged with *Escherichia coli* Lipopolysaccharide," 2003 *J Dairy Science*, 86:2382-2389.
Lefcourt, "Method to Monitor the Precision of Milk Yields Recorded at Individual Milking Stalls on a Daily Basis," 1999 *J. Dairy Sci.*, 82:953-956.
Leitner, "Development of a *Staphylococcus aureus* Vaccine Against Mastitis in Dairy Cows. II. Field Trial," *Veterinary Immunology and Immunopathology*, 2003;93:153-158.
Li, "Standardized, mathematical model-based and validated in vitro analysis of anthrax lethal toxin neutralization" 2008 *J Imm Meth.*, 333:89-106.
Lindsay, "*Staphylococcus aureus* but not *Staphylococcus epidermidis* can acquire iron from transferrin," *Microbiology*, 1995; 141:197-203.
Lindsay, "Staphylococcal iron requirements, siderophore production, and iron-regulated protein expression," *Infect. Immun.*, Jun. 1994; 62(6):2309-2314.
Lobuglio, "Mouse/human chimeric monoclonal antibody in man: kinetics and immune response" 1989, *Proc. Natl. Acad. Sci. USA* 86(11):4220-4224.
Lonberg, "Antigen-specific human antibodies from mice comprising four distinct genetic modifications" Apr. 1994 *Nature*, 368:856-859.
Lonberg, "Human antibodies from transgenic mic" 1995 *Int. Rev. Immunol.*, 13(1):65-93.
Lu, "A monoclonal antibody against a Pasteurella multocida outer membrane protein protects rabbits and mice against pasteurellosis," Jan. 1991 *Infect Immun.*, 59(1):172-180.
Lu, "The outer membrane of Pasteurella multocida 3:A protects rabbits against homologous challenge," Dec. 1991 *Infect Immun.*, 59(12):4517-4523.
Lubke, "Isolation and partial characterization of the major protein of the outer membrane of Pasteurella haemolytica and Pasteurella multocida," *Zentralbl Bakteriol.* Jun. 1994;281(1):45-54.
Lucier, "Iron uptake and iron-repressible polypeptides in Yersinia pestis" Aug. 1996 *Infect. Immun.* 64: 3023-3031.
Luderitz, "Lipopolysaccharides, the O antigens and endotoxins of gram-negative bacteria: Relationships of chemical structure and biological activity," *The Virulence of Escherichia coli*, Sussman, ed., The Society for General Microbiology, Academic Press, 73-88 (1985).
Lumsden, "Resistance to fecal shedding of salmonellae in pigs and chickens vaccinated with an aromatic-dependent mutant of *Salmonella typhimurium,*" *Am J VetRes.* Nov. 1991;52(11):1784-1787.
MacFarlane, "Two dimensional benzyldimethyl-n-hexadecylammonium chloride-sodium dodecyl sulfate preparative polyacrylamide gel electrophoresis: a high capacity high resolution technique for the purification of proteins from complex mixtures" 1989, *Anal Biochem.*, 176:457-463.
Makela, "Participation of lipopolysaccharide genes in the determination of the enterobacterial common antigen: analysis of R mutants of *Salmonella minnesota*," Sep. 1974 *J Bacteriol.*, 119(3):760-764.

(56) References Cited

OTHER PUBLICATIONS

Maniatis,*Molecular cloning: A Laboratory Manual*, Cold Spring Harbor Lab., New York, 1982, Cover pg., Publication pg., and Table of Contents only (8 pgs.).
Manspeaker, "Metritis and Endometritis," [online]. *Northeast !RM Manual*. [retrieved on Jan. 25, 2005]. Retrieved from the Internet: <URL:http://www.wvu.edu/exten/infores/pubs/livepoul/dirm22.pdf.>. 4 pgs.
Maresso, "Bacillus anthracis Secretes Proteins That Mediate Heme Acquisition from Hemoglobin" Aug. 2008 PLoS Pathog., 4:e1000132.
Material Safety Data Sheet 2,2'-Bipyridine MSDS, Sciencelab.com, Inc., Houston, TX, created Oct. 9, 2005, last updated Jun. 9, 2012, pp. 1-5.
Material Safety Data Sheet—Deferoxamine Mesylate, Sigma-Aldrich, St. Louis, MO, Version 1.2, updated Apr. 8, 2004, printed Nov. 8, 2005, pp. 1-5.
Matsui, "Specificity of protective immunity induced by porin from *Salmonella typhimurium*," 1991 *Microbiologica*, 14:103-112.
Matthews-Greer, "Outer membrane protein F (porin) preparation of Pseudomonas aeruginosa as a protective vaccine against heterologous immunotype strains in a burned mouse model," Jun. 1987 *JInfect Dis.*, 155(6): 1282-1291.
Mazurier, "Visualization oflactotransferrin brush-border receptors by ligand-blotting," Dec. 1985 *Biochim Biophys Acta.*, 19;821(3):453-460.
Mead, "Food-Related Illness and Death in the United States," Sep.-Oct. 1999 *Emerg. Infect. Dis.*, 5(5):607-625.
Medearis, Jr., "Cell wall composition and virulence in *Escherichia coli,*" *JExp Med*. Sep. 1, 1968; 128(3):399-414.
Meenakshi, "Adjuvanted Outer Membrane Protein Vaccine Protects Poultry Against Infection with *Salmonella enteritidis*," Mar. 1999 *Vet. Res. Commun.*, 23 (2): 81-90.
Merrifield, "Solid Phase Peptide Synthesis. I. The Synthesis of a Tetrapeptide," Jul. 1963 *J Am. Chem. Soc.*, 85(14):2149-2154.
Modun, "The *Staphylococcus aureus* and *Staphylococcus epidermidis* transferrin-binding proteins are expressed in vivo during infection," *Microbiology*, 1998;144:1005-1012.
Morrison, "Chimeric human antibody molecules: Mouse antigen-binding domains with human constant region domains" 1984, *Proc. Natl. Acad Sci. USA*, 81(21):6851-6855.
Morton, "Vaccination of cattle with outer membrane protein-enriched fractions of *Pasteurella haemolytica* and resistance against experimental challenge exposure," Am. J. Vet. Res., Jul. 1995, 56(7), 875-879.
Murray, "Antigenic analysis of iron-regulated proteins in Pasteurella haemolytica A and T biotypes by immunoblotting reveals biotype-specific epitopes," *J Gen. Microbial*. Feb. 1992; 138( Pt 2):283-288.
Muthukkaruppan, "Monoclonal antibodies against *Salmonella porins*: generation and characterization," Jul. 1992 *Immunol. Lett.*, 33(2):201-206.
Nagaraja, "Influence of environment and other infectious agents on *E. coli* infections," 1984 *Poultry Digest*, 150.
Naiki, "Regulatory Role of Peritoneal NKJ .1+ αT Cells in IL-12 Production During *Salmonella* Infection," *J. lmmunol.*, Aug. 15, 1999;163(4): 2057-2063.
Nardelli-Haefliger, "Oral and Rectal Immunization of Adult Female Volunteers with a Recombinant Attenuated *Salmonella typhi* Vaccine Strain," Dec. 1996 *Infect. lmmun.*, 64(12):5219-5224.
"National Fire Protection Association (NFPA) Rating System" [online], Colorado State University, Fort Collins, CO, [retrieved on Oct. 4, 2012], retrieved from the Internet: <URL:http://www.facilities.colostate.edu/files/forms/safety/CH-23.NFPA.ratings.pdf>, pp. 23-1 to 23-7.
Neilands, "Microbial iron compounds," *Annu Rev Biochem.* 1981;50:715-731.
Neilands, "Microbial envelope proteins related to iron," *Ann. Rev. Microbiol.*, 36:285-309 (1982).
Neugebauer, "Chapter 18: Detergents: An Overview," *Methods in Enzymology: Guide to Protein Purification*, Deutscher, Ed., Academic Press, San Diego, CA, 1990; 182:Cover pg., Publication pg., and 239-253.
Nikaido, "Chapter 3: Outer Membrane." *Escherichia coli and Salmonella typhimurium: Cellular and Molecular Biology, Neidhardt*, eds. *American Societyfor Microbiology*, Washington, D.C., 1987; Cover page, publication page, and 7-22.
Nilius, "Identification of extracellular siderophores of pathogenic strains of Aspergillus fumigatus,"*JMed VetMycol*. 1990;28(5):395-403.
Nothwang, "Two-dimensional separation of membrane proteins by 16-BAC-SDS-PAGE" 2009 *Methods Mol Biol.*, 528:269-277.
Ochoa-Reparaz, "Humoral Immune Response in Hens Naturally Infected with *Salmonella enteritidis* Against Outer Membrane Proteins and Other Surface Structural Antigens," 2004 May-Jun. *Vet. Res.*, 35(3):291-298.
Ogawa, "Immunochemical and biological characterization of outer membrane proteins of Porphyromonas endodontalis," *Infect lmmun*. Nov. 1992; 60(11):4528-4533.
Ogunnariwo, "Evidence for non-siderophore-mediated acquisition of transferrin-bound iron by *Pasteurella multocida,"Microb Pathog*. Jul. 1991; 11(1):47-56.
Ogunnariwo, "Correlation between the ability of Haemophilus paragallinarum to acquire ovotransferrin-bound iron and the expression of ovotransferrin-specific receptors," Jul.-Sep. 1992, *Avian Dis.*, 36(3):655-663.
Okamura, "Differences Among Six *Salmonella* Serovars in Abilities to Colonize Reproductive Organs and to Contaminate Eggs in Laying Hens," Jan.-Mar. 2001 *Avian Dis.*, 45(1):61-69.
Okamura, "Differences in Abilities to Colonize Reproductive Organs and to Contaminate Eggs in Intravaginally Inoculated Hens and in vitro Adhere.nces to Vaginal Explants Between *Salmonella enteritidis* and Other *Salmonella* Serovars," *Avian Dis.*, Oct.-Dec. 2001;45(4):962-971.
Okamura, "Cell-Mediated Immune Responses to a Killed *Salmonella enteritidis* Vaccine: Lymphocyte Proliferation, T-Cell Changes and Interleukin-6 (IL-6), IL-1, IL-2, and IFN-y Production," *Comp. Immunol. Microbial. Infect. Dis.*, Jul. 2004;27(4):255-272.
Osborn, "Proteins of the outer membrane of gram-negative bacteria," 1980 *Annu Rev Microbial.*, 34:369-422.
Overbeek, "Carumonam enhances reactivity of*Escherichia coli* with mono- and polyclonal anti sera to rough *Escherichia coli* J5," *J ClinMicrobial*. Jun. 1987; 25(6):1009-1013.
Perkins, "Probability-Based Protein Identification by Searching Sequence Databases Using Mass Spectrometry Data," *Electrophoresis*, Dec. 1999;20(18):3551-3567.
Petsch, "Endotoxin removal from protein solutions," *Journal of Biotechnology*, 2000; 76:97-119.
Product data Handbook: "Gel Filtration, Principles and Methods" handbook [online]. Amersham Biosciences AB, Uppsala, Sweden, 2002 [retrieved on Sep. 30, 2005]. Retrieved from the Internet: <URL:http://www.bioprocess.amershambiosciences.com/aptrix/ upp00919 .nsf/(File Download)?OpenAgent&docid= 6EEE47990D9F933EC1256F90000DD697&file=18102218AI. pdf>, 124 pgs.
Porter, "*Escherichia coli* antigens as dietary additives for oral immunisation of pigs: trials with pig creep feeds," Jun. 1973 *VetRec.*, 92(24):630-636.
Queen, "A humanized antibody that binds to the interleukin 2 receptor" Dec. 1989 *Proc Natl Acad Sci USA*, 86(24): 10029-10033.
Rae, "Injection Site Reactions," [online]. University of Florida, Department of Animal Sciences, [retrieved on Oct. 16, 2003]. Retrieved from the Internet: <URL:http://www.animal.ufl.edu/ extension/ beef/documents/short94/rae.htm>. 3 pgs.
Riechmann, "Reshaping human antibodies for therapy" Mar. 1988 *Nature*, 24;332(6162):323-327.
Rimler, "Cross-Protection Factor(s) of Pasteurella multocida: Passive-Immunization of Turkeys against Fowl Cholera Caused by Different Serotypes," Oct.-Dec. 1987 *Avian Dis.*, 31(4);884-887.
Rimler, "Solubilization of Membrane-Associated Cross-Protection Factor(s) of Pasteurella multocida," *Avian Dis.*, Apr.-Jun. 1989; 33(2):258-263.

(56) References Cited

OTHER PUBLICATIONS

Rimler, "Partial purification of cross-protection factor(s) from Pasteurella multocida," Oct.-Dec. 1994 *Avian Dis.*, 38(4):778-789.
Robledo, "Outer membrane proteins of *E. coli* in the host-pathogen interaction in urinary tract infection," Feb. 1990 *J Ural.*, 143(2):386-391.
Roof, "Safety, efficacy, and duration of immunity induced in swine by use of an avirulent live *Salmonella choleraesuis*—containing vaccine," *Am J Vet Res.* Jan. 1995;56(1):39-44.
Sack, "Validation of a Volunteer Model of Cholera with Frozen Bacteria as the Challenge," *Infect. Immun.*, May 1998;66(5):1968-1972.
Safety Data Sheet—Deferoxamine Mesylate, Calibiochem, EMD Biosciences, Inc., San Diego, CA, Catalog # 252750, Mar. 2003, pp. 1-4.
Sanchez, "Cholera," Jun. 1997 *Lancet*, 21;349(9068):1825-1830.
Sansonetti, "Shigellosis: from Molecular Pathogenesis of Infection to Protective Immunity and Vaccine Development," Oct.-Dec. 1996 *Res. Immunol.*, 147(8-9):595-602.
Schierack, "Composition of intestinal Enterobacteriaceae populations of healthy domestic pigs" 2007 *Microbiology*, 153:3830-3837.
Schwartz, "Iron-regulated Proteins in Outer Membranes of *Campylobacter jejuni* Diarrhoea Isolates and Immune Response to the Proteins in Patients," Jan. 1994 *Zentralbl Bakteriol.*, 280(3):338-347.
Scopes, "Separation in Solution, Chapter 6," *Protein Purification Principles and Practice*, Second Edition, New York, NY, 1987, Title page, Publication pages, Table of Contents, and pp. 186-220 (23 pages total).
Snipes, "Plasma- and iron-regulated expression of high molecular weight outer membrane proteins by Pasteurella multocida," Aug. 1988 *Am J Vet Res.*, 49(8):1336-1338.
Spellberg, "The Antifungal Vaccine Derived from the Recombinant N Terminus of Als3p Protects Mice against the Bacterium *Staphylococcus aureus*" 2008 *Infect. Immun.*, 76(10):4574-4580.
Spier, "Persistent Experimental *Salmonella*-Dublin Intramammary Infection in Dairy-Cows," *J. Vet. Internal Medicine*, Nov.-Dec. 1991; 5/6:341-350, abstract only (1 pg).
Stewart, *Solid Phase Peptide Synthesis*, 2nd Edition, Pierce Chemical Co., Rockford IL, 1984; Cover page, Publication page, and Table of Contents only (7 pgs.).
Stocker, "Auxotrophic *Salmonella typhi* as Live Vaccine," Apr. 1988 *Vaccine*, (2):141-145.
Stuart, "Iron-suppressible production of hydroxamate by *Escherichia coli* isolates," Jun. 1982 *Infect Immun.*, 36(3):870-875.
Szu, "Laboratory and Preliminary Clinical Characterization of Vi Capsular Polysaccharide-Protein Conjugate Vaccines," Oct. 1994 *Infect. Immun.*, 62(10): 4440-4444.
Tabaraie, "Evaluation of *Salmonella* porins as a broad spectrum vaccine candidate," 1994 *Microbial. Immunol.*, 38:553-559.
Tacket, "Comparison of the Safety and Immunogenicity of *deltaaroC delta aroD* and *delta cya delta crp Salmonella typhi* Strains in Adult Volunteers," Feb. 1992 *Infect. Immun.*, 60(2):536-541.
Tacket, "Clinical Acceptability and Immunogenicity of CVD 908 *Salmonella typhi* Vaccine Strain," 1992 *Vaccine*, 1992;10(7):443-446.
Tatusova, "BLAST 2 Sequences, a New Tool for Comparing Protein and Nucleotide Sequences," *FEMS Microbial Lett.*, May 15, 1999;174(2):247-250, and available at http://www.ncbi.nlm.nih.gov/ gorf/b12.html.
Taylor, "Evaluation of a Bivalent (CVD 103-HgR/CVD 111) Live Oral Cholera Vaccine in Adult Volunteers from the United States and Peru," Sep. 1997 *Infect. Immun.*, 65(9):3852-3856.
Taylor, "A transgenic mouse that expresses a diversity of human sequence heavy and light chain immunoglobulins" Dec. 1992 *Nucleic Acids Res.*, 20:6287-6295.
Title 9: Animals and Animal Products, 9 CFR 113.120, 122, 123, undated, (2 pgs.).
Tokunaga, "Characterization of Porins from the Outer Membrane of *Salmonella typhimurium*," 1979 *Eur. J. Biochem.*, 95:433-439.
Todhunter, "Antibodies to iron-regulated outer membrane proteins of coliform bacteria isolated from bovine intramammary infections," 1991 *Vet. Immunol. Immunopath.*, 28:107-115.
Trach, "Field Trial of a Locally Produced, Killed, Oral Cholera Vaccine in Vietnam," *Lancet*, Jan. 25, 1997;349(9047):231-235.
Trivier, "Influence of iron depletion on growth kinetics, siderophore production, and protein expression of *Staphylococcus aureus*," *FEMSMicrobial. Lett.*, 1995; 127:195-199.
Truscott, "Demonstration of an outer membrane protein with antiphagocytic activity from Pasteurella multocida of avian origin," *Infect Immun.* Jun. 1988;56(6):1538-1544.
Tufano, "Properties of *Yersinia enterocolitica* porins: interference with biological functions of phagocytes, nitric oxide production and selective cytokine release," May 1994 *Res. Microbial.*, 145(4):297-307.
Van Der Helm, "Physical Biochemistry of FEPA and other Siderophore Receptor Proteins," *J. Inorg. Biochem.*, 1995;59(2-3):90 (abstract only).
Vangroenweghe, "Increase of *Escherichia coli* Inoculum Doses Induces Faster Innate Immune Response in Primiparous Cows," 2004 J. Dairy Science, 87:4132-4144.
Van Vliet, "Iron-Responsive Gene Regulation in a *Campylobacter jejuni fur* Mutant" Oct. 1998 *Journal of Bacteriology*, 180(20):5291-5298.
Vasfi Marandi, "The 32 kDa major outer-membrane protein of Pasteurella multocida capsular serotype D," *Microbiology*. Jan. 1996; 142 (Pt 1):199-206.
Verhoeyen, "Reshaping human antibodies: grafting an antilysozyme activity" Mar. 1988 *Science*, 25;239(4847):1534-1536.
Villarreal-Ramos, "Immune Responses in Calves Immunised Orally or Subcutaneously with a Live *Salmonella typhimurium* aro Vaccine," Jan. 1998 *Vaccine*, 6(1):45-54.
Visca, "Siderophore production by *Salmonella* species isolated from different sources," *FEMS Microbial Lett.* Apr. 15, 1991;79(2-3):225-231.
Watson, eds. *Endotoxins and Their Detection With the Limulus Amebocyte Lystate Test*, Alan R. Liss, Inc. 150 5th Avenue, New York, 1982; cover page, publication page, and table of contents only (4 pgs.).
Wellenberg, "Simultaneous intramammary and intranasal inoculation of lactating cows with bovine herpesvirus 4 induce subclinical mastitis," 2002 *Vet. Microbial.*, 86:115-129.
Wells, "What is the Current Milk Quality in the U.S.?" [online]. National Mastitis Council, [retrieved on Aug. 29, 2000]. Retrieved from the Internet: <URL:http://www.nmconline.org/articles/USQuality.htm>. 7 pgs.
Williams, "Novel aerobactin receptor in Klebsiella pneumoniae," 1989 *J. Gen. Microbiol.*, 135:3173-3181.
Yokoyama, "Effect of oral egg antibody in experimental F 18+ *Escherichia coli* infection in weaned pigs," *J. Vet. Med. Sci.* Oct. 1997;59(10):917-921.
Young, "Are You Monitoring Your Peak Milk and Days in Milk at Peak? Part A. Peak Milk," Utah State University, published Jan. 1999. [retrieved on Jan. 19, 2006]. Retrieved from the Internet: <URL:http://extension.usu.edu/files/agpubs/peaka.htm> 2 pgs.
Zhang, "Molecular Pathogenesis of *Salmonella enterica* Serotype Typhimurium-Induced Diarrhea," Jan. 2003 *Infect. Immun.*, 71(1):1-12.
Zhao, "Expression of iron-regulated outer membrane proteins by porcine strains of pasteurella multocida," *Can. J. Vet. Res.* 1995;59(1):46-50.

\* cited by examiner

FIG. 5

| Species | Strain | (500) | (501) | (502) | (503) | (504) | (505) | (506) | (507) | (508) | (509) | (510) | (511) | (512) | (513) | (514) | (515) |
|---|---|---|---|---|---|---|---|---|---|---|---|---|---|---|---|---|---|
| B. anthracis | Sterne | 100 | 100 | 100 | 100 | 100 | 100 | 100 | 100 | 100 | 100 | 100 | 100

FIG. 6

```
B. anthracis Sterne        MKKTMLLKLVSILAIFTLMLVACSDSGKETSKATKDNSSDKPKTVEITDAHGKVKVPVNP   60
B. cereus ATCC 10987       MKKTMLLKLVSILAIFTLMLVACSNPGKETSKATKDNGSDKPKTVEITDAHGKVTVPVNP   60
B. thuringiensis BGSC4Y1   MKKTMLLKLVSILAIFTLMLVACSDSSKETSKATKDNGSDKPKTVEITDAHGKVTVPVNP   60
                           ************************ . ***************************:***

KNVVALDNRTFETLADWGIKLAAAPKDIMPADSAYKKDEKVQNIGNHREPNLEIIAAANP  120
                           KNVVALDNRTFETLADWGIKLAAAPKDVMPADSAYKKDEKVQNIGNHREPNLEIIAAANP  120
                           KNVVALDNRTFETLADWGIKLAAAPKDIMPADSAYKKDEKVQNIGNHREPNLEIIAAANP  120
                           ***************************:********************************

ELVIVGQRFADHYEEIKKLVPNAAVIDLNVDVSEKATKPGENLVKGLKDSTITLGKIFNK  180
                           DLVIVGQRFASHYEEIKKLVPNAAVIDLNVDVSEKATKPGENLVKGLKDSTVTLGKIFDK  180
                           DLVIVGQRFADHYEEIKKLVPNAAVIDLNFDVSEKATKPGENLVKGLKDSTITLGKIFNK  180
                           :*********:*****************:***************************:*

DKEAKQLVADFDKSIEKAKSAYNGKDKVMSVIVTGGNIGFAAPHSGRVWGPMYEIFGWTP  240
                           EKEAKKLVADFDKSIENAKSAYNGKDKVMSVIVTGGNIGFAAPHSGRVWGPMYEIFGWTP  240
                           DKEAKQLVADFDKSIEKAKSAYNGKDKVMSVIVTGGNIGFAAPHSGRVWGPMYEIFGWTP  240
                           :****:**********:*******************************************

ALEVSNSTAGHKGDDVSVEAIAQTNPDWLFVLDRDAATSDAAKSAPAQDVISKSPALQNT  300
                           ALEVSNSTAGHKGDDVSVEAIAQTNPDWLFVLDRDAATSDAAKSAPAQDVISKSPALQNT  300
                           ALEVSNSTAGHKGDDVSVEAIAQTNPDWIFVLDRDAATSDAAKSTPAKDVISKSPALQNT  300
                           ***************************:***************:**:***********

TAVSKKQVVYAPADTYTNESIQTYIELFGNLAKTLAK  337
                           TAVSKKQVIYAPADTYTNESIQTYIELFGNIAKTLAK  337
                           TAVSKKQVIYAPEDTYTNESIQTYIELFGNMAKTLAK  337
                           ********:***:****************:******
```

FIG. 7

```
B. anthracis Sterne        MKKKTGLLLSLTLAASAVLGACGNSDKASSDK---KEFKVGMVTDVGGVDDKSFNQSAWE  57
B. cereus ATCC 10987       MKKKTGLLLSLTLAASAVLGACGNSDKASSDK---KEFKVGMVTDVGGVDDKSFNQSAWE  57
B. thuringiensis BGSC4Y1   MKKKTGLLLSLTLAASTVLGACGNSDKASSDKKEDKDFKVGMVTDVGGVDDKSFNQSSWE  60
                           ****************:************* ::********************.**

GLTKFGKDNNLKKNEGYRYLQSSKDADYIPNLTKFAKDHYNTTFGIGYLMEKSIEKVAEQ 117
                           GLTKFGKDNDLKKNEGYRYLQSSKDADYIPNLTKFAKDHYNTTFGIGYLMEKSIAKVAEQ 117
                           GLQKFGKDNGLKEKTNYRYLQSEKEADYIPNLKKFSKDKYDLTFGIGYKLEGAIKEVAKE 120
                           **.****** **:.:******.*:**************.*.::*****:** **.*:

YPKEQFAIVDTVVEKPNVTSITFKDHEGSFLVGAVAAMTTKSNKVGFVGGVKSPLITKFE 177
                           YPKEQFAIVDTVVEKPNVTSITFKDHEGSFLVGAVAAMTTKSNKVGFVGGVKSPLITKFE 177
                           SSKQQFAIVDTVVDAPNVTSITFKDHEGSFLVGAVAAMSTKSNKVGFVGGMKSDLISKFE 180
                           . *:********: ***********************:***********:** *::***

SGFKAGAKAVNPNIEIVSQYADAFDKPEKGSVLASAMYGGGVDVIYHASGATGNGVFTEA 237
                           SGFKAGAKAVNPNIEIVSQYADAFDKPEKGSVLASAMYGGGVDVIYHASGATGNGVFTEA 237
                           NGFKAGAKAVNPNIEIVSEYAEAFDKPEKGTVLASAMYGQGVDVIYHAAGGTGNGVFTEA 240
                           .*****************:**:********.*********.*******::*.********

KNRKKKGENVWVIGVDRDQNQEGMPENVTLTSMVKRVDVAVAKVAQEAKDGKLKGGKVEE 297
                           KNRKKKGENVWVIGVDRDQNQEGMPENVTLTSMVKRVDIAVAKVAQEAKDGKLKGGKVEE 297
                           KNRKKKGENVWVIGVDRDQHQEGMPENVTLTSMIKRVDVAVEKVAKEAKDGKLKGGKIEA 300
                           *******************:*************:****:**.***:***********:*

FGLKDDGVGIAKTTDNVKKVNPEILTKVEEFEKKITDGEIKVPATDEEYKAYEASLKK   355
                           FGLKDDGVGIAKTTDNVKKVNPEILTKVEEFEKKITDGEIKVPATDEEYKTYEASLKK   355
                           FGLKDDGIGISKTTDNVKKVNPEILTKVEEFEKKITDGEIKVPATDKEYKEYEASLKK   358
                           *******:**:************************************::*** *******
```

FIG. 8

```
B. anthracis Sterne      ---MIMIKKKYMNAFVIAATLAVPFSSIMAPIAKAEAAVEMKAASKLADGTYDVILKTYKD   58
B. cereus ATCC 10987     MTLIMIKKKHVNAFVIAATLVVPFSGIMAPIAKAEAAVEMKANSRLTDGTYDVVFKAYKD   60
B. thuringiensis BGSC4Y1 ----MIKKKYMNAFVIAATLAVPFSGMAPIAKAEAVVEMKAASKLADGTYDVILKTYKD   56
                             :*:***::*****:****:**** ***:********* *:*:*:********

B. anthracis Sterne      KTNDTSVASTYLKNLKVTIQGDKKIVTLTVQDSSYFQLRVEDTNKVGTFHDVKVISEDK  118
B. cereus ATCC 10987     KTNEASIASKYLKDAKVTIQGNKKIVTLTLATDSNYFKEFKVENPNQLGTYQDVKVISESA 120
B. thuringiensis BGSC4Y1 KTNDTSVASTYLKNAKVTIQGDKKIVTLTVQDSSYFQLRVEDPKKLGTFHDVKVISEDK  116
                         ***: :.:**.***: ****.******:. ::.***:: :*:  : ** :*******

B. anthracis Sterne      ANNGTKVVQFEIDEFSKKYNMQMHILIPAIKYDHKYQVQFEIDASAIEQKPKFSDVPTWA  178
B. cereus ATCC 10987     ANNGTKVVQFELGDFSKKYNMKLHIVIPAMQYDHHFQVQFEVDGSTIKKESKFSDVPAWA  180
B. thuringiensis BGSC4Y1 ANNGTKVVQFEIDEFSKKYNMQMHILIPAIKYDHKYQVQFEIDASAIEQKPKFSDVPTWA  176
                         ***********: :******: *:**: :***::****:*.* **:: .******:**

B. anthracis Sterne      QESVQYLVDKEAVHGKPDGTFAPAESIDRSSAAKILATVLRLEIKKDAKPSFPDAQNHWA  238
B. cereus ATCC 10987     QESVQYLVDKEAVHGKPDGTFAPAENIDRSSAAKILATVLATVLGLEIKKDAKPSFPDAQNHWA  240
B. thuringiensis BGSC4Y1 QESVQYLVDKGAVNGKPDGTFAPAESIDRSSAAKIVATVLGLEIKKDAKPSFPDAKNHWA  236
                         ********** **:**********.********::****  :**************:***

B. anthracis Sterne      TPYIAAVEKAGIVKGDEKGNFNPSGLINRASMASMLVNAYKLERNENIKLPKEFADLNNH  298
B. cereus ATCC 10987     TPYIAAVEKAGIVKGDERGNFNPSGLINRASMASMLVNAYKLERNENIKLPKEFADLNNH  300
B. thuringiensis BGSC4Y1 TPYIAAVEKAGIVKGDERGNFNPSGLINRASMASMLVNAYKLERNENIKLPKEFADLNNH  296
                         *****************:******************************************

B. anthracis Sterne      WGAKYANILIQEKISIGTDNGWAPNKAVSRAEAAQFIAKADKLKKEMK     346
B. cereus ATCC 10987     WGAKYANILIQENISIGTDNGWAPDKAVSRAEAAQFIAKADKLKK----    345
B. thuringiensis BGSC4Y1 WGAKYANILIQEKISIGTDNGWAPDKAVSRAEAAQFIAKADKLK----    340
                         ************:***********:*****************:**
```

POLYPEPTIDES AND IMMUNIZING COMPOSITIONS CONTAINING *BACILLUS* POLYPEPTIDES AND METHODS OF USE

CROSS-REFERENCE TO RELATED APPLICATION

This application claims priority to U.S. Provisional Patent Application No. 62/347,454, filed Jun. 8, 2016, which is incorporated herein by reference.

GOVERNMENT FUNDING

This invention was made with government support under HDTRA 1-09-C-0019 awarded by Defence Threat Reduction Agency. The government has certain rights in the invention.

SEQUENCE LISTING

This application contains a Sequence Listing electronically submitted via EFS-Web to the United States Patent and Trademark Office as an ASCII text file entitled "29300520101_SequenceListing_ST25.txt" having a size of 52 kilobytes and created on Jun. 8, 2017. The information contained in the Sequence Listing is incorporated by reference herein.

BACKGROUND

*Bacillus* is a genus of Gram-positive bacteria and a member of the phylum Firmicutes. Endospores are produced under conditions of environmental stress, which allows the bacteria to persist in a dormant state for extended periods of time and accounts for their persistence and worldwide distribution. Some *Bacillus* species secrete large quantities of enzymes that are of value to industy. Others are pathogenic and secrete toxins and other cytopathic enzymes that function as virulence factors.

*Bacillus anthracis* infection, or anthrax, is a zoonotic disease that occurs naturally in wild and domestic herbivores (e.g., cattle, sheep, goats, camels, antelopes and horses). Anthrax continues to be an important disease of livestock in less developed countries where vaccination is not widespread. It is also considered to be one of the most probable threats against military or civilian targets because of its availability in the environment, ease of spore dissemination, and the rapid lethality that occurs if antibiotic treatment is not initiated promptly. Depending on the mode of transmission, anthrax may manifest as inhalational, gastrointestinal, or cutaneous, with inhalational anthrax having the highest case fatality rate of up to 97% if left untreated. The only human anthrax vaccine licensed in the United States is primarily directed at the protective antigen (PA) toxin component.

*Bacillus cereus* is a foodborne pathogen, causing gastrointestinal infections that tend to be self-limiting but occasionally may have more serious consequences such as fatal toxemia. Many other *Bacillus* species, particularly *B. sustilis* and *B. licheniformin*, have also been incriminated periodically as agents of food poisoning. Skin infections and keratitis have also been resported. However, *B. cereus* has become increasingly recognized as a source of serious and potentially fatal extraintestinal infections including progressive pneumonia, sepsis, and central nervous system infections, particularly in immunocompromised individuals. Nosocomial infections are of particular concern, especially given the ability of *B. cereus* to permeate and persist in the hospital environment, and outbreaks among hospitalized patients are well-documented.

*Bacillus thuringiensis* is an insecticidal pathogen that has been used extensively as a biopesticide. Although infection of humans is rare, cases have been documented. Because *B. thuringiensis* and *B. cereus* are closely related and appear to be able to exchange genetic material on plasmids, there are many unresolved questions concerning the safety of exposure to aerosolized *B. thuringiensis* during large-scale insect eradication operations.

Although *Bacillus anthracis, B. cereus* and *B. thuringiensis* are well defined and remain the best-known. Other species of *Bacillus* have been increasingly implicated in a wide range of infections in mammals and humans including abscesses, bacteremia/septicemia, ear infections, endocarditis, wound and burn infections, meningitis, ophthalmitis, osteomyelitis, peritonitis and respiratory and urinary tract infections. Most of these occur as secondary infections or mixed infections often in an immunodeficient or immunocompromised host, but a significant proportion are now being reported as primary infections in healthy individuals generating severe and often lethal outcomes. Most frequently implicated in these types of infections are *B. cereus, B. licheniformis*, and *B. subtilis*, although *B. brevis, B. alvei, B. circulars, B. coagulans, B. macerans, B. pumilus, B. sphaericus* and *B. thuringiensis* occasionally cause infections. As secondary invaders, *Bacillus* species can exacerbate preexisting infections by producing tissue damaging toxins or metabolites that have been shown to interfere with treatment.

SUMMARY

This disclosure relates to polypeptides natively expressed by *Bacillus* spp. In one aspect, this disclosure describes a composition that includes at least two polypeptides natively expressed by a *Bacillus* spp. at greater level when the *Bacillus* spp. is grown in culture medium that has an iron chelator compared to when the *Bacillus* spp. is grown in culture medium without the iron chelator. In some embodiments, the composition can include two or more of: a first polypeptide having a molecular weight of 36 kDa and an amino acid sequence similar to that of SEQ ID NO:1; a second polypeptide having a molecular weight of 35 kDa and an amino acid sequence similar to that of SEQ ID NO:2; a third polypeptide having a molecular weight of 35 kDa and an amino acid sequence similar to that of SEQ ID NO:3; a fourth polypeptide having a molecular weight of 39 kDa and an amino acid sequence similar to that of SEQ ID NO:4; a fifth polypeptide having a molecular weight of 35 kDa and an amino acid sequence similar to that of SEQ ID NO:5; a sixth polypeptide having a molecular weight of 36 kDa and an amino acid sequence similar to that of SEQ ID NO:6; a seventh polypeptide having a molecular weight of 62 kDa and an amino acid sequence similar to that of SEQ ID NO:7; an eighth polypeptide having a molecular weight of 32 kDa and an amino acid sequence similar to that of SEQ ID NO:8; a ninth polypeptide having a molecular weight of 36 kDa and an amino acid sequence similar to that of SEQ ID NO:9; a tenth polypeptide having a molecular weight of 38 kDa and an amino acid sequence similar to that of SEQ ID NO:10; an eleventh polypeptide having a molecular weight of 39 kDa and an amino acid sequence similar to that of SEQ ID NO:11; a twelfth polypeptide having a molecular weight of 36 kDa and an amino acid sequence similar to that of SEQ ID NO:14; a thirteenth polypeptide having a molecular weight of 36 kDa and an amino acid sequence similar to that of SEQ ID NO:15; or a fourteenth polypeptide having a molecular weight of 35 kDa and an amino acid sequence similar to that of SEQ ID NO:16.

In another aspect, this disclosure describes methods that generally involve administering the polypeptide composition toi a subject.

In another aspect, this disclosure describes antibody compositions that specifically bind to at least one polypeptide summarized above.

In another aspect, this disclosure describes methods that generally involve administering the antibody composition to a subject.

In another aspect, this disclosure describes compositions that include a whole cell that expresses at least two of the polypeptides summarized above.

In another aspect, this disclosure describes methods that generally involve administering the whole cell composition to a subject.

In another aspect, this disclosure describes a kit for detecting the presence of a polypeptide summarized above in a boiological sample.

In another aspect, this disclosure describes a kit for detecting the presence of antibody that specifically binds a polypeptide summarized above in a boiological sample.

In yet another aspect, this disclosure describes a recombinant cell that expresses a polypeptide summarized above.

BRIEF DESCRIPTION OF THE FIGURES

FIG. 5. Protein conservation across *Bacillus* species and strains. The percent amino acid identity for all 16 IRPs was determined using *B. anthracis* Sterne as the query for 10 strains of *B. anthracis,* 8 strains of *B. cereus*, and 6 strains of *B. thuringiensis*. Numbers represent percent identity for the amino acid sequence of protein IDs 500-515 (SEQ ID NOs:1-16) using *B. anthracis* Sterne as the query. Shading represents the heat map with settings for proteins that are not encoded (no fill); or with values ≥73% identity (light gray); ≥90% identity (medium gray); or ≥98% identity (dark gray).

FIG. 6. Cross-species sequence alignment for *Bacillus* proteins in *B. anthracis* Sterne, *B. cereus* ATCC 10987, and *B. thuringiensis* BGSC4Y1 for Protein ID #500 (SEQ ID NO:1). Conservation of amino acid sequence is indicated using the following symbols: (*) positions with a single, fully conserved residue; (:) conservation between groups of strongly similar properties; (.) conservation between groups of weakly similar properties.

FIG. 7. Cross-species sequence alignment for *Bacillus* proteins in *B. anthracis* Sterne, *B. cereus* ATCC 10987, and *B. thuringiensis* BGSC4Y1 for Protein ID #509 (SEQ ID NO:10). Conservation of amino acid sequence is indicated using the following symbols: (*) positions with a single, fully conserved residue; (:) conservation between groups of strongly similar properties; (.) conservation between groups of weakly similar properties.

FIG. 8. Cross-species sequence alignment for *Bacillus* proteins in *B. anthracis* Sterne, *B. cereus* ATCC 10987, and *B. thuringiensis* BGSC4Y1 for Protein ID #510 (SEQ ID NO:11). Conservation of amino acid sequence is indicated using the following symbols: (*) positions with a single, fully conserved residue; (:) conservation between groups of strongly similar properties; (.) conservation between groups of weakly similar properties.

DETAILED DESCRIPTION OF EXEMPLARY EMBODIMENTS

Figure 1:
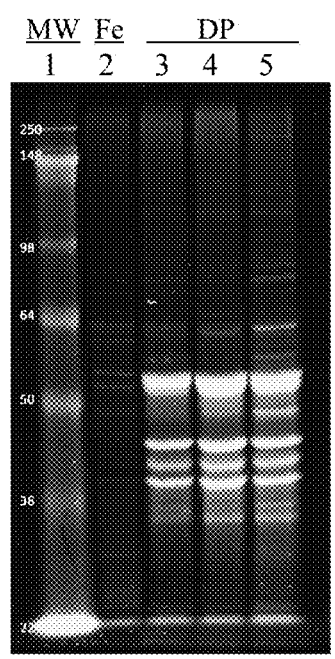
FIG. 1. SDS-PAGE analysis of polypeptides isolated from *B. anthracis* Sterne grown in either iron-rich (Fe, Lane 2) or iron-restricted (DP, Lanes 3-5) medium. Lane 1: molecular weight standard.

This disclosure provides polypeptides compositions including the polypeptides, cells that express the polypeptides, compositions including cells that express the polypeptides, antibodies that specifically bind to the polypeptides, and methods of making and using the polypeptides, cells, and antibodies. As used herein, "polypeptide" refers to a polymer of amino acids linked by peptide bonds. Thus, for example, the terms peptide, oligopeptide, protein, and enzyme are included within the definition of polypeptide. This term also includes polypeptides that may include one or more post-expression modifications of the polypeptide such as, for example, a glycosylation, an acetylation, a phosphorylation, and the like. The term polypeptide does not connote a specific length of a polymer of amino acids. A polypeptide may be isolatable directly from a natural source or can be prepared with the aid of recombinant, enzymatic, or chemical techniques. In the case of a polypeptide that is naturally occurring, such a polypeptide is typically isolated.

An "isolated" polypeptide is one that has been removed from its natural environment. For instance, an isolated polypeptide is a polypeptide that has been removed from the cytoplasm or from the membrane of a cell, and many of the polypeptides, nucleic acids, and other cellular material of its natural environment are no longer present.

A polypeptide characterized as "isolatable" from a particular source is a polypeptide that, under appropriate conditions, is produced by the identified source, although the polypeptide may be obtained from an alternate source using, for example, conventional recombinant, chemical, or enzymatic techniques. Thus, characterizing a polypeptide as "isolatable" from a particular source does not imply any specific source from which the polypeptide must be obtained or any particular conditions or processes under which the polypeptide must be obtained. Thus, a polypeptide characterized as "isolatable" from an identified microbe may be natively expressed by that microbe. "Natively expressed" refers to a polypeptide whose coding region is transcribed by the microbe under appropriate conditions in the absence of any genetic modification to the microbe, regardless of whether the microibe actually possesses any genetifc modifications.

A "purified" polypeptide is one that is at least 60% free, preferably at least 75% free, and most preferably at least 90% free from other components with which they are naturally associated. Polypeptides that are produced outside the organism in which they naturally occur, e.g., through chemical or recombinant means, are considered to be isolated and purified by definition, since they were never present in a natural environment.

As used herein, a "polypeptide fragment" refers to a portion of a polypeptide that results from digestion of a polypeptide with a protease.

Generally, a polypeptide may be characterized by molecular weight, mass fingerprint, amino acid sequence, nucleic acid that encodes the polypeptide, immunological activity, detection by 2D gel electrophoresis, or any combination of two or more such characteristics. The molecular weight of a polypeptide, typically expressed in kilodaltons (kDa), can be determined using routine methods including, for instance, gel filtration, gel electrophoresis including sodium dodecyl sulfate (SDS) polyacrylamide gel electrophoresis (PAGE), capillary electrophoresis, mass spectrometry, liquid chromatography (including HPLC), and calculating the molecular weight from an observed or predicted amino acid sequence. Unless indicated otherwise, molecular weight refers to molecular weight as determined by resolving a polypeptide using an SDS polyacrylamide gel having a stacking gel of about 4% and a resolving gel of about 10% under reducing and denaturing conditions.

As used herein, a "mass fingerprint" refers to a population of polypeptide fragments obtained from a polypeptide after digestion with a protease. Often, a mass fingerprint can be generated by digesting a polypeptide with trypsin. In principle, however, a mass fingerprint may be generated by digesting the polypeptide with any suitable protease. Typically, the polypeptide fragments resulting from a digestion are analyzed using a mass spectrometric method. Each polypeptide fragment is characterized by a mass, or by a mass (m) to charge (z) ratio, which is referred to as an "m/z ratio" or an "m/z value." Methods for generating a mass fingerprint of a polypeptide are routine. An example of such a method is disclosed in Example 3.

The polypeptides described herein may be iron-regulated. As used herein, a "iron-regulated polypeptide" is a polypeptide that is natively expressed by a microbe at a greater level when the microbe is grown in low metal cell culture conditions compared to when the same microbe is grown in high metal cell culture conditions. Low metal and high metal conditions are described in more detail below. For instance, certain iron-regulated polypeptides produced by *Bacillus* spp. are not expressed at detectable levels during growth of the microbe in high metal conditions but are expressed at detectable levels during growth in low metal conditions.

Examples of iron-regulated polypeptides isolatable from a *Bacillus* spp. include the polypeptides identified in Table 1 that are isolatable from *B. anthracis*.

Additional examples of iron-regulated polypeptides include recombinantly-produced versions of polypeptides described herein. A recombinantly-produced polypeptide may include the entire amino acid sequence translatable from an mRNA transcript. Alternatively, a recombinantly-produced iron-regulated polypeptide can include a fragment or portion of the entire translatable amino acid sequence. For example, a recombinantly-produced iron-regulated polypeptide may lack a cleavable sequence at either terminal of the polypeptide—e.g., a cleavable signal sequence at the amino terminal of the polypeptide.

Polypeptide Sequence Similarity and Polypeptide Sequence Identity

Table 1 summarizes identifying characteristics of reference polypeptides natively expressed by reference microbe *B. anthracis* Sterne.

TABLE 1

Characteristics of reference polypeptides

| ID #[a] | GI Number | Molecular Weight (kDa)[b] | Present by 2D gel/MS[c] | Present by iTRAQ | Iron-regulation[d] | Immunogenicity[e] | Animal protection[f] |
|---|---|---|---|---|---|---|---|
| 500 | 49187940 | 36 | + | + | IR | + | + |
| 501 | 49188214 | 35 | + | + | IR | + | + |
| 502 | 49183364 | 35 | + | + | IR | + | + |
| 503 | 49187938 | 39 | ND | + | IR | NT | + |
| 504 | 49187261 | 35 | + | + | IR | + | + |
| 505 | 49187419 | 36 | + | + | IR | + | + |
| 506 | 49184121 | 62 | + | + | IR | NT | + |
| 507 | 49187436 | 32 | + | + | IR | NT | + |
| 508 | 49185110 | 36 | + | + | IR | NT | + |
| 509 | 49186642 | 38 | + | + | IR | NT | + |
| 510 | 49184042 | 39 | + | + | IR | NT | + |
| 511 | 49187438 | 17 | ND | ND | U | + | + |
| 512 | 49187437 | 100 | ND | ND | U | + | + |
| 513 | 49183606 | 36 | + | + | IR | NT | + |
| 514 | 49187312 | 36 | + | + | IR | NT | + |
| 515 | 49185969 | 35 | + | + | IR | NT | + |

[a]ID#, unique number assigned to each polypeptide for tracking purposes.

[b]Molecular weight (predicted).

[c]A protein is considered to be present (+) under iron restriction if detected by 2D gel/mass spectroscopy or in iTRAQ. ND, not detected.

[d]Iron regulation was determined using criteria described in Example 5. IR, iron-regulated; U, iron regulation unknown.

[e]Immunogenicity of individual proteins was determined by antibody and/or T cell recall responses to a purified recombinant protein in mice immunized with either the iron-restricted extract or a mix of recombinant proteins. NT, not tested.

[f]Protection is considered positive (+) if the protein was present in a protective immunizing composition of extract or recombinants (experiments shown in FIGS. 3 and 4), either by mass spectroscopy, by iTRAQ, or through production of antibodies to recombinant proteins from mice immunized with the protective extract vaccine.

Table 1 identifies two polypeptides whose iron-regulation has not been established with certainty. These polypeptides have been identified through bioinformatics analysis using structural similarity to known iron receptor proteins or functional roles in iron acquisition or storage. Additional examples of polypeptides whose metal regulation is uncertain include recombinantly-produced versions of polypeptides described herein. A recombinantly-produced polypeptide may include the entire amino acid sequence translatable from an mRNA transcript. Alternatively, a recombinantly-produced polypeptide whose metal regulation is uncertain can include a fragment or portion of the entire translatable amino acid sequence. For example, a recombinantly-produced polypeptide whose metal regulation is uncertain may lack a cleavable sequence at either terminal of the polypeptide—e.g., a cleavable signal sequence at the amino terminal of the polypeptide.

Whether a polypeptide is an iron-regulated polypeptide or a non-iron-regulated polypeptide can be determined by methods useful for comparing the presence of polypeptides, including, for example, gel filtration, gel electrophoresis including sodium dodecyl sulfate-polyacrylamide gel electrophoresis (SDS-PAGE) and/or 2D gel electrophoresis, capillary electrophoresis, mass spectrometry, isobaric tags for relative and absolute quantification (iTRAQ), and liquid chromatography including HPLC. Separate cultures of a microbe can be grown under high metal conditions and under low metal conditions, polypeptides may be isolated as described herein, and the polypeptides present in each culture can be resolved and compared. Typically, an equal amount of polypeptides from each culture is used. For example, polypeptides can be resolved using an SDS polyacrylamide gel having a stacking gel of about 4% and a resolving gel of about 10% under reducing and denaturing conditions. For instance, 30 micrograms (µg) of total polypeptide from each culture may be used and loaded into wells of a gel. After running the gel and staining the polypeptides with Coomassie Brilliant Blue, the two lanes can be compared. When determining whether a polypeptide is or is not expressed at a detectable level, 30 µg of total polypeptide from a culture is resolved on an SDS-PAGE gel and stained with Coomassie Brilliant Blue using methods known in the art. A polypeptide that can be visualized by eye is considered to be expressed at a detectable level, while a polypeptide that cannot be visualized by eye is considered to not be expressed at a detectable level.

Alternatively, whether a polypeptide is an iron-regulated polypeptide or a non-iron-regulated polypeptide can be determined using microarray-based gene expression analysis. Separate cultures of a microbe can be grown under high metal conditions and under low metal conditions, RNA can be extracted from cells of each culture, and differences in RNA expression in cells grown in high metal conditions versus RNA expression in cells grown in low metal conditions can be detected and compared. For example, labeled cDNA can be prepared from 8-10 µg of bacterial RNA using established protocols. The labeled cDNA can be applied to a microarray of the *Bacillus* spp. genome. Such microarrays are commercially available and gene expression using such arrays is routine.

The polypeptides described herein may have immunological activity. "Immunological activity" refers to the ability of a polypeptide to elicit an immunological response in an animal. An immunological response to a polypeptide is the development in an animal of a cellular and/or antibody-mediated immune response to the polypeptide. Usually, an immunological response includes but is not limited to one or more of the following effects: the production of antibodies, B cells, helper T cells, suppressor T cells, and/or cytotoxic T cells, directed to an epitope or epitopes of the polypeptide. "Epitope" refers to the site on an antigen to which specific B cells and/or T cells respond so that antibody is produced. The immunological activity may be protective. "Protective immunological activity" refers to the ability of a polypeptide to elicit an immunological response in an animal that limits infection by a *Bacillus* spp. such as, for example, *B. anthracis, B. cereus, B. licheniformis, B. subtilis, B. brevis, B. alvei, B. circulars, B. coagulans, B. macerans, B. pumilus, B. sphaericus*, and/or *B. thuringiensis*. Whether a polypeptide has protective immunological activity can be determined by methods known in the art such as, for example, methods described in Examples 5-7. For example, a polypeptide, or combination of polypeptides, can protect a immunological model organism such as a mouse against challenge with a *Bacillus* spp. A polypeptide may have seroactive activity. As used herein, "seroactive activity" refers to the ability of a candidate polypeptide to react with antibody present in convalescent serum from an animal infected with a *Bacillus* spp. such as, for example, *B. anthracis, B. cereus, B. licheniformis, B. subtilis, B. brevis, B. alvei, B. circulans, B. coagulans, B. macerans, B. pumilus, B. sphaericus*, and/or *B. thuringiensis*. In some aspects, the convalescent serum may be from an animal infected with *B. anthracis*.

A polypeptide may have immunoregulatory activity. As used herein, "immunoregulatory activity" refers to the ability of a polypeptide to act in a nonspecific manner to enhance an immune response to a particular antigen. Methods for determining whether a polypeptide has immunoregulatory activity are known in the art.

A polypeptide as described herein may have the characteristics of a polypeptide expressed by a reference microbe—i.e., a reference polypeptide. The characteristics can include, for example, molecular weight, mass fingerprint, amino acid sequence, or any combination thereof. The reference microbe can be a Gram-positive microbe, preferably a member of the family Bacillaceae, preferably, *Bacillus* spp. such as, for example, *B. anthracis, B. cereus, B. licheniformis, B. subtilis, B. brevis, B. alvei, B. circulans, B. coagulans, B. macerans, B. pumilus, B. sphaericus*, and/or *B. thuringiensis*. Exemplary strains of *Bacillus* spp. and representative strains are listed in FIG. 5.

For example, when the reference microbe is *B. anthracis* Sterne, a candidate polyeptide may be a polypeptide as described herein if it has a molecular weight of one of the reference polyeptides reflected in Table 1 and has an amino acid sequence that is structurally similar, as described in more detail below, to the amino acid sequence of the reference polypeptide.

As used herein, a polypeptide may be "structurally similar" to a reference polypeptide if the amino acid sequence of the polypeptide possesses a specified amount of sequence similarity and/or sequence identity compared to the reference polypeptide. A polypeptide also may be "structurally similar" to a reference polypeptide if the polypeptide exhibits a mass fingerprint possessing a specified amount of identity compared to a comparable mass fingerprint of the reference polypeptide. Thus, a polypeptide may be "structurally similar" to a reference polypeptide if, compared to the reference polypeptide, it possesses a sufficient level of amino acid sequence identity, amino acid sequence similarity, mass fingerprint similarity, or any combination thereof.

Polypeptide Sequence Similarity and Polypeptide Sequence Identity Structural similarity of two polypeptides can be determined by aligning the residues of the two polypeptides (for example, a candidate polypeptide and any appropriate reference polypeptide described herein) to optimize the number of identical amino acids along the lengths of their sequences; gaps in either or both sequences are permitted in making the alignment in order to optimize the number of identical amino acids, although the amino acids in each sequence must nonetheless remain in their proper order. A reference polypeptide may be a polypeptide described herein or any known iron-regulated polypeptide, as appropriate. A candidate polypeptide is the polypeptide being compared to the reference polypeptide. A candidate polypeptide can be isolated, for example, from a microbe, or can be produced using recombinant techniques, or chemically or enzymatically synthesized.

Unless modified as otherwise described herein, a pairwise comparison analysis of amino acid sequences can be carried out using the BESTFIT algorithm in the GCG package (version 10.2, Madison Wis.). Alternatively, polypeptides may be compared using the Blastp program of the BLAST 2 search algorithm, as described by Tatiana et al. (*FEMS Microbiol Lett,* 174:247-250 (1999)), and available on the National Center for Biotechnology Information (NCBI) website. The default values for all BLAST 2 search parameters may be used, including matrix=BLOSUM62; open gap penalty=11, extension gap penalty=1, gap x_dropoff=50, expect=10, wordsize=3, and filter on.

In the comparison of two amino acid sequences, structural similarity may be referred to by percent "identity" or may be referred to by percent "similarity." "Identity" refers to the presence of identical amino acids. "Similarity" refers to the presence of not only identical amino acids but also the presence of conservative substitutions. A conservative substitution for an amino acid in a polypeptide may be selected from other members of the class to which the amino acid belongs. For example, it is well-known in the art of protein biochemistry that an amino acid belonging to a grouping of amino acids having a particular size or characteristic (such as charge, hydrophobicity, or hydrophilicity) can be substituted for another amino acid without altering the activity of a protein, particularly in regions of the protein that are not directly associated with biological activity. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr so that a free —OH is maintained; and Gln for Asn to maintain a free —NH2. Likewise, biologically active analogs of a polypeptide containing deletions or additions of one or more contiguous or noncontiguous amino acids that do not eliminate a functional activity—such as, for example, immunological activity—of the polypeptide are also contemplated.

Thus, as used herein, reference to a polypeptide as described herein and/or reference to the amino acid sequence of one or more SEQ ID NOs can include a polypeptide with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence similarity to the reference amino acid sequence.

Alternatively, as used herein, reference to a polypeptide as described herein and/or reference to the amino acid sequence of one or more SEQ ID NOs can include a polypeptide with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity to the reference amino acid sequence.

FIG. 5 shows percent identity of 16 polypeptides across 24 strains across three *Bacillus* species using *B. anthracis* Sterne as the query. FIG. 6, FIG. 7, and FIG. 8 show cross-species sequence alignment for Proteins 500 (SEQ ID NO:1), 509 (SEQ ID NO:10), and 510 (SEQ ID NO:11). The alignment indicates amino acids that are conserved in the variants of each polypeptide across three *Bacillus* species. The alignment also shows regions of variability in the variants of each polypeptide across three *Bacillus* species. A person of ordinary skill in the art can deduce from such data regions of the polypeptide in which substitutions, particularly conservative substitutions, may be permitted without unduly affecting biological activity of the modified polypeptide.

Consequently, a polypeptide as described herein can include certain variants including, for example, homologous polypeptides that originate—biologically and/or recombinantly—from microbial species or strains other than the microbial species or strain from which the polypeptide was originally isolated and/or identified.

A polypeptide as described herein also may be designed so that certain amino acids at the C-terminal and/or N-terminal are deleted. For example, one difference between the amino acid sequence of Protein 500 among *B. anthracis* Sterne, *B. cereus* ATCC 10987, and *B. thuringiensis* BGSC4Y1 is that the *B. anthracis* Sterne includes a two-amino-acid addition, and *B. cereus* ATCC 10987 includes a five-amino-acid addition to the N-terminus of the protein compared to the sequence from *B. thuringiensis* BGSC4Y1. Similar N-terminal additions, typically varying from about five amino acids to about 50 amino acids, can be present. Other amino acids additions and/or deletions, at either the N-terminal or the C-terminal, are possible.

A "modification" of a polypeptide as described herein includes an amino acid addition, an amino acid deletion, and/or a polypeptide (or an analog thereof such as, e.g., a fragment thereof) that is chemically or enzymatically derivatized at one or more constituent amino acids. Such a modification can include, for example, a side chain modification, a backbone modification, an N-terminal modification, and/or a C-terminal modification such as, for example, acetylation, hydroxylation, methylation, amidation, and the attachment of a carbohydrate and/or lipid moiety, a cofactor, and the like, and combinations thereof. Modified polypeptides as described herein may retain the biological activity—such as, for example, immunological activity—of the unmodified polypeptide or may exhibit a reduced or increased biological activity compared to the unmodified polypeptide.

A polypeptide as described herein (including a biologically active analog thereof and/or a modification thereof) can include a native (naturally occurring), a recombinant, a chemically synthesized, or an enzymatically synthesized polypeptide. For example, a polypeptide as described herein may be prepared by isolating the polypeptide from a natural source or may be prepared recombinantly by conventional methods including, for example, preparation as a fusion protein in bacteria or other host cells.

A polypeptide expressed by a reference microbe can be obtained by growing the reference microbe under low metal conditions as described herein and the subsequent isolation of a polypeptide by the processes disclosed herein. Alternatively, a polypeptide expressed by a reference microbe can be obtained by identifying coding regions expressed at higher levels when the microbe is grown in low metal conditions—i.e., iron-regulated. An iron-regulated coding region can be cloned and expressed, and the expressed iron-regulated polypeptide may be identified by a process described herein. A candidate polypeptide can be isolatable from a microbe or identified from a microbe, preferably a Gram-positive microbe, more preferably, a member of the family Bacillaceae, preferably, *Bacillus* spp. such as, for example, *B. anthracis, B. cereus, B. licheniformis, B. subtilis, B. brevis, B. alvei, B. circulans, B. coagulans, B. macerans, B. pumilus, B. sphaericus*, and/or *B. thuringiensis*. A candidate polypeptide may also be produced using enzymatic or chemical techniques.

Mass Fingerprint Similarity

A candidate polypeptide may be evaluated by mass spectrometric analysis to determine whether the candidate polypeptide has a mass fingerprint similar to one of the polypeptides expressed by a reference microbe and referred to above by molecular weight. Typically, the candidate polypeptide can be isolated, for instance by resolving the candidate polypeptide by gel electrophoresis and excising the portion of the gel containing the candidate polypeptide. Any gel electrophoresis method that separates polypeptides based on differing characteristics can be used, including one-dimensional or two-dimensional gel electrophoresis, as well as liquid chromatographic separation based on, for instance, hydrophobicity, pI, or size. The candidate polypeptide can be fragmented, for instance by digestion with a protease. Preferably, the protease can cleave the peptide bond on the carboxy-terminal side of the amino acid lysine and the amino acid arginine, except when the amino acid following the lysine or the arginine is a proline. An example of such a protease is trypsin. Methods for digesting a polypeptide with trypsin are routine and known in the art. An example of such a method is disclosed in Example 3.

Methods for the mass spectrometric analysis of polypeptides are routine and known in the art and include, but are not limited to, nano high-pressure liquid chromatography electrospray tandem mass spectrometry (nanoLC-EDI-MS/MS). Often, when a candidate polypeptide is analyzed by mass spectroscopy, both the candidate polypeptide and the reference polypeptide—i.e., the polypeptide from the reference microbe—are prepared and analyzed together, thereby decreasing any potential artifacts resulting from differences in sample handling and running conditions. Preferably, all reagents used to prepare and analyze the two polypeptides are the same. For instance, the polypeptide from the reference microbe and the candidate polypeptide are isolated under substantially the same conditions, fragmented under substantially the same conditions, and analyzed by nanoLC-EDI-MS/MS on the same machine under substantially the same conditions. A candidate polypeptide may be "structurally similar" to a reference polypeptide if it exhibits a mass fingerprint possessing at least 80%, at least 90%, at least 95%, or substantially all of the m/z values present in the spectrum of the reference microbe polypeptide and above the background level of noise are also present in the spectrum of the candidate polypeptide. (See, e.g., United States Patent Application Publication No. 2006/0233824 A1).

In another aspect, a polypeptide can be considered to be a polypeptide as described herein if it has a molecular weight of a reference polypeptide described herein and has a mass fingerprint that includes a subpopulation including at least a specified percentage of the polypeptide fragments of the mass fingerprint of the reference polypeptide.

The mass fingerprint of a candidate polypeptide can be determined by a mass spectrometric method, for instance by nanoLC-EDI-MS/MS. The mass fingerprint of a candidate polypeptide will generally have additional polypeptide fragments and, therefore, can have additional m/z values other than those identified in any particular analysis. When the candidate polypeptide is being compared to a polypeptide as described herein, the candidate polypeptide can be isolatable from a microbe, preferably a Gram-positive microbe, more preferably, a member of the family Bacillaceae, preferably, *Bacillus* spp. such as, for example, *B. anthracis, B. cereus, B. licheniformis, B. subtilis, B. brevis, B. alvei, B. circulans, B. coagulans, B. macerans, B. pumilus, B. sphaericus*, and/or *B. thuringiensis*.

Polynucleotide Sequence Similarity and Polynucleotide Sequence Identity

Polypeptides as described herein also may be identified in terms of the polynucleotide that encodes the polypeptide. Thus, this disclosure provides polynucleotides that encode a polypeptide as described herein or hybridize, under standard hybridization conditions, to a polynucleotide that encodes a polypeptide as described herein, and the complements of such polynucleotide sequences.

As used herein, reference to a polynucleotide as described herein and/or reference to the nucleic acid sequence of one or more SEQ ID NOs can include polynucleotides having a sequence identity of at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to an identified reference polynucleotide sequence.

In this context, "sequence identity" refers to the identity between two polynucleotide sequences. Sequence identity is generally determined by aligning the bases of the two polynucleotides to optimize the number of identical nucleotides along the lengths of their sequences; gaps in either or both sequences are permitted in making the alignment in order to optimize the number of shared nucleotides, although the nucleotides in each sequence must nonetheless remain in their proper order. A candidate sequence is the sequence being compared to a known sequence. For example, two polynucleotide sequences can be compared using the Blastn program of the BLAST 2 search algorithm, as described by Tatiana et al., (*FEMS Microbiol Lett.*, 174:247-250 (1999)), and available on the world wide web at ncbi.nlm.nih.gov/BLAST/. The default values for all BLAST 2 search parameters may be used, including reward for match=1, penalty for mismatch=−2, open gap penalty=5, extension gap penalty=2, gap x_dropoff=50, expect=10, wordsize=11, and filter on.

Finally, a polynucleotide as described herein can include any polynucleotide that encodes a polypeptide as described herein. Thus, the nucleotide sequence of the polynucleotide may be deduced from the amino acid sequence that is to be encoded by the polynucleotide.

This disclosure also provides whole cell preparations of a microbe, where the microbe expresses one or more of the polypeptides described herein. The cells present in a whole cell preparation may be inactivated such that the cells cannot replicate but the immunological activity of the polypeptides as described herein expressed by the microbe is maintained. Typically, the cells may be killed by exposure to agents such as glutaraldehyde, formalin, or formaldehyde.

Compositions

A composition as described herein may include at least one isolated polypeptide described herein, or a number of polypeptides that is an integer greater than one (e.g., at least two, at least three, at least four). Unless a specific level of sequence similarity and/or identity is expressly indicated herein (e.g., at least 80% sequence similarity, at least 90% sequence identity, etc.), reference to the amino acid sequence of an identified SEQ ID NO includes variants having the levels of sequence similarity and/or the levels of sequence identity described herein in the section headed Polypeptide sequence similarity and polypeptide sequence identity.

A recombinantly-produced polypeptide may be expressed from a vector that permits expression of the polypeptide when the vector is introduced into an appropriate host cell. A recombinant cell may be constructed to produce one or more recombinantly-produced polypeptides as described herein and, therefore, can include one or more vectors that include at least one polynucleotide that encodes a polypeptide as described herein. Thus, each vector can include one or more polynucleotides as described herein—i.e., a polynucleotide that encodes a polypeptide as described herein. In some cases, a polynucleotide that encodes a polypeptide as described herein can be under the control of a regulatory polynucleotide—e.g., a promoter—such that the recombinant cell expresses the polypeptide even when the recombinant cell is grown in culture medium that includes iron. Thus, while certain polypeptides described herein are natively expressed by a Bacillus spp. when the Bacillus spp. is grown in low iron conditions—e.g., in culture medium that either lacks iron or includes an iron chelator—the polypeptides may be produced by a recombinant cell grown in iron replete culture medium.

Certain compositions such as, for example, those including recombinantly-produced polypeptides, can include a maximum number of polypeptides. In some embodiments, the maximum number of polypeptides can refer to the maximum total number of polypeptides. Certain compositions can include, for example, no more than 50 polypeptides such as, for example, no more than 40 polypeptides, no more than 30 polypeptides, no more than 25 polypeptides, no more than 20 polypeptides, no more than 15 polypeptides, no more than 10 polypeptides, no more than eight polypeptides, no more than seven polypeptides, no more than six polypeptides, no more than five polypeptides, no more than four polypeptides, no more than three polypeptides, no more than two polypeptides, or no more than one polypeptide. In other embodiments, a maximum number of recombinantly-produced polypeptides may be specified in a similar manner. In still other embodiments, a maximum number of nonrecombinantly-produced polypeptides may be specified in a similar manner.

A composition can include polypeptides isolatable from one microbe, or can be isolatable from a combination of two or more microbes. For instance, a composition can include polypeptides isolatable from two or more Bacillus spp., or from a Bacillus spp. and a different microbe that is not a member of the genus Bacillus. In certain embodiments, a composition can include a whole cell preparation in which the whole cell expresses one or more of the polypeptides as described herein. In some of these embodiments, the whole cell can be a Bacillus spp. In some embodiments, a composition can include whole cell preparations from two, three, four, five, or six strains.

Optionally, a polypeptide as described herein can be covalently bound or conjugated to a carrier polypeptide to improve the immunological properties of the polypeptide. Useful carrier polypeptides are known in the art. The chemical coupling of polypeptides as described herein can be carried out using known and routine methods. For instance, various homobifunctional and/or heterobifunctional cross-linker reagents such as bis(sulfosuccinimidyl) suberate, bis (diazobenzidine), dimethyl adipimidate, dimethyl pimelimidate, dimethyl superimidate, disuccinimidyl suberate, glutaraldehyde, m-maleimidobenzoyl-N-hydroxysuccinimide, sulfo-m-maleimidobenzoyl-N-hydroxysuccinimide, sulfosuccinimidyl 4-(N-maleimidomethyl) cycloheane-1-carboxylate, sulfosuccinimidyl 4-(p-maleimido-phenyl) butyrate and (1-ethyl-3-(dimethyl-aminopropyl) carbodiimide can be used (see, for instance, Harlow and Lane, Antibodies, A Laboratory Manual, generally and Chapter 5, Cold Spring Harbor Laboratory, Cold Spring Harbor, New York, N.Y. (1988)).

The compositions as described herein optionally further include a pharmaceutically acceptable carrier. "Pharmaceutically acceptable" refers to a diluent, carrier, excipient, salt, etc., that is compatible with the other ingredients of the composition, and not deleterious to the recipient thereof. Typically, the composition includes a pharmaceutically acceptable carrier when the composition is used as described herein. The compositions as described herein may be formulated in pharmaceutical preparations in a variety of forms adapted to the chosen route of administration, including routes suitable for stimulating an immune response to an antigen. Thus, a composition as described herein can be administered via known routes including, for example, oral; parenteral including intradermal, transcutaneous and subcutaneous; intramuscular, intravenous, intraperitoneal, etc. and topically, such as, intranasal, intrapulmonary, intramammary, intravaginal, intrauterine, intradermal, transcutaneous and rectally, etc. It is foreseen that a composition can be administered to a mucosal surface, such as by administration to the nasal or respiratory mucosa (e.g., via a spray or aerosol), to stimulate mucosal immunity, such as production of secretory IgA antibodies, throughout the animal's body.

A composition as described herein can also be administered via a sustained or delayed release implant. Implants suitable for use according to the invention are known and include, for example, those disclosed in International Publication No. WO 2001/037810 and/or International Publication No. WO 1996/001620. Implants can be produced at sizes small enough to be administered by aerosol or spray. Implants also can include nanospheres and microspheres.

A composition as described herein may be administered in an amount sufficient to treat certain conditions as described herein. The amount of polypeptides or whole cells present in a composition as described herein can vary. For instance, the dosage of polypeptides can be between 0.01 micrograms (µg) and 300 mg, typically between 0.1 mg and 10 mg. When the composition is a whole cell preparation, the cells can be present at a concentration of, for instance, $10^2$ bacteria/mL, $10^3$ bacteria/mL, $10^4$ bacteria/mL, $10^5$ bacteria/mL, $10^6$ bacteria/mL, $10^7$ bacteria/mL, $10^8$ bacteria/mL, or $10^9$ bacteria/mL. For an injectable composition (e.g. subcutaneous, intramuscular, etc.) the polypeptides may be present in the composition in an amount such that the total volume of the composition administered is 0.5 mL to 5.0 mL, typically 1.0 to 2.0 mL. When the composition is a whole cell preparation, the cells are preferably present in the composition in an amount that the total volume of the composition administered is 0.5 mL to 5.0 mL, typically 1.0 to 2.0 mL. The amount administered may vary depending on various factors including, but not limited to, the specific polypeptides chosen, the weight, physical condition and age of the animal, and the route of administration. Thus, the absolute weight of the polypeptide included in a given unit dosage form can vary widely, and depends upon factors such as the species, age, weight and physical condition of the animal, as well as the method of administration. Such factors can be determined by one of skill in the art. Other examples of dosages suitable for the invention are disclosed in U.S. Pat. No. 6,027,736.

The formulations may be conveniently presented in unit dosage form and may be prepared by methods well known in the art of pharmacy. Methods of preparing a composition with a pharmaceutically acceptable carrier include the step of bringing the active compound (e.g., a polypeptide or whole cell as described herein) into association with a carrier that constitutes one or more accessory ingredients. In general, the formulations are prepared by uniformly and intimately bringing the active compound into association with a liquid carrier, a finely divided solid carrier, or both, and then, if necessary, shaping the product into the desired formulations.

A composition including a pharmaceutically acceptable carrier also can include an adjuvant. An "adjuvant" refers to an agent that can act in a nonspecific manner to enhance an immune response to a particular antigen, thus potentially reducing the quantity of antigen necessary in any given immunizing composition, and/or the frequency of injection necessary in order to generate an adequate immune response to the antigen of interest. An adjuvant in a pharmaceutical composition is, necessarily, exogenous to the organism to which the pharmaceutical composition is administered. Thus, therm "adjuvant" excludes materials that occur naturally in an organism that possess components that can have a degree of adjuvant activity. An adjuvant may include, for example, IL-1, IL-2, an emulsifier, a muramyl dipeptide, dimethyl dioctadecyl ammonium bromide (DDA), avridine, aluminum hydroxide, an oil, a saponin, alpha-tocopherol, a polysaccharide, an emulsified paraffin (including, for instance, EMULSIGEN, MVP Laboratories, Ralston, Nebr.), ISA-70, RIBI, or any other substances known in the art. Certain polypeptides as described herein can have immunoregulatory activity. Such polypeptides may be used as an adjuvant that directly acts as a T cell and/or a B cell activator and/or acts on a specific cell type that enhances the synthesis of various cytokines or activate intracellular signaling pathways. Such polypeptides can augment the immune response to increase the protective index of the existing composition.

In another embodiment, a composition as described herein including a pharmaceutically acceptable carrier can include a biological response modifier, such as, for example, IL-2, IL-4 and/or IL-6, TNF, IFN-α, IFN-γ, and/or other cytokines that effect immune cells. An immunizing composition can also include other components known in the art such as an antibiotic, a preservative, an anti-oxidant, or a chelating agent.

Methods of Making

This disclosure also provides methods for obtaining the polypeptides described herein. The polypeptides and whole cells as described herein may be isolatable from a member of the family Bacillaceae, preferably, *Bacillus* spp. such as, for example, *B. anthracis, B. cereus, B. licheniformis, B. subtilis, B. brevis, B. alvei, B. circulans, B. coagulans, B. macerans, B. pumilus, B. sphaericus*, and/or *B. thuringiensis*. Microbes useful for obtaining polypeptides as described herein and making whole cell preparations are commercially available from a depository such as American Type Culture Collection (ATCC). In addition, such microbes are readily obtainable by techniques routine and known to the art. The microbes may be derived from an infected animal as a field isolate, and used to obtain the polypeptides and/or the whole cell preparations as described herein, or stored for future use, for example, in a frozen repository at from −20° C. to −95° C., or from −40° C. to −50° C., in bacteriological media containing 20% glycerol, and other like media.

When a polypeptide as described herein is to be obtained from a microbe, the microbe can be incubated under low metal conditions. As used herein, the phrase "low metal conditions" refers to an environment, typically bacteriological culture media, that contains an amount of a free metal that causes a microbe to express iron-regulated polypeptides at a detectable level. As used herein, the phrase "high metal conditions" refers to an environment that contains an amount of a free metal that causes a microbe to express an iron-regulated polypeptide at a decreased level compared to expression of the iron-regulated polypeptide under low metal conditions. In some cases, "high metal conditions" can refer to an environment that causes a cell to fail to express one or more of the iron-regulated polypeptides described herein at a detectable level.

In some cases, "high metal conditions" can include an iron-rich natural environment and/or culture in a iron-rich medium without a metal chelator. In contrast, in some cases, "low metal conditions" can include culture in a medium that includes a metal chelator, as described in more detail below. Metals are those present in the periodic table under Groups 1 through 17 (IUPAC notation; also referred to as Groups I-A, II-A, IV-B, V-B, VI-B, VII-B, VIII, I-B, II-B, III-A, IV-A, V-A, VI-A, and VII-A, respectively, under CAS notation). Preferably, metals are those in Groups 2 through 12, more preferably, Groups 3-12. Even more preferably, the metal is iron, zinc, copper, magnesium, nickel, cobalt, manganese, molybdenum, or selenium, most preferably, iron.

Low metal conditions are generally the result of adding a metal chelating compound to a bacteriological culture medium, the use of a bacteriological medium that contains low amounts of a metal, or the combination thereof. High metal conditions are generally present when a chelator is not present in the medium, when a metal is added to the medium, or the combination thereof. Examples of metal chelators include natural and synthetic compounds. Examples of natural compounds include plant phenolic compounds, such as flavenoids. Examples of flavenoids include the copper chelators catechin and naringenin, and the iron chelators myricetin and quercetin. Examples of synthetic copper chelators include, for instance, tetrathiomolybdate, and examples of synthetic zinc chelators include, for instance, N,N,N',N'-Tetrakis (2-pyridylmethyl)-ethylene diamine. Examples of synthetic iron chelators include 2,2'-dipyridyl (also referred to in the art as θ,θ'-bipyridyl), 8-hydroxyquinoline, ethylenediamine-di-O-hydroxyphenylacetic acid (EDDHA), desferrioxamine methanesulphonate (desferol), transferrin, lactoferrin, ovotransferrin, biological siderophores, such as, the catecholates and hydroxamates, and citrate. An example of a general divalent cation chelator is CHELEX resin. Preferably, 2,2'-dipyridyl is used for the chelation of iron. Typically, 2,2'-dipyridyl is added to the media at a concentration of at least 25 µg/mL such as, for example 50 µg/mL.

The medium used to incubate the microbe and the volume of media used to incubate the microbe can vary. When a microbe is being evaluated for the ability to produce one or more of the polypeptides described herein, the microbe can be grown in a suitable volume, for instance, 10 milliliters to 1 liter of medium. When a microbe is being grown to obtain polypeptides for use in, for instance, administration to animals, the microbe may be grown in a fermenter to allow the isolation of larger amounts of polypeptides. Methods for growing microbes in a fermenter are routine and known to the art. The conditions used for growing a microbe preferably include a metal chelator, more preferably an iron chelator, for instance 2,2'-dipyridyl, a pH of between 6.5 and 7.5, preferably between 6.9 and 7.1, and a temperature of 37° C.

In some aspects of the invention, a microbe may be harvested after growth. Harvesting includes concentrating the microbe into a smaller volume and suspending in a media different than the growth media. Methods for concentrating a microbe are routine and known in the art, and include, for example, filtration or centrifugation. Typically, the concentrated microbe is suspended in an appropriate buffer. An example of a buffer that can be used contains Tris-base (7.3 grams/liter), at a pH of 8.5. Optionally, the final buffer also minimizes proteolytic degradation. This can be accomplished by having the final buffer at a pH of greater than 8.0, preferably, at least 8.5, and/or including one or more proteinase inhibitors (e.g., phenylmethanesulfonyl fluoride). Optionally, the concentrated microbe is frozen at −20° C. or below until disrupted.

When the microbe is to be used as a whole cell preparation, the harvested cells may be processed using routine and known methods to inactivate the cells. Alternatively, when a microbe is to be used to prepare polypeptides as described herein, the microbe may be disrupted using chemical, physical, or mechanical methods routine and known to the art, including, for example, boiling, French press, sonication, digestion of peptidoglycan (for instance, by digestion with lysozyme), or homogenization. An example of a suitable device useful for homogenization is a model C500-B AVESTIN homogenizer, (Avestin Inc., Ottawa, Canada). As used herein, "disruption" refers to the breaking up of the cell. Disruption of a microbe can be measured by methods that are routine and known to the art, including, for instance, changes in optical density. Typically, a microbe is subjected to disruption until the percent transmittance is increased by 20% when a 1:100 dilution is measured. When physical or mechanical methods are used, the temperature during disruption is typically kept low, preferably at 4° C., to further minimize proteolytic degradation. When chemical methods are used the temperature may be increased to optimize for the cell disruption. A combination of chemical, physical, and mechanical methods may also be used to solubilize the cell wall of microbe. As used herein, the term "solubilize" refers to dissolving cellular materials (e.g., polypeptides, nucleic acids, carbohydrates) into the aqueous phase of the buffer in which the microbe was disrupted, and the formation of aggregates of insoluble cellular materials. Without intending to be limited by theory, the conditions for solubilization are believed to result in the aggregation of polypeptides as described herein into insoluble aggregates that are large enough to allow easy isolation by, for instance, centrifugation.

The insoluble aggregates that include one or more of the polypeptides as described herein may be isolated by methods that are routine and known to the art. Preferably, the insoluble aggregates are isolated by centrifugation. Typically, centrifugation of polypeptides, such as membrane polypeptides, can be accomplished by centrifugal forces of 100,000×g. The use of such centrifugal forces requires the use of ultracentrifuges, and scale-up to process large volumes of sample is often difficult and not economical with these types of centrifuges. The methods described herein provide for the production of insoluble aggregates large enough to allow the use of continuous flow centrifuges, for instance T-1 Sharples (Alfa Laval, Inc., Richmond, Va.), which can be used with a flow rate of 250 mL/minute at 17 psi at a centrifugal force of 46,000×g to 60,000×g. Other large-scale centrifuges can be used, such as the tubular bowl, chamber, and disc configurations. Such centrifuges are routinely used and known in the art, and are commercially available from such manufactures as Pennwalt, Ltd., GEA Westfalia Separator Division (GEA Mechanical Equipment US, Inc.), or Alpha Laval, Inc.

The final harvested proteins can be washed and/or dialyzed against an appropriate buffer using conventional methods such as, for example, diafiltration, precipitation, hydrophobic chromatography, ion-exchange chromatography, affinity chromatography, or ultra-filtration, followed by washing the polypeptides, for instance, in alcohol, by diafiltration. After isolation, the polypeptides suspended in buffer and stored at low temperature, for instance, −20° C. or below.

In those aspects as described herein where a whole cell preparation is to be made, after growth a microbe can be killed with the addition of an agent such as glutaraldehyde, formalin, or formaldehyde, at a concentration sufficient to inactivate the cells in the culture. For instance, formalin can be added at a concentration of 0.3% (vol:vol). After a period of time sufficient to inactivate the cells, the cells can be harvested by, for instance, diafiltration and/or centrifugation, and washed.

In other aspects, an isolated polypeptide as described herein may be prepared recombinantly. When prepared recombinantly, a polynucleotide encoding the polypeptide may be identified and cloned into an appropriate expression host as described below in Example 5. The recombinant expression host may be grown in an appropriate medium, disrupted, and the polypeptides isolated as described above.

Methods of Use

In another aspect, this disclosure further provides methods of using the compositions as described herein. The methods include administering to an animal an effective amount of a composition as described herein. The animal can be, for instance, avian (including, for instance, chickens or turkeys), bovine (including, for instance, cattle), caprine (including, for instance, goats), ovine (including, for instance, sheep), porcine (including, for instance, swine), bison (including, for instance, buffalo), equine (including, for instance, horses), a companion animal (including, for instance, dogs or cats), members of the family Cervidae (including, for instance, deer, elk, moose, caribou and reindeer), or human.

In some aspects, the methods may further include additional administrations (e.g., one or more booster administrations) of the composition to the animal to enhance or stimulate a secondary immune response. A booster can be administered at a time after the first administration, for instance, one to eight weeks, preferably two to four weeks, after the first administration of the composition. Subsequent boosters can be administered one, two, three, four, or more times annually. Without intending to be limited by theory, it is expected that in some aspects as described herein annual boosters will not be necessary, as an animal will be challenged in the field by exposure to microbes expressing polypeptides present in the compositions having epitopes that are identical to or structurally related to epitopes present on polypeptides of the composition administered to the animal.

In one embodiment, the method can involve making antibody, for instance by inducing the production of antibody in an animal or by recombinant techniques. As used herein, the term "antibody"—when not preceded by a definite or indefinite article—can be used generically to refer to any preparation that includes at least one molecular species of immunoglobulin or a fragment (e.g., scFv, Fab, F(ab')$_2$ or Fv or other modified fragment) thereof. Therefore, "antibody" can generically include one or more monoclonal antibodies and/or a polyclonal antibody preparation. Antibody produced by the method can include antibody that specifically binds at least one polypeptide present in the composition. In this context, an "effective amount" is an amount effective to result in the production of antibody in the animal. Methods for determining whether an animal has produced antibody that specifically binds a polypeptide present in a composition can be determined as described herein. This disclosure therefore further provides antibody that specifically binds to a polypeptide as described herein, and compositions including such antibody.

The method may be used to produce antibody that specifically binds to a polypeptide expressed by a microbe other than the microbe from which the polypeptide of the composition was isolated. As used herein, antibody that can "specifically bind" a polypeptide is antibody that interacts with the epitope of the antigen that induced the synthesis of the antibody, or interacts with a structurally related epitope. At least some of the polypeptides present in the compositions as described herein typically include epitopes that are conserved in the polypeptides of different species and different genera of microbes. Accordingly, antibody produced using a composition derived from one microbe is expected to bind to polypeptides expressed by other microbes and provide broad spectrum protection against gram positive organisms. Examples of gram positive microbes to which the antibody may specifically bind include, for example, a member of the Bacillaceae family, a member of the Clostridiaceae family, or a member of the Listeriaceae family. Exemplary members of the Bacillaceae family include, for example, *Bacillus* spp. such as, for example, *B. anthracis, B. cereus, B. licheniformis, B. subtilis, B. brevis, B. alvei, B. circulans, B. coagulans, B. macerans, B. pumilus, B. sphaericus*, and/or *B. thuringiensis*. Exemplary members of the Clostridiaceae family include, for example, *Clostridium* spp. Exemplary members of the Listeriaceae family include, for example, *Listeria* spp. Therefore, antibody produced using a composition of polypeptides as described herein may be used to identify and characterize polypeptides as described herein independent of the origin, source, and/or manner of obtaining the polypeptide.

In another aspect, this disclosure provides the use of such antibody to target a microbe expressing a polypeptide as described herein or a polypeptide having an epitope structurally related to an epitope present on a polypeptide as described herein. A compound can be covalently bound to an antibody, where the compound can be, for instance, a toxin. Likewise, such compounds can be covalently bound to a bacterial siderophore to target the microbe. The chemical coupling or conjugation of an antibody as described herein, or a portion thereof (such as a Fab fragment), can be carried out using known and routine methods.

In another aspect, this disclosure provides methods for treating an infection in an animal, including a human, caused by a Gram-positive microbe, preferably by a member of the family Bacillaceae, preferably, *Bacillus* spp. such as, for example, *B. anthracis, B. cereus, B. licheniformis, B. subtilis, B. brevis, B. alvei, B. circulars, B. coagulans, B. macerans, B. pumilus, B. sphaericus*, and/or *B. thuringiensis*. As used herein, the term "infection" refers to the presence of the microbe in an animal's body, which may or may not be clinically apparent. An animal with an infection by a member of the genus *Bacillus* that is not clinically apparent is often referred to as an asymptomatic carrier.

Treating an infection can be prophylactic or, alternatively, therapeutic—in this context, treatment after a subject manifests one or more indication of infection by a microbe. Generally, treatment that is prophylactic—in this context, initiated before a subject is infected by a microbe or while an infection remains subclinical—is referred to herein as treatment of a subject that is "at risk" of infection. As used herein, the term "at risk" refers to an animal that may or may not actually possess the described risk—in this context, an animal that may or may not be infected by a particular microbe. Thus, typically, an animal "at risk" of infection by a microbe is an animal present in an area where animals have been identified as infected by the microbe and/or is likely to be exposed to the microbe even if the animal has not yet manifested any detectable indication of infection by the microbe and regardless of whether the animal may harbor a subclinical amount of the microbe. Accordingly, administration of a composition can be performed before, during, or after the animal has first contact with the microbe. Treatment initiated after the animal's first contact with the microbe may result in decreasing the severity of symptoms and/or clinical signs of infection by the microbe, completely removing the microbe, and/or decreasing the likelihood of experiencing a clinically evident infection compared to an animal to which the composition is not administered. The method includes administering an effective amount of the composition as described herein to an animal having, or at risk of having, an infection caused by a Gram-positive microbe, and determining whether the number of microbes causing the infection has decreased. In this context, an "effective amount" is an amount effective to reduce the number of the specified microbes in an animal or reduce the likelihood that the animal experiences a clinically-evident infection compared to an animal to which the composition is not administered. Methods for determining whether an infection is caused by a Gram-positive microbe are routine and known in the art, as are methods for determining whether the infection has decreased.

In another aspect, the present invention is directed to methods for treating one or more symptoms or clinical signs of certain conditions in an animal that may be caused by infection by a Gram-positive microbe, preferably by a member of the family Bacillaceae, preferably, *Bacillus* spp. such as, for example, *B. anthracis, B. cereus, B. licheniformis, B. subtilis, B. brevis, B. alvei, B. circulans, B. coagulans, B. macerans, B. pumilus, B. sphaericus*, and/or *B. thuringiensis*. The method includes administering an effective amount of a composition as described herein to an animal having or at risk of having a condition, or exhibiting symptoms and/or clinical signs of a condition, and determining whether at least one symptom and/or clinical sign of the condition is changed, preferably, reduced.

Exemplary conditions that may be caused by inection by a member of the Bacilliaceae family include, for example, cutaneous anthrax, gastrointestinal anthrax, pulmonary anthrax, abscess formation, opthalmitis, meningitis, brain abscess, kidney infections, urinary tract infections, wound infections, burn infections, postpartum sepsis, pneumonia, pleurisy, endocarditis, gas gangrene-like cutaneous infection, gastroenteritis, peritonitis, meningitis, otitis media, septicemia, and osteomyelitis.

Treating symptoms and/or clinical signs associated with these conditions can be prophylactic or, alternatively, therapeutic—in this context, treatment initiated after the subject exhibits one or more symptoms or clinical signs associated with a condition caused by infection by a Gram-positive microbe. As used herein, the term "symptom" refers to subjective evidence of disease or condition experienced by the patient and caused by infection by a microbe. As used herein, the term "clinical sign" or, simply, "sign" refers to objective evidence of disease or condition caused by infection by a microbe. Symptoms and/or clinical signs associated with conditions referred to herein and the evaluations of such symptoms are routine and known in the art. Treatment that is prophylactic—in this context, treatment that is initiated before a subject manifests symptoms or signs of a condition caused by a microbe—is referred to herein as treatment of a subject that is "at risk" of developing the condition. Thus, typically, an animal "at risk" of developing a condition is an animal present in an area where animals having the condition have been diagnosed and/or is likely to be exposed to a microbe causing the condition even if the animal has not yet manifested symptoms or signs of any condition caused by the microbe. Accordingly, administering a composition can be performed before, during, or after the animal manifests a symptom or clinincal sign of the condition. Treatment initiated after the animal exhihbits a symptom or clinincal sign of a condition may result in decreasing the severity of the symptoms of the condition, or completely resolving the symptoms. In this aspect of the invention, an "effective amount" is an amount effective to prevent the manifestation of symptoms of a disease, decrease the severity of the symptoms of a disease, and/or completely resolve the symptoms. The successful treatment of a gram positive microbial infection in an animal is disclosed in Example 5 (FIG. 3 and FIG. 4), which demonstrates the protection against disease caused by *B. anthracis* in a mouse model by administering a composition as described herein. These mouse models are a commonly accepted model for the study of human disease caused by these microbes.

This disclosure also provides methods for decreasing colonization by gram positive microbes, for instance blocking the attachment sites of gram positive microbe, including tissues of the skeletal system (for instance, bones, cartilage, tendons and ligaments), muscular system, (for instance, skeletal and smooth muscles), circulatory system (for instance, heart, blood vessels, capillaries and blood), nervous system (for instance, brain, spinal cord, and peripheral nerves), respiratory system (for instance, nose, trachea lungs, bronchi, bronchoceles, alveoli), digestive system (for instance, mouth, salivary glands esophagus, liver, stomach, large intestine, or small intestine), excretory system (for instance, kidneys, ureters, bladder and urethra), endocrine system (for instance, hypothalamus, pituitary, thyroid, pancreas and adrenal glands), reproductive system (for instance, ovaries, oviduct, uterus, vagina, mammary glands, testes, and seminal vesicles), lymphatic/immune systems (for instance, lymph, lymph nodes and vessels, mononuclear or white blood cells, such as macrophages, neutrophils, monocytes, eosinophils, basophils, and lymphocytes, including T cells and B cells), and specific cell lineages (for instance, precursor cells, epithelial cells, stem cells), and the like. Preferably, the Gram-positive microbe is a member of the family Bacillaceae, preferably, *Bacillus* spp. such as, for example, *B. anthracis, B. cereus, B. licheniformis, B. subtilis, B. brevis, B. alvei, B. circulars, B. coagulans, B. macerans, B. pumilus, B. sphaericus*, and/or *B. thuringiensis.*

Decreasing colonization in an animal may be performed prophylactically or, alternatively, therapeutically—in this context, initiated after the animal is colonized by the microbe. Treatment that is prophylactic—in this context, initiated before a subject is colonized by a microbe or while any colonization remains undetected—is referred to herein as treatment of a subject that is "at risk" of colonization by the microbe. Thus, typically, an animal "at risk" of colonization by a microbe is an animal present in an area where animals have been identified as colonized by the microbe and/or is likely to be exposed to the microbe even if the animal has not yet manifested any detectable indication of colonization by the microbe and regardless of whether the animal may harbor a subcolonization number of the microbe. Accordingly, administration of a composition can be performed before, during, or after the animal has first contact with the microbe. Treatment initiated after the animal's first contact with the microbe may result in decreasing the extent of colonization by the microbe, completely removing the microbe, and/or decreasing the likelihood that the animal becomes colonized by the microbe compared to an animal to which the composition is not administered. Thus, the method includes administering an effective amount of a composition as described herein to an animal colonized by, or at risk of being colonized by, a Gram-positive microbe. In this context, an "effective amount" is an amount sufficient to decrease colonization of the animal by the microbe, where decreasing colonization refers to one or more of: decreasing the extent of colonization by the microbe, completely removing the microbe, and/or decreasing the likelihood that the animal becomes colonized by the microbe compared to an animal to which the composition is not administered. Methods for evaluating the colonization of an animal by a microbe are routine and known in the art. For instance, colonization of an animal's intestinal tract by a microbe can be determined by measuring the presence of the microbe in the animal's feces. It is expected that decreasing the colonization of an animal by a microbe will reduce transmission of the microbe to humans.

A composition as described herein can be used to provide for active or passive immunization against bacterial infection. Generally, the composition can be administered to an animal to provide active immunization. However, the composition also can be used to induce production of immune products, such as antibody—e.g., a polyclonal antibody preparation or a monoclonal antibody—that can be collected from the producing animal and administered to another animal to provide passive immunity. Immune components such as, for example, antibody can be collected from serum, plasma, blood, colostrum, etc. to prepare compositions (preferably containing the collected antibody) for passive immunization therapies. Antibody compositions including monoclonal antibodies and/or anti-idiotypes can also be prepared using known methods. Chimeric antibodies include human-derived constant regions of both heavy and light chains and murine-derived variable regions that are antigen-specific (Morrison et al., 1984, *Proc. Natl. Acad. Sci. USA*

81(21):6851-6855; LoBuglio et al., 1989, *Proc. Natl. Acad. Sci. USA* 86(11):4220-4224; Boulianne et al., 1984, *Nature* 312(5995):643-646.). Humanized antibodies substitute the murine constant and framework (FR) (of the variable region) with the human counterparts (Jones et al., 1986, *Nature* 321(6069):522-525; Riechmann et al., 1988, *Nature* 332 (6162):323-327; Verhoeyen et al., 1988, *Science* 239(4847): 1534-1536; Queen et al., 1989, *Proc. Natl. Acad. Sci. USA* 86(24):10029-10033; Daugherty et al., 1991, *Nucleic Acids Res.* 19(9): 2471-2476.). Alternatively, certain mouse strains can be used that have been genetically engineered to produce antibodies that are almost completely of human origin; following immunization the B cells of these mice are harvested and immortalized for the production of human monoclonal antibodies (Bruggeman et al. 1997, *Curr. Opin. Biotechnol.* 8(4):455-458; Lonberg et al., 1995, *Int. Rev. Immunol.* 13(1):65-93; Lonberg et al., 1994, *Nature* 368: 856-859; Taylor et al., 1992, *Nucleic Acids Res.* 20:6287-6295.).

Passive antibody compositions and fragments thereof, e.g., scFv, Fab, F(ab')$_2$ or Fv or other modified forms thereof, may be administered to a recipient in the form of serum, plasma, blood, colostrum, and the like. Antibody may, however, also be isolated from serum, plasma, blood, colostrum, and the like, using known methods for later use in a concentrated or reconstituted form such as, for instance, lavage solutions, impregnated dressings and/or topical agents and the like. Passive immunization preparations may be particularly advantageous for the treatment of acute systemic illness, or passive immunization of young animals that failed to receive adequate levels of passive immunity through maternal colostrum. Antibody useful for passive immunization also may be useful to conjugate to various drugs or antibiotics that could be directly targeted to bacteria expressing during a systemic or localized infection a polypeptide as described herein or a polypeptide having an epitope structurally related to an epitope present on a polypeptide as described herein.

Animal models, in particular mouse models, are available for experimentally evaluating the compositions as described herein. These mouse models are commonly accepted models for the study of human disease caused by members of the genus *Bacillus* such as, for example, *B. anthracis*, *B. cereus*, *B. licheniformis*, *B. subtilis*, *B. brevis*, *B. alvei, B. circulans, B. coagulans, B. macerans, B. pumilus, B. sphaericus*, and/or *B. thuringiensis*. In those cases where a member of the genus *Bacillus* causes disease in an animal, the natural host can be used to experimentally evaluate the compositions as described herein.

However, protection in a mouse model is not the only way to assess whether a composition can confer protection to an animal against infection by a *Bacillus* spp. The adaptive immune response consists of two primary divisions: the humoral (antibody) response and the cellular (T cell) response. Following infection by a bacterial pathogen, dendritic cells at the infection site encounter microbial antigens and produce signaling molecules such as, for example, surface receptors and cytokines in response to conserved molecular patterns associated with the specific bacterium. These signals are shaped by the nature of the pathogen and ideally lead to the appropriate antibody and T cell responses that protect the host from disease. While some bacterial diseases are controlled primarily through antibody functions, others require T cell responses or both antibody and T cell responses for protection. The goal of vaccine biology is to identify the immune responses that provide protection and then design a vaccine to reproduce one or more of these responses in humans.

Antibodies can have many different functions in the conferring protection against infection such as, for example, complement fixation, opsonization, neutralization, and/or agglutination. Moreover, some subclasses of antibodies are better than others at specific functions; for example, for complement fixation the following hierarchy exists for human IgG subclasses: IgG3>IgG1>IgG2>IgG4.

Antibody immunological functions can be studied in a variety of ways. For instance, Western blots are used to identify antigen-specific binding based on size of separated proteins, while the standard enzyme-linked immunosorbent assay (ELISA) is used to produce quantitative information about antibody titers within serum. Antibody surface binding studies are used to determine whether antibody in serum recognize antigens on the surface of intact bacteria, an important indicator of whether the antibodies have the potential to work in vivo. Thus, one skilled in the art recognizes that antibody binding assays such as a Western blot, ELISA (e.g., using human antisera), and/or surface binding correlate positively with the specifically-bound antigens providing immunological activity against infection by *Bacillus* spp. However, one skilled in the art further recognizes that a lack of antibody binding in an assay such as, for example, a Western blot, ELISA, or surface binding assay does not mean that the assayed antigen fails to provide immunological activity against infection by *Bacillus* spp. For example, Table 7 provides data showing antibody titer data for certain representative *Bacillus* iron-regulated polypeptides.

Techniques such as opsonophagocytosis assays (OPA), in which antibody and complement-bound bacteria are combined with human or mouse phagocytes to determine levels of bacterial killing, are useful for studying antibody function. Positive OPA results correlate with vaccine-induced protection in a mouse model. (Stranger-Jones et al., 2006, *Proc. Natl. Acad. Sci.* 103(45):16942-16947). A similar oxidative burst assay can be used to assess the level of reactive oxygen species (ROS) by fresh human or mouse neutrophils following interaction with antibody and complement-bound bacteria.

In some cases, one can determine that a candidate polypeptide possesses cell-mediated immunological activity and, therefore, the candidate polypeptide may exhibit immunological activity in the absence of inducing the production of antibodies. (Spellberg et al., 2008, *Infect. Immun.* 76(10): 4575-4580). Cytotoxic or $CD8^+$ T cells primarily kill infected cells directly through various effector mechanisms, while helper $CD4^+$ T cells function to provide important signaling in the way of cytokines. These T cell classes can be further subdivided based on the cytokines they produce, and different subclasses are effective against different bacterial pathogens. T cells are often studied by assessing their phenotypes with flow cytometry, where antibodies are used to visualize the levels of specific surface markers that enable classification of the T cells as, for example, a recently activated $CD4^+$ T cell, a memory $CD8^+$ T cell, etc. In addition, cytokines and other products of T cells can be studied by isolating the T cells from lymphoid tissue and re-stimulating them with cognate antigen. Following antigen stimulation, the T cells produce cytokines that may be visualized by, for example, intracellular cytokine staining coupled with flow cytometry, or collecting the cell supernatants and using Luminex bead technology to measure 15-25 cytokines simultaneously. For example, Table 8 provides cytokine recall response of spleen cells from mice immunized with representative *Bacillus* iron-regulated polypeptides.

Thus, in addition to mouse models, those of ordinary skill in the art recognize that immunological activity commensurate with the methods described herein may correlate with any one or more of the following: Western blot data showing that serum from animals exposed to a *Bacillus* spp. contains antibody that specifically binds to a candidate polypeptide, cell surface binding assays demonstrating that antibody that specifically binds to a candidate polypeptide specifically binds to a *Bacillus* spp., opsonophagocytosis data, and cytokine induction.

In another aspect, this disclosure provides methods for detecting antibody that specifically binds polypeptides as described herein. These methods are useful in, for instance, detecting whether an animal has antibody that specifically binds polypeptides as described herein, and diagnosing whether an animal may have a condition caused by a microbe expressing polypeptides described herein, or expressing polypeptides that share epitopes with the polypeptides described herein. Such diagnostic systems may be in kit form. The methods include contacting an antibody with a preparation that includes a polypeptide as described herein to result in a mixture. The antibody may be present in a biological sample, for instance, blood, milk, or colostrum. The method further includes incubating the mixture under conditions to allow the antibody to specifically bind the polypeptide to form a polypeptide:antibody complex. As used herein, the term "polypeptide:antibody complex" refers to the complex that results when an antibody specifically binds to a polypeptide. The preparation that includes the polypeptides as described herein may also include reagents, for instance a buffer, that provide conditions appropriate for the formation of the polypeptide:antibody complex. The polypeptide:antibody complex is then detected. The detection of antibodies is known in the art and can include, for instance, immunofluorescence or peroxidase. The methods for detecting the presence of antibodies that specifically bind to polypeptides as described herein can be used in various formats that have been used to detect antibody, including radioimmunoassay and enzyme-linked immunosorbent assay.

In another aspect, this disclosure provides a kit for detecting antibody that specifically binds polypeptides as described herein. The antibody detected may be obtained from an animal suspected to have an infection caused by a Gram-positive microbe, more preferably, a member of the family Bacillaceae, preferably, *Bacillus* spp. such as, for example, *B. anthracis, B. cereus, B. licheniformis, B. subtilis, B. brevis, B. alvei, B. circulans, B. coagulans, B. macerans, B. pumilus, B. sphaericus*, and/or *B. thuringiensis*.

The kit can include at least one of the polypeptides as described herein (e.g., one, at least two, at least three, etc.), in a suitable packaging material in an amount sufficient for at least one assay. Optionally, other reagents such as buffers and solutions needed to practice the invention are also included. For instance, a kit may also include a reagent to permit detection of an antibody that specifically binds to a polypeptide as described herein, such as a detectably labeled secondary antibody designed to specifically bind to an antibody obtained from an animal. Instructions for use of the packaged polypeptides are also typically included. As used herein, the phrase "packaging material" refers to one or more physical structures used to house the contents of the kit. The packaging material is constructed by conventional methods, generally to provide a sterile, contaminant-free environment. The packaging material may have a label that indicates that the polypeptides can be used for detecting antibody that specifically binds polypeptides as described herein. In addition, the packaging material contains instructions indicating how the materials within the kit are employed to detect the antibody. As used herein, the term "package" refers to a container such as glass, plastic, paper, foil, and the like, capable of holding within fixed limits the polypeptides, and other reagents, for instance a secondary antibody. Thus, for example, a package can be a microtiter plate well to which microgram quantities of polypeptides have been affixed. A package can also contain a secondary antibody. "Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

In another aspect, this disclosure provides methods for detecting a polypeptide as described herein. These methods are useful in, for instance, detecting whether a biological sample contains a polypeptide as described herein, and diagnosing whether an animal may have a condition caused by a microbe expressing polypeptides described herein, or expressing polypeptides that share epitopes with the polypeptides described herein. Such diagnostic systems may be in kit form. The methods include contacting an antibody that specifically binds to a polypeptide as described herein with a biological sample that may or may not include a polypeptide—either as a component of a whole cell or in a cell-free form—as described herein. The polypeptide (or cell expressing the polypeptide) may be present in a biological sample such as, for example, blood, milk, or colostrum. The method further includes incubating the mixture under conditions to allow the antibody to specifically bind the polypeptide to form a polypeptide:antibody complex. As used herein, the term "polypeptide:antibody complex" refers to the complex that results when an antibody specifically binds to a polypeptide (or a cell expressing the polypeptide). The preparation that includes the antibody may also include reagents, for instance a buffer, that provide conditions appropriate for the formation of the polypeptide:antibody complex. The polypeptide:antibody complex is then detected. The detection of ligands bound to an antibody is known in the art and can include, for instance, immunofluorescence or peroxidase. The methods for detecting the presence of a polypeptide that specifically binds to the antibody can be used in various formats that have been used to detect antibody, including radioimmunoassay and enzyme-linked immunosorbent assay.

In another aspect, this disclosure provides a kit for detecting a polypeptide that specifically binds an antibody that specifically binds to a polypeptide as described herein. The biological sample analyzed by the kit may be obtained from an animal suspected to have an infection caused by a Gram-positive microbe, more preferably, a member of the family Bacillaceae, preferably, *Bacillus* spp. such as, for example, *B. anthracis, B. cereus, B. licheniformis, B. subtilis, B. brevis, B. alvei, B. circulans, B. coagulans, B. macerans, B. pumilus, B. sphaericus*, and/or *B. thuringiensis*.

The kit can include at least one antibody that specifically binds a polypeptide as described herein (e.g., one, at least two, at least three, etc.), in a suitable packaging material in an amount sufficient for at least one assay. Optionally, other reagents such as buffers and solutions needed to practice the invention are also included. For instance, a kit may also include a reagent to permit detection of a polypeptide (or cell that expresses the polypeptide) that specifically binds to the kit antibody, such as a detection antibody and/or a detectably-labeled secondary antibody designed to specifically bind to a detection antibody. Instructions for use of the packaged antibody are also typically included. The packaging material may have a label that indicates that the kit antibody can be used for detecting a polypeptide as described herein. In addition, the packaging material contains instructions indicating how the materials within the kit are employed to detect the polypeptide or cell expressing the polypeptide.

The present invention is illustrated by the following examples. It is to be understood that the particular examples, materials, amounts, and procedures are to be interpreted broadly in accordance with the scope and spirit of the invention as set forth herein.

EXAMPLES

Example 1—Preparation of *Bacillus* Iron-Regulated Polypeptides

Compositions derived from *B. anthracis* Sterne included novel polypeptides expressed under iron restricted growth. Master seed stocks were prepared by inoculating a single colony of the Sterne strain into 100 mL Tryptic Soy Broth (TSB, Difco Laboratories, Detroit, Mich.) followed by incubation in a shaking incubator at 400 rpm and 37° C. overnight. The culture was expanded by a 1/100 dilution into fresh TSB and incubated as before until it reached the mid-log phase of growth. The bacteria were pelleted by centrifugation at 5000×g, 4° C., for 10 minutes. The supernatant was decanted, and an equal volume of PBS was added to resuspend the pellet. The bacteria were pelleted by centrifugation as before and the pellet was resuspended in TSB containing 15-50% glycerol at one-tenth of the original culture volume. Stocks were frozen in aliquots of 100-1000 µL and stored at −80° C. Working seed stocks were prepared using the same procedure but with the initial inoculum obtained from a frozen master stock vial.

The iron-regulated polypeptide (IRP) composition was prepared by inoculating a frozen stock of *B. anthracis* Sterne into 10 mL tryptic soy broth (TSB) supplemented with 200 µM 2,2′-dipyridyl (DP) (Sigma-Aldrich, St. Louis, Mo.). Iron-replete cultures were grown in TSB supplemented with 300 µM $FeCl_3$. Cultures were incubated at 37° C. on a shaker at 400 rpm. After 16-24 hours incubation, 10 mL of culture was transferred into 90 mL prewarmed TSB supplemented with either 400 µM DP or 300 µM $FeCl_3$ and incubated at 37° C. on a shaker at 400 rpm. After 16-24 hours incubation, 90 mL of culture was transferred into 900 mL prewarmed TSB supplemented with 400 µM DP or 300 µM $FeCl_3$ and incubated at 37° C. on a shaker at 400 rpm. After 12-20 hours, the 1 L culture was transferred into a fermentor containing 10 L TSB supplemented with 400 µM DP or 300 µM $FeCl_3$ and prewarmed to 37° C. The fermentor was run for 20-24 hours with a stir rate of 250 rpm, aeration, and pH control. The cells were harvested by centrifugation at 10,000×g for 20 minutes at 4° C., resuspended in PBS, and centrifuged to obtain the final cell pellet. Cell pellets were weighed and stored frozen at −80° C.

To extract the IRPs, the frozen cell pellet was thawed at room temperature, resuspended by the addition of 500 mL of 0.1 M potassium phosphate, pH 8, to the entire pellet produced from a single 10 L fermentation, and incubated at 37° C. for 10-15 minutes. The cells were pelleted at 14,000×g for 20 minutes, the supernatant was decanted, and the pellet was resuspended in 200 mL of a buffer containing 0.1 M potassium phosphate, 20% sucrose, 10 mM EDTA, and four protease inhibitor tablets (cOmplete Protease Inhibitor Cocktail Tablets, Hoffmann-La Roche Ltd., Nutley, N.J.). The cell suspension was distributed into sterile 50 mL conical tubes at a volume of 35-40 mL/tube. The cells were disrupted by sonication (Branson, Danbury, Conn.) at 90% duty and an output of 3 for four rounds of 20 seconds each on ice. The disrupted cell suspension was transferred to a sterile 40 mL round bottom centrifuge tube and centrifuged at 14,000×g for 30 minutes at 4° C. to pellet cell debris. The supernatant was transferred to a new 40-mL tube and centrifuged at 20,000×g for 30 minutes to pellet the membrane fraction. This step was repeated, the supernatant was decanted, and the pellet was resuspended in 5 mL of 0.1 M potassium phosphate (pH 8) containing 1 mM EDTA and one protease inhibitor pellet. The extract preparations were stored frozen at −80° C.

Samples from three different batches of *B. anthracis* extracts grown under iron restriction and one batch grown under iron replete conditions are shown in FIG. 1. These extracts were evaluated by denaturing SDS-PAGE using 10% gels stained with coomassie blue and imaged using a LI-COR Odyssey infrared imaging system (LI-COR Biosciences, Lincoln, Nebr.). The banding profile indicated that the expression of certain polypeptides was increased, especially those with apparent molecular weights between 36 kDa to 64 kDa, when *B. anthracis* was grown under iron restriction (lanes 3-5, DP) relative to growth in the presence of iron (lane 2, Fe). This is similar to what has been observed for other Gram-positive bacteria grown under iron restriction, where the upregulated proteins correspond to receptors and other proteins that are involved in iron acquisition.

Example 2—Differential Expression of Iron-Regulated Polypeptides

The isobaric tags for relative and absolute quantification (iTRAQ) method was used to evaluate changes in the expression of membrane proteins associated with growth of *B. anthracis* in iron-depleted compared with iron-replete medium. Cultures were grown as described in Example 1, and 40 µg of membrane extract was evaluated. The primary amines of peptides and polypeptides were labeled with isobaric tags using ITRAQ-8plex reagents (Applied Biosystems, Life Technologies Corp., Carlsbad, Calif.) according to the manufacturer's instructions. Cation exchange chromatography was applied using an MCX column (Waters Corp., Milford, Mass.), and the peptides were separated using an UltiMate 3000 nano LC system (Dionex Corp., Sunnyvale, Calif.) coupled to ESI mode using a QSTAR XL mass spectrometer (Applied Biosystems, Life Technologies Corp., Carlsbad, Calif.).

Fourteen proteins associated with iron acquisition had a fold increase >1 and were therefore upregulated during growth under iron restricted conditions. Thus, all 14 proteins are considered to be iron-regulated.

TABLE 2

Differential upregulation of *B. anthracis* membrane polypeptides during iron-restricted growth.

| ID # | GI Number | Polypeptide | Molecular weight (kDa)$^a$ | Fold increase by iTRAQ$^b$ | SEQ ID NO |
|---|---|---|---|---|---|
| 500 | 49187940 | iron compound ABC transporter, iron compound-binding protein | 36 | 5.55 | 1 |
| 501 | 49188214 | iron ABC transporter substrate-binding protein | 35 | 5.06 | 2 |
| 502 | 49183364 | iron compound ABC transporter, iron compound-binding protein | 35 | 4.64 | 3 |
| 503 | 49187938 | iron ABC transporter permease | 39 | 4.57 | 4 |
| 504 | 49187261 | iron compound ABC transporter, iron compound-binding protein | 35 | 4.47 | 5 |
| 505 | 49187419 | iron ABC transporter substrate-binding protein | 36 | 4.44 | 6 |
| 506 | 49184121 | oligopeptide ABC transporter, oligopeptide-binding protein | 62 | 3.48 | 7 |
| 507 | 49187436 | iron ABC transporter substrate-binding protein | 32 | 2.65 | 8 |
| 508 | 49185110 | substrate-binding family protein | 36 | 2.64 | 9 |
| 509 | 49186642 | bmp family lipoprotein | 38 | 2.45 | 10 |
| 510 | 49184042 | S-layer protein | 39 | 1.13 | 11 |
| 513 | 49183606 | iron compound ABC transporter, iron compound-binding protein | 36 | 4.31 | 14 |
| 514 | 49187312 | substrate-binding family protein | 36 | 3.89 | 15 |
| 515 | 49185969 | adhesion lipoprotein | 35 | 1.56 | 16 |

$^a$Molecular weight (predicted).
$^b$Fold upregulation of polypeptides in extract vaccine from *B. anthracis* Sterne grown under iron-restricted compared with iron-replete conditions.

Example 3—Detection of Iron-Regulated Polypeptides on Two-Dimensional (2D) Gels Two-dimensional PAGE separation was performed on membrane extracts from *B. anthracis* grown under iron-depleted conditions. The first dimension employed an acidic polyacrylamide system with cationic detergent benzyldimethyl-n-hexadecylammonium chloride (16-BAC) followed by sodium dodecyl sulfate (SDS-PAGE) for the second dimension (Nothwang H G, Schindler J, 2009, *Methods Mol Biol* 528:269-277; MacFarlane D E, 1989, *Anal Biochem* 176:457-463). For the first dimension, a 50 μg sample of membrane extract was solublized in 7.5 M urea, 10% 16-BAC (w/v), 75 mM DTT, and 0.05% pyronin Y, and electrophoresis was conducted using an 8.7% acrylamide gel with a 50 mM phosphoric acid running buffer. Electrophoretic separation was carried out at a current of 15 mA, from anode to cathode, at 4° C. overnight until the dye front migrated out of the gel. The gel was stained with R250 coomassie. Each lane was excised and equilibrated through four changes of 0.1 M Tris, pH 6.8, with further equilibration in reducing buffer (75 mM Tris, 576 mM glycine, 0.3% SDS, 5% β-mercaptoethanol) for five minutes. Gel strips were overlaid onto the second dimension gel and fixed into place with 0.1% agarose. SDS-PAGE (5-16% gradient) separation was performed using a PROTEAN plus dodeca cell (Bio-Rad Laboratories, Inc., Hercules, Calif.) at 25 mA/gel until the dye front migrated out of the gel.

Figure 2:
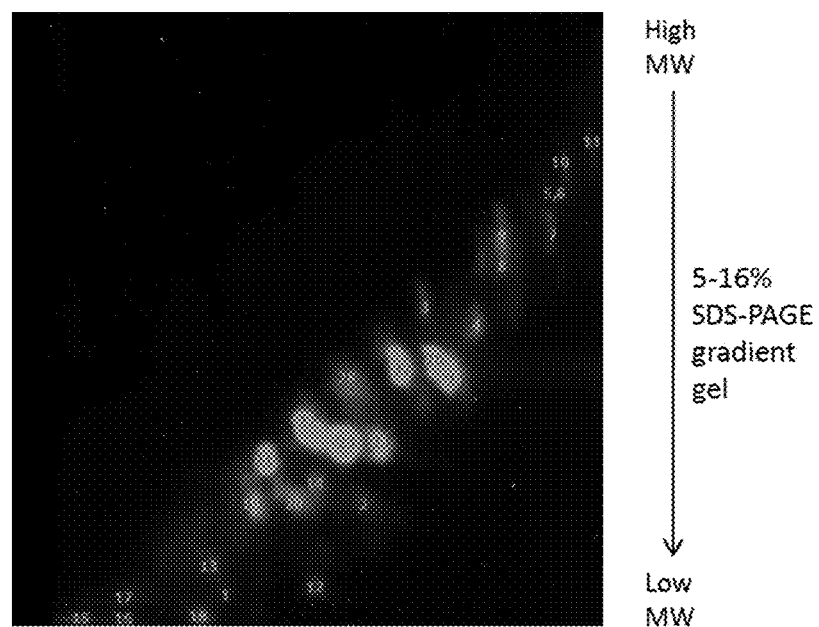
FIG. 2. Two-dimensional gel electrophoresis analysis of membrane extracts from *B. anthracis* Sterne grown in iron-restricted medium. Numbered regions correspond to mass spectroscopy data for protein identification presented in Table 3.

Separation in the first and second dimensions is dependent on molecular weight, hence, larger polypeptides appear in the upper right portion of the second dimension gel, and polypeptides of decreasing molecular weight appear on a diagonal toward the lower left portion of the second dimension gradient gel (FIG. 2). Twenty-eight regions that stained positive for polypeptides were excised from the second dimension gel and analyzed by matrix-assisted laser desorption/ionization mass spectrometry (MALDI-MS) according to the following procedure. Each excised gel spot (indicated by number in FIG. 2) was cut into smaller pieces and washed twice with water for 10 minutes each. All wash volumes were approximately equal to twice the volume of the gel pieces. The gel pieces were washed with a 1:1 mix of acetonitrile and 100 mM ammonium bicarbonate, pH 7.4, for 15-30 minutes. The wash was repeated once or twice as needed to remove the stain. The last wash was replaced with sufficient 100% acetonitrile (ACN) to cover the gel pieces until they turned opaque and sticky, whereupon they were removed and dried in a SpeedVac (ThermoSavant, Holbrook, N.Y.) at 30° C. for 30 minutes. The dried gel pieces were placed into 25-30 μL of 50 mM ammonium bicarbonate containing trypsin at 10 ng/4 and digested for 16-18 hours at 37° C. Following digestion, the mixture was separated by centrifugation, the supernatant was removed, and a volume of 25-30 μL 0.1% trifluoroacetic acid (TFA) was added to extract the peptides. The samples were sonicated intermittently for 30 minutes, and supernatants containing the peptides were transferred into new tubes. The gel extraction was repeated using a solution of 0.1% TFA/30% ACN followed by 0.1% TFA/70% ACN. The pooled supernatants for each spot were concentrated in a SpeedVac to a final volume of 30-70 μL.

MALDI-MS analysis was performed using nano high-pressure liquid chromatography electrospray tandem mass spectrometry (nanoLC-ESI-MS/MS) methods with Thermo Scientific LTQ Orbitraps coupled with Eksigent NanoLC-2D pumps for data acquisition and Scaffold analysis tool (Proteome Software, Portland, Oreg.) to compile the outputs from multiple search algorithms.

A polypeptide was considered to be present if at least two unique peptides from that polypeptide were identified in an excised gel spot. Thirteen polypeptides of interest were identified in the iron restricted extract (Table 3). Most of these proteins were detected in more than one gel spot. This would be expected because of the high sensitivity of the MALDI-MS method and the limit of resolution for PAGE. Thus, the spot that had the largest number of peptides represented for a given polypeptide is indicated as the 2D gel spot number in Table 3. In some cases, multiple polypeptides were present within a spot, such as for polypeptides 500 and 509 in spot 24. This was also anticipated because a majority of these polypeptides do not differ greatly in size, with molecular weights ranging from 32-39 kDa. All 13 polypeptides detected on 2D gels were also identified as IRPs by iTRAQ, as previously described in Example 2.

TABLE 3

Polypeptides identified in extracts of B. anthracis grown under iron restricted conditions.

| ID # | GI Number | Polypeptide | Molecular Weight (kDa)$^a$ | 2D Gel Spot # | SEQ ID NO |
|---|---|---|---|---|---|
| 500 | 49187940 | iron compound ABC transporter, iron compound-binding protein | 36 | 24 | 1 |
| 501 | 49188214 | iron ABC transporter substrate-binding protein | 35 | 2 | 2 |
| 502 | 49183364 | iron compound ABC transporter, iron compound-binding protein | 35 | 20 | 3 |
| 504 | 49187261 | iron compound ABC transporter, iron compound-binding protein | 35 | 2 | 5 |
| 505 | 49187419 | iron ABC transporter substrate-binding protein | 36 | 23 | 6 |
| 506 | 49184121 | oligopeptide ABC transporter, oligopeptide-binding protein | 62 | 4 | 7 |
| 507 | 49187436 | iron ABC transporter substrate-binding protein | 32 | 19 | 8 |
| 508 | 49185110 | substrate-binding family protein | 36 | 20 | 9 |
| 509 | 49186642 | bmp family lipoprotein | 38 | 24 | 10 |
| 510 | 49184042 | S-layer protein | 39 | 21 | 11 |
| 513 | 49183606 | iron compound ABC transporter, iron compound-binding protein | 36 | 2 | 14 |
| 514 | 49187312 | substrate-binding family protein | 36 | 20 | 15 |
| 515 | 49185969 | adhesion lipoprotein | 35 | 19 | 16 |

$^a$Molecular weight (predicted).

Example 4—Identification of Additional Polypeptides Involved in Iron Uptake and Utilization A bioinformatics approach was undertaken to identify additional polypeptides involved in iron uptake. Two additional polypeptides of interest are shown in Table 4. These polypeptides had not been identified in Examples 2 and 3 and are included based on additional information in the NCBI protein database implicating their involvement in iron acquisition. Specifically, these proteins are hemophores that acquire heme from host hemoproteins such as hemoglobin by means of their near-iron transporter, or NEAT, domains. Because these proteins are secreted (Fabian M, 2009, *J Biol Chem* 284:32138-32146; Maresso A W, 2008, *PLoS Pathog* 4:e1000132), they would not be expected to occur in the membrane extracts evaluated in Examples 2 and 3.

TABLE 4

Additional B. anthracis polypeptides involved in iron uptake and utilization.

| ID # | GI Number | Polypeptide | Molecular Weight (kDa)$^a$ | SEQ ID NO |
|---|---|---|---|---|
| 511 | 49187438 | hypothetical protein BAS4443 | 17 | 12 |
| 512 | 49187437 | hypothetical protein BAS4442 | 100 | 13 |

$^a$Molecular weight (predicted).

Example 5—Animal Efficacy Studies

The protective capacity of extract and recombinant IRP vaccines were tested in a well-established mouse model of inhalational anthrax. The IRP extract was prepared as described in Example 1. To prepare the recombinant vaccine, the coding region for each of seven iron-regulated polypeptides was cloned from *B. anthracis* Sterne DNA and expressed in *E. coli*. The recombinant polypeptides were truncated forms of Protein 500 (SEQ ID NO:1), 501 (SEQ ID NO:2), 502 (SEQ ID NO:3), 504 (SEQ ID NO:5), 505 (SEQ ID NO:6), 510 (SEQ ID NO:11), and 511 (SEQ ID NO:12). The signal peptide sequence of each protein was predicted using SignalP (Petersen PMID 21959131) and, in some cases, PredSi (Institute for Microbiology, Technical University of Braunschweig) or Phobius (Stockholm Bioinformatics Centre). Primers specific to each coding region were designed to express the polypeptide without the signal sequence. Primers for amplifying the coding regions encoding the truncated recombinant polypeptides are listed in Table 5. Target sequences were amplified by PCR.

TABLE 5

Primers

| Protein (SEQ ID NO) | Primers (SEQ ID NO) |
|---|---|
| 500 (SEQ ID NO: 1) | Sense: GACTAGGCCTGATTCAGGTAAAG AAACTTCG (SEQ ID NO: 17) Antisense: GACTAAGCTTCTACTTAGC TAAAGTTTTTGC (SEQ ID NO: 18) |
| 501 (SEQ ID NO: 2) | Sense: GACTAGGCCTAAGGATGCGAAGA CTGAAG (SEQ ID NO: 19) Antisense: GACTGTCGACTTATTTCCC TAAAACGAACTC (SEQ ID NO: 20) |

TABLE 5-continued

Primers

| Protein (SEQ ID NO) | Primers (SEQ ID NO) |
|---|---|
| 502 (SEQ ID NO: 3) | Sense: GACTAGGCCTTCTACAGACAAAA AGAACG (SEQ ID NO: 21)<br>Antisense: GACTAAGCTTTTATTTACC AAGAAAGCTCTTC (SEQ ID NO: 22) |
| 504 (SEQ ID NO: 5) | Sense: GACTAGGCCTGACGAAAAAGCAT CGGCAAC (SEQ ID NO: 23)<br>Antisense: GACTAAGCTTTCATTTCCT TACATCTTGTATAC (SEQ ID NO: 24) |
| 505 (SEQ ID NO: 6) | Sense: GACTAGGCCTGACAATAAAAATC AAGCTATAAC (SEQ ID NO: 25)<br>Antisense: GACTAAGCTTTCACTTCTT CGCTGTCATTAC (SEQ ID NO: 26) |
| 510 (SEQ ID NO: 11) | Sense: CGCAGGGATCCGTTGAAATGAAA GCAGCTAGC (SEQ ID NO: 27)<br>Antisense: CGCAGAAGCTTCTATTTCA TTTCTTTCTTC (SEQ ID NO: 28) |
| 511 (SEQ ID NO: 12) | Sense: GACTAGGCCTGCTACAAAACTAG CTGATGG (SEQ ID NO: 29)<br>Antisense: GACTAAGCTTTTATTTAAT ACTGTTCCCATC (SEQ ID NO: 30) |

PCR products were ligated into the pQE30Xa expression vector (Qiagen, Valencia, Calif.), which adds a 6x Histidine tag to the N-terminus. Ligation reactions were used to transform E. coli XL-1 blue. Clones were selected and verified by DNA sequencing (ACGT, Inc., Wheeling, Ill.). Recombinant B. anthracis IRPs were expressed and purified using standard methods. In brief, frozen bacterial stocks (100 µL) were used to inoculate 20 mL of Luria-Bertani Broth containing 100 µg/mL of ampicillin, and the culture was grown at 37° C. in a shaking incubator at 250 rpm. After 16 hours, the culture was diluted added to 1 L of Luria-Bertani Broth containing 100 µg/mL of ampicillin, grown to an optical density (600 nm) of 0.6, and induced by the addition of 1 mM IPTG to a final concentration of 1 mM. Cultures were incubated for an additional 4-20 hours, depending on the optimum time for expression as previously determined for each clone. Bacterial cell pellets were harvested by centrifugation at 4,000×g for 20 minutes at 4° C., washed in PBS, and resuspended in 20 mM Tris buffer containing 100 µg/mL lysozyme. The cells were disrupted by sonication at 50% duty cycle and output (Branson Sonifier, Danbury, Conn.) for eight minutes on ice. The lysate was subjected to centrifugation for 10 minutes at 40,000×g at 4° C. to remove insoluble material. Soluble supernatants were processed by immobilized metal affinity chromatography (HisTrap FF 5 mL, GE Healthcare) to purify the histidine-tagged recombinant polypeptide, followed by anion exchange chromatography to increase the purity and remove endotoxin. The protein concentration was determined using the BCA method (Thermo Scientific, Rockford, Ill.) and purity was assessed by SDS-PAGE and densitometry.

Vaccine efficacy studies were conducted in A/J mice using 15 mice per group. Extract vaccines were formulated to deliver doses of 25 µg, 100 µg, or 300 µg protein. Recombinant vaccines consisted of a mix of all seven recombinant polypeptides containing either 5 µg or 20 µg of each to yield 35 µg or 140 µg total protein per dose, respectively. The positive control was 10 µg protective antigen (PA), which is a component of two toxins found in B. anthracis and is known to confer high levels of protection in this animal model. All vaccines contained 10 µg of CpG per dose and were emulsified in 50% incomplete Freund's adjuvant (IFA). The placebo group consisted of IFA/CpG formulated with PBS, and the naïve group was injected with saline. Mice were immunized subcutaneously in a volume of 100 µL at Day 0 with a booster at Day 28.

On Day 42, mice were challenged intratracheally (IT) with B. anthracis Sterne spores. The challenge dose of B. anthracis spores was prepared as follows using aseptic technique. Spores were cultured in Phage Assay Medium for at least 96 hours to allow germination, outgrowth, and sporulation. Aliquots of 12.5 mL culture were centrifuged at 3,000×g for 30 minutes, and each pellet was resuspended in 50 mL cold water. The spores were passed sequentially through a 3.1 µm and a 1.2 µm filter, heat treated for 30 minutes at 65° C., and pelleted at 4,000×g for 30 minutes. The spore pellets were subjected to a series of four washes with 5-10 mL cold water with a final resuspension in 10 mL. The spores were enumerated using a hemacytometer and resuspended to the target dose of $5 \times 10^5$ spores in 30 µL water. Spore preparations were plated on blood agar to verify the actual concentration of germination-competent spores.

Aerosolized challenge by the intratracheal route was performed on mice that were lightly anesthetized with a mixture of ketamine and xylazine (80 mg/kg ketamine and 20 mg/kg xylazine). The animal was manually restrained in an upright position and a padded forceps was used to gently open the mouth and hold the tongue down to the lower jaw to prevent swallowing. A second investigator then carefully administered 30 µL of fluid to the back of the mouth using a sterile pipette tip and a p100 Pipeteman (Gilson, Middleton, Wis.). This was followed by placing a gloved finger over the mouse's nostrils to prevent obligate nasal breathing. The combination of holding the tongue to prevent swallowing and closing off the nostrils to prevent nasal breathing causes the mouse to inhale through the mouth and aspirate the instilled fluid. An immediate cough by the mouse, which can be detected both audibly and visibly, was used to verify that the procedure was performed correctly. Survival was monitored for 14 days.

Figure 3:
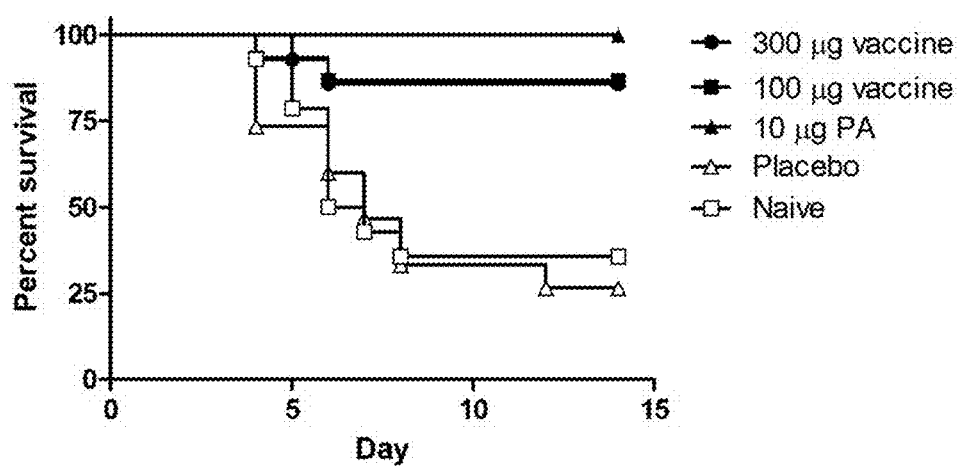
FIG. 3. Kaplan-Meier survival curve of A/J mice immunized twice, four weeks apart, with extract vaccine (100 µg/dose or 300 µg/dose), protective antigen (PA) as a positive control at 10 µg/dose, a placebo (adjuvant only), or saline (naïve). Mice were challenged intratracheally with *B. anthracis* Sterne spores at two weeks after the last immunization.

Results from the first trial are shown in FIG. 3. Thirty-six percent of naïve mice and 27% of placebo mice survived the infection, compared with 86% survival in mice immunized with either 100 µg or 300 µg of extract vaccine. The PA positive control group showed 100% survival, which is typical for this animal model, where mortality is highly influenced by toxin production.

Figure 4:
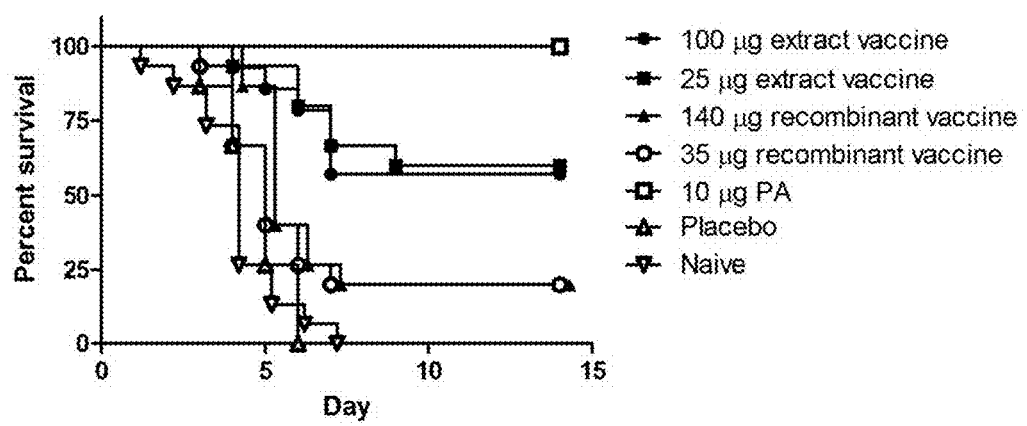
FIG. 4. Kaplan-Meier survival curve of A/J mice immunized twice, four weeks apart, with extract vaccine (100 µg/dose or 300 µg/dose), a 7-valent recombinant IRP vaccine containing 20 µg/dose or 5 µg/dose of each polypeptide, protective antigen (PA) as a positive control at 10 µg/dose, a placebo (adjuvant only), or saline (naïve). Mice were challenged intratracheally with *B. anthracis* Sterne spores at two weeks after the last immunization.

The second vaccine trial showed higher levels of mortality in naïve and placebo mice, neither of which survived infection (FIG. 4). Mice vaccinated with either 25 µg or 100 µg of extract vaccine showed similar levels of survival, at 60% and 57%, respectively. The recombinant vaccine was also protective, with 20% survival at both the 35 µg and 140 µg doses. These two studies indicate that immunization with either iron-restricted extract preparations or mixtures of individual recombinant IRPs protects against infection with aerosolized anthrax spores.

Example 6—Production of Anthrax Toxin Neutralizing Antibodies (TNAs)

Production of lethal toxin is integral to the pathogenesis of anthrax infection. Because antibodies to the PA component of lethal toxin are known to provide protection in the A/J mouse model described in Example 5, sera were evaluated for the production of TNAs. The TNA assay was performed by incubating serial dilutions of serum with a lethal factor/PA mixture previously determined to produce 99% cell death in J774A.1 cells after four hours exposure (Li H, 2008, *J Imm Meth* 333:89-106). Viability was determined by the addition of 2,3-bis-(2-methoxy-4-nitro-5-sulfophenyl)-2H-tetrazolium-5-carboxanilide (XTT), a colorimetric indicator. The TNA titer was calculated as the inverse dilution of serum that resulted in 50% survival (50% effective concentration, or EC50). Sera obtained from mice during the second vaccine trial were evaluated, and the results are shown in Table 6. The lack of detectable TNAs in either of the IRP vaccine groups indicates that the protective immune response was independent of toxin neutralization. In addition, the lack of an antibody response to toxin in IRP-vaccinated survivors at 14 days after challenge (Day 56) suggests that IRP vaccines were able to limit bacterial growth to the extent that there was insufficient toxin produced to stimulate the production of anti-toxin antibodies.

TABLE 6

Toxin neutralizing antibody titers.

| Vaccine | Vaccine dose (µg) | Anthrax TNA titer (EC50) | | |
|---|---|---|---|---|
| | | Day 27 | Day 41[a] | Day 56 |
| IRP extract | 100 | <LOD[b] | <LOD | <LOD |
| IRP recombinant | 140 | <LOD | <LOD | <LOD |
| PA[c] | 10 | 372 | 22,336 | 29,512 |
| Placebo | 0 | <LOD | <LOD | NT[d] |

[a]Day 41 was 1 day prior to challenge, and Day 56 was 14 days after challenge.
[b]<LOD, below the limit of detection.
[c]PA, protective antigen.
[d]NT, not tested (no survivors in placebo group at Day 56).

Example 7—Immunogenicity of IRPs

The immunogenicity of individual IRPs was assessed for both the extract and recombinant vaccines using serum taken at Day 41, one day prior to challenge, from the second vaccine trial. IgG antibody titers were determined by ELISA. In brief, 100 µL of recombinant polypeptide at 2 µg/mL, was added to each well of a 96-well EIA plate (Corning/Costar 3590) and incubated overnight at 4° C. All remaining steps were performed at room temperature. The plate was washed three times with PBS wash buffer (PBS containing 0.05% Tween 20) followed by the addition of 200 µL/well sample buffer consisting of PBS containing 0.05% Tween 20 and 1% bovine serum albumin. After 90 minutes, the sample buffer was replaced with 100 µL/well PBS sample buffer. Serial ⅓ dilutions of the primary antisera were performed in the plate by the addition of 50 µL to the first row, mixing 10 times, and transfer of 50 µL to the next row. The plate was incubated for 90 minutes followed by three washes and addition of 100 µL/well of an HRP conjugated goat anti-mouse IgG, heavy chain specific antibody (Jackson ImmunoResearch). After 90 minutes incubation, the plate was washed four times followed by the addition of 100 µL TMB (BioFx)/well. Color was allowed to develop for 30 minutes, and the reaction was stopped by the addition of 100 µL stop reagent (BioFx). The absorbance was measured at a wavelength of 450 nm, and the titer was calculated as the inverse of the dilution corresponding to an absorbance of 1.0. Controls included a standardized primary serum included on each plate to monitor assay variability and wells that were not coated with antigen, which were subtracted as background.

Mice immunized with IRP extract produced antibodies to five of the seven IRPs included in the recombinant vaccine (Table 7). The lack of antibody to polypeptide r511 is consistent with this hemophore being secreted from the cell, was not detected by mass spectrometry or iTRAQ (Examples 2 and 3), and was selected for inclusion using a bioinformatics approach (Example 4). Mice immunized with IRP extract also did not produce antibody to polypeptide r504. All seven recombinant polypeptides were immunogenic, however, and elicited high titers of IgG antibodies when administered as a mixture containing 20 µg each.

TABLE 7

Specific antibody titers in mice immunized with extract or recombinant IRP vaccines[a]

| | Antibody titer[b] | |
|---|---|---|
| Protein | Extract vaccine | Recombinant vaccine |
| r500 (amino acids 25-337 of SEQ ID NO: 1) | 74,818 | 539,290 |
| r501 (amino acids 34-314 of SEQ ID NO: 2) | 59,012 | 511,178 |
| r502 (amino acids 23-305 of SEQ ID NO: 3) | 28,973 | 380,881 |
| r504 (amino acids 26-315 of SEQ ID NO: 5) | ND | 535,263 |
| r505 (amino acids 31-324 of SEQ ID NO: 6) | 21,660 | 402,410 |
| r510 (amino acids 36-311 of SEQ ID NO: 11) | 28,973 | 105,064 |
| r511 (amino acids 30-152 of SEQ ID NO: 12) | ND | 417,304 |

[a]IgG antibody titers were evaluated at Day 41 Serum from placebo mice did not react with any of the seven IRPs (not shown).
[b]Titers were determined in mice immunized with a total of 100 µg IRP extract or 140 µg IRP recombinant vaccine.

In conjunction with the second vaccine trial shown in FIG. 4, additional mice were immunized in parallel to evaluate cytokine recall responses in a subset of the vaccine groups. This included five mice for each group immunized with 100 µg of extract vaccine, 140 µg of recombinant vaccine, or the placebo negative control. Spleens were harvested on Day 41, processed into mononuclear cell preparations, and cultured individually with 10 µg/mL of individual recombinant IRPs, the mixture of seven recombinant IRPs, or the IRP extract. A medium-only control was included to assess background activity. After 48 hours, the cell supernatants were harvested and frozen at −80° C. until assessment for cytokine production using a mouse Bio-Plex cytokine detection panel (Bio-Rad Laboratories, Hercules, Calif.) and Luminex 100/200 (Luminex Corporation, Austin, Tex.), performed according to the manufacturer's protocol. The net production of cytokine for each polypeptide stimulus was calculated by subtracting the corresponding value for the placebo group.

Spleen cells from mice that were immunized and restimulated with the extract polypeptide mixture in vitro produced a broad range of cytokines, with IL-2, IL-6, IL-17, GM-CSF, TNFα, and IFNγ being predominantly expressed (Table 8). This pattern of cytokine production, taken together with undetectable levels of IL-4, low IL-5, and low IL-10 expression, suggests that the extract vaccine primed animals for a Th1/Th17 polarized response that was associated with protection.

A similar though reduced response was observed when extract-immunized mice were restimulated with the 7-valent recombinant IRP mixture (r500, r501, r502, r504, r505, r510, and r511).

T cell memory responses were further dissected using individual recombinant IRPs. IL-2 was produced in response to each of the seven recombinant IRPs except polypeptide r510, which is consistent with the full-length Protein 510 not being detected in the extract. Other cytokines were produced as well and followed a similar trend, with no IL-4, IL-5, or IL-10 detected and variable levels of other cytokines, especially in response to polypeptides r500, r501, or r502.

Compared to the extract vaccine, mice immunized with the 7-valent recombinant vaccine showed a similar though less vigorous T cell memory response to extract or to the 7-valent recombinant mixture. Again, recombinant polypeptides r500, r501, and r502 seemed to elicit the most vigorous responses, although polypeptide r510 also generated a strong response. These data indicate that adaptive memory responses to IRPs were induced by both extract and recombinant vaccines, and that the responses could be linked to individual proteins contained within the vaccines.

those encoded by *B. anthracis* Sterne would be expected to protect against infection by different strains, including those that are more virulent. For the Example 5 animal efficacy studies, *B. anthracis* Sterne was selected as a seed strain for the extract vaccine due to safety considerations associated with employing a BSL3 agent in manufacturing. Recombinant polypeptide vaccines represent an alternative approach that is not subject to this limitation. Thus, a recombinant anthrax vaccine could employ polypeptides cloned directly from the *B. anthracis* Ames Ancestor strain, which is highly lethal and recognized as a potential bioweapon. To address the possibility of whether a broad spectrum vaccine could be created using extract or recombinants, a bioinformatics approach was undertaken to compare the percent identity of the polypeptides identified in Examples 2, 3, and 4 across a variety of *B. anthracis* strains. Potential vaccine polypep-

TABLE 8

Cytokine recall responses of mice immunized with IRP vaccines.

| Polypeptide stimulus | Vaccine[a] | Cytokine production (pg/mL) | | | | | | | | | |
|---|---|---|---|---|---|---|---|---|---|---|---|
| | | IL-2 | IL-4 | IL-5 | IL-6 | IL-10 | IL-12 | IL-17 | GM-CSF | TNFα | IFNγ |
| Extract | Extract | 163 | — | 15 | 986 | 35 | 38 | 155 | 108 | 81 | 1350 |
| | rBaIRP7 | 83 | — | 24 | 150 | 58 | 17 | 132 | 66 | 16 | 826 |
| rBaIRP7 | Extract | 7 | — | — | 478 | 11 | 23 | 19 | 22 | 57 | 718 |
| | rBaIRP7 | 60 | — | 16 | — | 46 | 7 | 116 | 60 | 23 | 1270 |
| r500 | Extract | 33 | — | — | 9 | — | 5 | 3 | 27 | — | 15 |
| | rBaIRP7 | 93 | — | — | 8 | — | 7 | 19 | 69 | — | 103 |
| r501 | Extract | 25 | — | — | — | — | — | 1 | 23 | — | 13 |
| | rBaIRP7 | 897 | — | 12 | — | 8 | 7 | 12 | 109 | — | 73 |
| r502 | Extract | 15 | — | — | — | — | — | 2 | 17 | — | 10 |
| | rBaIRP7 | 74 | — | 19 | — | 9 | 9 | 15 | 74 | 8 | 64 |
| r504 | Extract | 3 | — | — | — | — | 3 | — | — | — | — |
| | rBaIRP7 | 9 | — | — | — | — | 4 | 3 | — | — | — |
| r505 | Extract | 8 | — | — | 17 | — | 7 | — | 11 | — | — |
| | rBaIRP7 | 28 | — | — | 7 | — | 5 | — | 6 | — | — |
| r510 | Extract | — | — | — | 690 | — | 12 | 3 | — | 5 | — |
| | rBaIRP7 | 78 | — | 7 | — | 26 | 7 | 113 | 30 | 106 | 495 |
| r511 | Extract | 6 | — | — | 26 | — | 6 | — | — | — | — |
| | rBaIRP7 | 23 | — | — | — | 2 | 5 | 8 | — | 3 | 22 |

Example 8—Conservation of Iron-Regulated Polypeptides

*Bacillus anthracis* belongs to the *Bacillus cereus* group, which includes six closely-related species including *B. cereus*, and *B. thuringiensis*. *Bacillus cereus* is a source of food poisoning and causes diarrhea and vomiting, but infections may also become more severe. *Bacillus thuringiensis* is an insect pathogen, but has on occasion been isolated from humans. Because IRPs tend to be evolutionarily conserved, tides were compared by standard protein BLAST (blastp, NCBI) using a database of non-redundant polypeptide sequences and default parameters. The analysis was performed using the extract vaccine strain, *B. anthracis* Sterne, as the query across a subset of the sequenced *B. anthracis* strains available through GenBank. This panel of targeted strains was selected to achieve diversity based on geographic variability and differences in clinical disease and/or outcomes. Information on the selected strains and their sources is shown in Table 9.

TABLE 9

Names and sources of strains used to determine sequence conservation of iron-regulated polypeptides in *B. anthracis*, *B. cereus*, and *B. thuringensis*

| Species | Strain | Source |
|---|---|---|
| *B. anthracis* | Sterne | Cow in S. Africa; Source for attenuated live animal vaccine |
| | Ames Ancestor | Fatal infection of heifer, Texas; progenitor of all Ames strains |
| | CDC 684 | Naturally attenuated strain of Vollum A0488 lineage |
| | H9401 | Patient with gastrointestinal anthrax, Korea |
| | A0248 | Human isolate, USAMRIID |
| | Tsiankovskii-I | Former livestock vaccine strain, USSR |
| | UR-1 | Fatal injectional anthrax in heroin user, Germany |
| | CZC5 | Fatal infection of hippopotamus, Zambia |

TABLE 9-continued

Names and sources of strains used to determine sequence conservation of iron-regulated polypeptides in *B. anthracis*, *B. cereus*, and *B. thuringensis*

| Species | Strain | Source |
|---|---|---|
| | A16 | Deceased mule, China |
| | BF1 | Cow, Germany |
| *B. cereus* | NVH0597-99 | Spice mixture, Norway, 1999 |
| | AH187 | Emetic outbreak, United Kingdom, 1972 |
| | ATCC 10987 | Study on cheese spoilage, Canada |
| | m1550 | Uncooked chicken, Brazil |
| | 172560W | Burn wound |
| | R309803 | Septicemia, United Kingdom |
| | Rock3-42 | Soil, Rockville Maryland |
| | AH1273 | Human blood, Iceland |
| *B. thuringiensis* | Serovar konkukian str. 97-27 | Infected wound, French soldier, Yugoslavia, 1995 |
| | BGSC 4Y1 | Soil, Japan |
| | T13001 | Lepidoptera, Pakistan |
| | ATCC 10792 | Mediterranean flour moth |
| | IBL 200 | Human isolate, israeliensis-like serovar |
| | BGSC 4CC1 | Grain field, Pakistan |

Amino acid sequence comparisons for Proteins 500-515 (SEQ ID NO:1-16) are shown in FIG. 5. In general, if a protein is encoded by the organism, the protein has 99-100% percent identity across strains of *B. anthracis*. Conservation of the amino acid sequence is sometimes reduced when comparing *B. anthracis* with *B. cereus* or *B. thuringiensis*. This is most apparent for proteins 509 and 512, although the percent identity is at least 73%.

To further evaluate IRP conservation across multiple species, a cross-species alignment was performed for full-length Protein 500 (SEQ ID NO:1), Protein 509 (SEQ ID NO:10), and Protein 510 (SEQ ID NO:11) using Clustal Omega (v1.2.0, European Molecular Biology Laboratory-European Bioinformatics Institute) using one strain from each species that expressed all three proteins. These three proteinss were selected because they represent three types of IRPs that appear to have different functions. Protein 500 is a siderophore receptor. Protein 509 is BmpA, a lipoprotein and member of the bmp gene family that is not well-characterized in *B. anthracis*. Protein 510 is S-layer protein, an adhesin and virulence factor. The strains used for comparison were *B. anthracis* Sterne, *B. cereus* ATCC 10987, and *B. thuringiensis* BGSC 4Y1. The alignments demonstrate that these three polypeptides share substantial stretches of amino acid identity across each of the three *Bacillus* species (FIG. 6, FIG. 7, and FIG. 8). This is apparent despite their functional diversity, which includes siderophore receptors (Protein 500) that are known to be highly conserved, BmpA (Protein 509), for which little information is available, and S-layer protein (Protein 510), an adhesin.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and Ref-Seq) cited herein are incorporated by reference. If any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

EXEMPLARY EMBODIMENTS

Embodiment 1

A composition comprising:
at least two polypeptides natively expressed by a *Bacillus* spp. at greater level when the *Bacillus* spp. is grown in culture medium comprising an iron chelator compared to when the *Bacillus* spp. is grown in culture medium without the iron chelator; and
an adjuvant.

Embodiment 2

The composition of Embodiment 1 further comprising:
a polypeptide natively expressed by a *Bacillus* spp. having a molecular weight of 17 kDa as determined by SDS-PAGE and at least 90% amino acid similarity to the amino acid sequence of SEQ ID NO:12; or
a polypeptide natively expressed by a *Bacillus* spp. having a molecular weight of 100 kDa as determined by SDS-PAGE and at least 90% amino acid similarity to the amino acid sequence of SEQ ID NO:13.

Embodiment 3

The composition of Embodiment 1 wherein the at least two polypeptides comprise two or more of:
a first polypeptide natively expressed by a *Bacillus* spp. having a molecular weight of 36 kDa as determined by SDS-PAGE and at least 90% amino acid similarity to the amino acid sequence of SEQ ID NO:1;
a second polypeptide natively expressed by a *Bacillus* spp. having a molecular weight of 35 kDa as determined by SDS-PAGE and at least 90% amino acid similarity to the amino acid sequence of SEQ ID NO:2;
a third polypeptide natively expressed by a *Bacillus* spp. having a molecular weight of 35 kDa as determined by SDS-PAGE and at least 90% amino acid similarity to the amino acid sequence of SEQ ID NO:3;
a fourth polypeptide natively expressed by a *Bacillus* spp. having a molecular weight of 39 kDa as determined by SDS-PAGE and at least 90% amino acid similarity to the amino acid sequence of SEQ ID NO:4;
a fifth polypeptide natively expressed by a *Bacillus* spp. having a molecular weight of 35 kDa as determined by SDS-PAGE and at least 90% amino acid similarity to the amino acid sequence of SEQ ID NO:5;
a sixth polypeptide natively expressed by a *Bacillus* spp. having a molecular weight of 36 kDa as determined by SDS-PAGE and at least 90% amino acid similarity to the amino acid sequence of SEQ ID NO:6;
a seventh polypeptide natively expressed by a *Bacillus* spp. having a molecular weight of 62 kDa as determined by SDS-PAGE and at least 90% amino acid similarity to the amino acid sequence of SEQ ID NO:7;
an eighth polypeptide natively expressed by a *Bacillus* spp. having a molecular weight of 32 kDa as determined by SDS-PAGE and at least 90% amino acid similarity to the amino acid sequence of SEQ ID NO:8;
a ninth polypeptide natively expressed by a *Bacillus* spp. having a molecular weight of 36 kDa as determined by SDS-PAGE and at least 90% amino acid similarity to the amino acid sequence of SEQ ID NO:9;
a tenth polypeptide natively expressed by a *Bacillus* spp. having a molecular weight of 38 kDa as determined by SDS-PAGE and at least 90% amino acid similarity to the amino acid sequence of SEQ ID NO:10;
an eleventh polypeptide natively expressed by a *Bacillus* spp. having a molecular weight of 39 kDa as determined by SDS-PAGE and at least 90% amino acid similarity to the amino acid sequence of SEQ ID NO:11;
a twelfth polypeptide natively expressed by a *Bacillus* spp. having a molecular weight of 36 kDa as determined by SDS-PAGE and at least 90% amino acid similarity to the amino acid sequence of SEQ ID NO:14;
a thirteenth polypeptide natively expressed by a *Bacillus* spp. having a molecular weight of 36 kDa as determined by SDS-PAGE and at least 90% amino acid similarity to the amino acid sequence of SEQ ID NO:15; or
a fourteenth polypeptide natively expressed by a *Bacillus* spp. having a molecular weight of 35 kDa as determined by SDS-PAGE and at least 90% amino acid similarity to the amino acid sequence of SEQ ID NO:16.

Embodiment 4

The composition of Embodiment 3 comprising:
the first polypeptide;
the second polypeptide;
the third polypeptide;
the fifth polypeptide;
the sixth polypeptide;
the eleventh polypeptide; and
the twelfth polypeptide.

Embodiment 5

The composition of Embodiment 3 or Embodiment 4 further comprising:
a fifteenth polypeptide natively expressed by a *Bacillus* spp. having a molecular weight of 17 kDa as determined by SDS-PAGE and at least 90% amino acid similarity to the amino acid sequence of SEQ ID NO:12; or
a sixteenth polypeptide natively expressed by a *Bacillus* spp. having a molecular weight of 100 kDa as determined by SDS-PAGE and at least 90% amino acid similarity to the amino acid sequence of SEQ ID NO:13.

Embodiment 6

The composition of any preceding Embodiment wherein the composition protects against challenge by *Bacillus anthracis*.

Embodiment 7

A method for treating an infection in a subject, the method comprising:
administering an effective amount of a composition to a subject having or at risk of having an infection caused by a *Bacillus* spp., wherein the composition comprises at least two polypeptides natively expressed by a *Bacillus* spp. at greater level when the *Bacillus* spp. is grown in culture medium comprising an iron chelator compared to when the *Bacillus* spp. is grown in culture medium without the iron chelator.

Embodiment 8

The method of Embodiment 7 wherein the at least two polypeptides comprise two or more of:
a first polypeptide natively expressed by a *Bacillus* spp. having a molecular weight of 36 kDa as determined by SDS-PAGE and at least 90% amino acid similarity to the amino acid sequence of SEQ ID NO:1;
a second polypeptide natively expressed by a *Bacillus* spp. having a molecular weight of 35 kDa as determined by SDS-PAGE and at least 90% amino acid similarity to the amino acid sequence of SEQ ID NO:2;
a third polypeptide natively expressed by a *Bacillus* spp. having a molecular weight of 35 kDa as determined by SDS-PAGE and at least 90% amino acid similarity to the amino acid sequence of SEQ ID NO:3;
a fourth polypeptide natively expressed by a *Bacillus* spp. having a molecular weight of 39 kDa as determined by SDS-PAGE and at least 90% amino acid similarity to the amino acid sequence of SEQ ID NO:4;
a fifth polypeptide natively expressed by a *Bacillus* spp. having a molecular weight of 35 kDa as determined by SDS-PAGE and at least 90% amino acid similarity to the amino acid sequence of SEQ ID NO:5;
a sixth polypeptide natively expressed by a *Bacillus* spp. having a molecular weight of 36 kDa as determined by SDS-PAGE and at least 90% amino acid similarity to the amino acid sequence of SEQ ID NO:6;

a seventh polypeptide natively expressed by a *Bacillus* spp. having a molecular weight of 62 kDa as determined by SDS-PAGE and at least 90% amino acid similarity to the amino acid sequence of SEQ ID NO:7;

an eighth polypeptide natively expressed by a *Bacillus* spp. having a molecular weight of 32 kDa as determined by SDS-PAGE and at least 90% amino acid similarity to the amino acid sequence of SEQ ID NO:8;

a ninth polypeptide natively expressed by a *Bacillus* spp. having a molecular weight of 36 kDa as determined by SDS-PAGE and at least 90% amino acid similarity to the amino acid sequence of SEQ ID NO:9;

a tenth polypeptide natively expressed by a *Bacillus* spp. having a molecular weight of 38 kDa as determined by SDS-PAGE and at least 90% amino acid similarity to the amino acid sequence of SEQ ID NO:10;

an eleventh polypeptide natively expressed by a *Bacillus* spp. having a molecular weight of 39 kDa as determined by SDS-PAGE and at least 90% amino acid similarity to the amino acid sequence of SEQ ID NO:11;

a twelfth polypeptide natively expressed by a *Bacillus* spp. having a molecular weight of 36 kDa as determined by SDS-PAGE and at least 90% amino acid similarity to the amino acid sequence of SEQ ID NO:14;

a thirteenth polypeptide natively expressed by a *Bacillus* spp. having a molecular weight of 36 kDa as determined by SDS-PAGE and at least 90% amino acid similarity to the amino acid sequence of SEQ ID NO:15; or a fourteenth polypeptide natively expressed by a *Bacillus* spp. having a molecular weight of 35 kDa as determined by SDS-PAGE and at least 90% amino acid similarity to the amino acid sequence of SEQ ID NO:16.

Embodiment 9

The method of Embodiment 8 wherein the composition comprises:
the first polypeptide;
the second polypeptide;
the third polypeptide;
the fifth polypeptide;
the sixth polypeptide;
the eleventh polypeptide; and
the twelfth polypeptide.

Embodiment 10

The method of Embodiment 8 or Embodiment 9 wherein the composition further comprises:
a fifteenth polypeptide natively expressed by a *Bacillus* spp. having a molecular weight of 17 kDa as determined by SDS-PAGE and at least 90% amino acid similarity to the amino acid sequence of SEQ ID NO:12; or
a sixteenth polypeptide natively expressed by a *Bacillus* spp. having a molecular weight of 100 kDa as determined by SDS-PAGE and at least 90% amino acid similarity to the amino acid sequence of SEQ ID NO:13.

Embodiment 11

A method for treating a symptom in a subject, the method comprising:
administering an effective amount of a composition to a subject having or at risk of having an infection caused by a *Bacillus* spp., wherein the composition comprises at least two polypeptides natively expressed by a *Bacillus* spp. at greater level when the *Bacillus* spp. is grown in culture medium comprising an iron chelator compared to when the *Bacillus* spp. is grown in culture medium without the iron chelator.

Embodiment 12

The method of Embodiment 11 wherein the at least two polypeptides comprise two or more of:
a first polypeptide natively expressed by a *Bacillus* spp. having a molecular weight of 36 kDa as determined by SDS-PAGE and at least 90% amino acid similarity to the amino acid sequence of SEQ ID NO:1;

a second polypeptide natively expressed by a *Bacillus* spp. having a molecular weight of 35 kDa as determined by SDS-PAGE and at least 90% amino acid similarity to the amino acid sequence of SEQ ID NO:2;

a third polypeptide natively expressed by a *Bacillus* spp. having a molecular weight of 35 kDa as determined by SDS-PAGE and at least 90% amino acid similarity to the amino acid sequence of SEQ ID NO:3;

a fourth polypeptide natively expressed by a *Bacillus* spp. having a molecular weight of 39 kDa as determined by SDS-PAGE and at least 90% amino acid similarity to the amino acid sequence of SEQ ID NO:4;

a fifth polypeptide natively expressed by a *Bacillus* spp. having a molecular weight of 35 kDa as determined by SDS-PAGE and at least 90% amino acid similarity to the amino acid sequence of SEQ ID NO:5;

a sixth polypeptide natively expressed by a *Bacillus* spp. having a molecular weight of 36 kDa as determined by SDS-PAGE and at least 90% amino acid similarity to the amino acid sequence of SEQ ID NO:6;

a seventh polypeptide natively expressed by a *Bacillus* spp. having a molecular weight of 62 kDa as determined by SDS-PAGE and at least 90% amino acid similarity to the amino acid sequence of SEQ ID NO:7;

an eighth polypeptide natively expressed by a *Bacillus* spp. having a molecular weight of 32 kDa as determined by SDS-PAGE and at least 90% amino acid similarity to the amino acid sequence of SEQ ID NO:8;

a ninth polypeptide natively expressed by a *Bacillus* spp. having a molecular weight of 36 kDa as determined by SDS-PAGE and at least 90% amino acid similarity to the amino acid sequence of SEQ ID NO:9;

a tenth polypeptide natively expressed by a *Bacillus* spp. having a molecular weight of 38 kDa as determined by SDS-PAGE and at least 90% amino acid similarity to the amino acid sequence of SEQ ID NO:10;

an eleventh polypeptide natively expressed by a *Bacillus* spp. having a molecular weight of 39 kDa as determined by SDS-PAGE and at least 90% amino acid similarity to the amino acid sequence of SEQ ID NO:11;

a twelfth polypeptide natively expressed by a *Bacillus* spp. having a molecular weight of 36 kDa as determined by SDS-PAGE and at least 90% amino acid similarity to the amino acid sequence of SEQ ID NO:14;

a thirteenth polypeptide natively expressed by a *Bacillus* spp. having a molecular weight of 36 kDa as determined by SDS-PAGE and at least 90% amino acid similarity to the amino acid sequence of SEQ ID NO:15; or a fourteenth polypeptide natively expressed by a *Bacillus* spp. having a molecular weight of 35 kDa as determined by SDS-PAGE and at least 90% amino acid similarity to the amino acid sequence of SEQ ID NO:16.

Embodiment 13

The method of Embodiment 12 wherein the composition comprises:
the first polypeptide;
the second polypeptide;

the third polypeptide;
the fifth polypeptide;
the sixth polypeptide;
the eleventh polypeptide; and
the twelfth polypeptide.

Embodiment 14

The method of Embodiment 12 or Embodiment 13 wherein the composition further comprises:
a fifteenth polypeptide natively expressed by a *Bacillus* spp. having a molecular weight of 17 kDa as determined by SDS-PAGE and at least 90% amino acid similarity to the amino acid sequence of SEQ ID NO:12; or
a sixteenth polypeptide natively expressed by a *Bacillus* spp. having a molecular weight of 100 kDa as determined by SDS-PAGE and at least 90% amino acid similarity to the amino acid sequence of SEQ ID NO:13.

Embodiment 15

A method for decreasing colonization in a subject, the method comprising:
administering an effective amount of a composition to a subject colonized by a *Bacillus* spp., wherein the composition comprises at least two polypeptides natively expressed by a *Bacillus* spp. at greater level when the *Bacillus* spp. is grown in culture medium comprising an iron chelator compared to when the *Bacillus* spp. is grown in culture medium without the iron chelator.

Embodiment 16

The method of Embodiment 15 wherein the at least two polypeptides comprise two or more of:
a first polypeptide natively expressed by a *Bacillus* spp. having a molecular weight of 36 kDa as determined by SDS-PAGE and at least 90% amino acid similarity to the amino acid sequence of SEQ ID NO:1;
a second polypeptide natively expressed by a *Bacillus* spp. having a molecular weight of 35 kDa as determined by SDS-PAGE and at least 90% amino acid similarity to the amino acid sequence of SEQ ID NO:2;
a third polypeptide natively expressed by a *Bacillus* spp. having a molecular weight of 35 kDa as determined by SDS-PAGE and at least 90% amino acid similarity to the amino acid sequence of SEQ ID NO:3;
a fourth polypeptide natively expressed by a *Bacillus* spp. having a molecular weight of 39 kDa as determined by SDS-PAGE and at least 90% amino acid similarity to the amino acid sequence of SEQ ID NO:4;
a fifth polypeptide natively expressed by a *Bacillus* spp. having a molecular weight of 35 kDa as determined by SDS-PAGE and at least 90% amino acid similarity to the amino acid sequence of SEQ ID NO:5;
a sixth polypeptide natively expressed by a *Bacillus* spp. having a molecular weight of 36 kDa as determined by SDS-PAGE and at least 90% amino acid similarity to the amino acid sequence of SEQ ID NO:6;
a seventh polypeptide natively expressed by a *Bacillus* spp. having a molecular weight of 62 kDa as determined by SDS-PAGE and at least 90% amino acid similarity to the amino acid sequence of SEQ ID NO:7;
an eighth polypeptide natively expressed by a *Bacillus* spp. having a molecular weight of 32 kDa as determined by SDS-PAGE and at least 90% amino acid similarity to the amino acid sequence of SEQ ID NO:8;
a ninth polypeptide natively expressed by a *Bacillus* spp. having a molecular weight of 36 kDa as determined by SDS-PAGE and at least 90% amino acid similarity to the amino acid sequence of SEQ ID NO:9;
a tenth polypeptide natively expressed by a *Bacillus* spp. having a molecular weight of 38 kDa as determined by SDS-PAGE and at least 90% amino acid similarity to the amino acid sequence of SEQ ID NO:10;
an eleventh polypeptide natively expressed by a *Bacillus* spp. having a molecular weight of 39 kDa as determined by SDS-PAGE and at least 90% amino acid similarity to the amino acid sequence of SEQ ID NO:11;
a twelfth polypeptide natively expressed by a *Bacillus* spp. having a molecular weight of 36 kDa as determined by SDS-PAGE and at least 90% amino acid similarity to the amino acid sequence of SEQ ID NO:14;
a thirteenth polypeptide natively expressed by a *Bacillus* spp. having a molecular weight of 36 kDa as determined by SDS-PAGE and at least 90% amino acid similarity to the amino acid sequence of SEQ ID NO:15; or
a fourteenth polypeptide natively expressed by a *Bacillus* spp. having a molecular weight of 35 kDa as determined by SDS-PAGE and at least 90% amino acid similarity to the amino acid sequence of SEQ ID NO:16.

Embodiment 17

The method of Embodiment 16 wherein the composition comprises:
the first polypeptide;
the second polypeptide;
the third polypeptide;
the fifth polypeptide;
the sixth polypeptide;
the eleventh polypeptide; and
the twelfth polypeptide.

Embodiment 18

The method of Embodiment 16 or Embodiment 17 wherein the composition further comprises:
a fifteenth polypeptide natively expressed by a *Bacillus* spp. having a molecular weight of 17 kDa as determined by SDS-PAGE and at least 90% amino acid similarity to the amino acid sequence of SEQ ID NO:12; or
a sixteenth polypeptide natively expressed by a *Bacillus* spp. having a molecular weight of 100 kDa as determined by SDS-PAGE and at least 90% amino acid similarity to the amino acid sequence of SEQ ID NO:13.

Embodiment 19

A method for treating an infection in a subject, the method comprising:
administering an effective amount of a composition to a subject having or at risk of having an infection caused by a *Bacillus* spp., wherein the composition comprises:
antibody that specifically binds at least two polypeptides natively expressed by a *Bacillus* spp. at greater level when the *Bacillus* spp. is grown in culture medium comprising an iron chelator compared to when the *Bacillus* spp. is grown in culture medium without the iron chelator.

Embodiment 20

The method of Embodiment 19 wherein the at least two polypeptides comprise two or more of:
a first polypeptide natively expressed by a *Bacillus* spp. having a molecular weight of 36 kDa as determined by SDS-PAGE and at least 90% amino acid similarity to the amino acid sequence of SEQ ID NO:1;

a second polypeptide natively expressed by a *Bacillus* spp. having a molecular weight of 35 kDa as determined by SDS-PAGE and at least 90% amino acid similarity to the amino acid sequence of SEQ ID NO:2;

a third polypeptide natively expressed by a *Bacillus* spp. having a molecular weight of 35 kDa as determined by SDS-PAGE and at least 90% amino acid similarity to the amino acid sequence of SEQ ID NO:3;

a fourth polypeptide natively expressed by a *Bacillus* spp. having a molecular weight of 39 kDa as determined by SDS-PAGE and at least 90% amino acid similarity to the amino acid sequence of SEQ ID NO:4;

a fifth polypeptide natively expressed by a *Bacillus* spp. having a molecular weight of 35 kDa as determined by SDS-PAGE and at least 90% amino acid similarity to the amino acid sequence of SEQ ID NO:5;

a sixth polypeptide natively expressed by a *Bacillus* spp. having a molecular weight of 36 kDa as determined by SDS-PAGE and at least 90% amino acid similarity to the amino acid sequence of SEQ ID NO:6;

a seventh polypeptide natively expressed by a *Bacillus* spp. having a molecular weight of 62 kDa as determined by SDS-PAGE and at least 90% amino acid similarity to the amino acid sequence of SEQ ID NO:7;

an eighth polypeptide natively expressed by a *Bacillus* spp. having a molecular weight of 32 kDa as determined by SDS-PAGE and at least 90% amino acid similarity to the amino acid sequence of SEQ ID NO:8;

a ninth polypeptide natively expressed by a *Bacillus* spp. having a molecular weight of 36 kDa as determined by SDS-PAGE and at least 90% amino acid similarity to the amino acid sequence of SEQ ID NO:9;

a tenth polypeptide natively expressed by a *Bacillus* spp. having a molecular weight of 38 kDa as determined by SDS-PAGE and at least 90% amino acid similarity to the amino acid sequence of SEQ ID NO:10;

an eleventh polypeptide natively expressed by a *Bacillus* spp. having a molecular weight of 39 kDa as determined by SDS-PAGE and at least 90% amino acid similarity to the amino acid sequence of SEQ ID NO:11;

a twelfth polypeptide natively expressed by a *Bacillus* spp. having a molecular weight of 36 kDa as determined by SDS-PAGE and at least 90% amino acid similarity to the amino acid sequence of SEQ ID NO:14;

a thirteenth polypeptide natively expressed by a *Bacillus* spp. having a molecular weight of 36 kDa as determined by SDS-PAGE and at least 90% amino acid similarity to the amino acid sequence of SEQ ID NO:15; or a fourteenth polypeptide natively expressed by a *Bacillus* spp. having a molecular weight of 35 kDa as determined by SDS-PAGE and at least 90% amino acid similarity to the amino acid sequence of SEQ ID NO:16.

Embodiment 21

The method of Embodiment 20 wherein the composition comprises:
the first polypeptide;
the second polypeptide;
the third polypeptide;
the fifth polypeptide;
the sixth polypeptide;
the eleventh polypeptide; and
the twelfth polypeptide.

Embodiment 22

The method of Embodiment 20 or Embodiment 21 wherein the composition further comprises:
a fifteenth polypeptide natively expressed by a *Bacillus* spp. having a molecular weight of 17 kDa as determined by SDS-PAGE and at least 90% amino acid similarity to the amino acid sequence of SEQ ID NO:12; or a sixteenth polypeptide natively expressed by a *Bacillus* spp. having a molecular weight of 100 kDa as determined by SDS-PAGE and at least 90% amino acid similarity to the amino acid sequence of SEQ ID NO:13.

Embodiment 23

A method for treating a symptom in a subject comprising:
administering an effective amount of a composition to a subject having an infection caused by a *Bacillus* spp., wherein the composition comprises:
antibody that specifically binds at least two polypeptides natively expressed by a *Bacillus* spp. at greater level when the *Bacillus* spp. is grown in culture medium comprising an iron chelator compared to when the *Bacillus* spp. is grown in culture medium without the iron chelator.

Embodiment 24

The method of Embodiment 23 wherein the at least two polypeptides comprise two or more of:
a first polypeptide natively expressed by a *Bacillus* spp. having a molecular weight of 36 kDa as determined by SDS-PAGE and at least 90% amino acid similarity to the amino acid sequence of SEQ ID NO:1;

a second polypeptide natively expressed by a *Bacillus* spp. having a molecular weight of 35 kDa as determined by SDS-PAGE and at least 90% amino acid similarity to the amino acid sequence of SEQ ID NO:2;

a third polypeptide natively expressed by a *Bacillus* spp. having a molecular weight of 35 kDa as determined by SDS-PAGE and at least 90% amino acid similarity to the amino acid sequence of SEQ ID NO:3;

a fourth polypeptide natively expressed by a *Bacillus* spp. having a molecular weight of 39 kDa as determined by SDS-PAGE and at least 90% amino acid similarity to the amino acid sequence of SEQ ID NO:4;

a fifth polypeptide natively expressed by a *Bacillus* spp. having a molecular weight of 35 kDa as determined by SDS-PAGE and at least 90% amino acid similarity to the amino acid sequence of SEQ ID NO:5;

a sixth polypeptide natively expressed by a *Bacillus* spp. having a molecular weight of 36 kDa as determined by SDS-PAGE and at least 90% amino acid similarity to the amino acid sequence of SEQ ID NO:6;

a seventh polypeptide natively expressed by a *Bacillus* spp. having a molecular weight of 62 kDa as determined by SDS-PAGE and at least 90% amino acid similarity to the amino acid sequence of SEQ ID NO:7;

an eighth polypeptide natively expressed by a *Bacillus* spp. having a molecular weight of 32 kDa as determined by SDS-PAGE and at least 90% amino acid similarity to the amino acid sequence of SEQ ID NO:8;

a ninth polypeptide natively expressed by a *Bacillus* spp. having a molecular weight of 36 kDa as determined by SDS-PAGE and at least 90% amino acid similarity to the amino acid sequence of SEQ ID NO:9;

a tenth polypeptide natively expressed by a *Bacillus* spp. having a molecular weight of 38 kDa as determined by SDS-PAGE and at least 90% amino acid similarity to the amino acid sequence of SEQ ID NO:10;

an eleventh polypeptide natively expressed by a *Bacillus* spp. having a molecular weight of 39 kDa as determined by SDS-PAGE and at least 90% amino acid similarity to the amino acid sequence of SEQ ID NO:11;

a twelfth polypeptide natively expressed by a *Bacillus* spp. having a molecular weight of 36 kDa as determined by SDS-PAGE and at least 90% amino acid similarity to the amino acid sequence of SEQ ID NO:14;

a thirteenth polypeptide natively expressed by a *Bacillus* spp. having a molecular weight of 36 kDa as determined by SDS-PAGE and at least 90% amino acid similarity to the amino acid sequence of SEQ ID NO:15; or a fourteenth polypeptide natively expressed by a *Bacillus* spp. having a molecular weight of 35 kDa as determined by SDS-PAGE and at least 90% amino acid similarity to the amino acid sequence of SEQ ID NO:16.

Embodiment 25

The method of Embodiment 24 wherein the composition comprises:
the first polypeptide;
the second polypeptide;
the third polypeptide;
the fifth polypeptide;
the sixth polypeptide;
the eleventh polypeptide; and
the twelfth polypeptide.

Embodiment 26

The method of Embodiment 24 or Embodiment 25 wherein the composition further comprises:
a fifteenth polypeptide natively expressed by a *Bacillus* spp. having a molecular weight of 17 kDa as determined by SDS-PAGE and at least 90% amino acid similarity to the amino acid sequence of SEQ ID NO:12; or
a sixteenth polypeptide natively expressed by a *Bacillus* spp. having a molecular weight of 100 kDa as determined by SDS-PAGE and at least 90% amino acid similarity to the amino acid sequence of SEQ ID NO:13.

Embodiment 27

A method for treating an infection in a subject, the method comprising:
administering an effective amount of a composition to a subject having or at risk of having an infection caused by a *Bacillus* spp., wherein the composition comprises:
antibody that specifically binds at least two polypeptides natively expressed by a *Bacillus* spp. at greater level when the *Bacillus* spp. is grown in culture medium comprising an iron chelator compared to when the *Bacillus* spp. is grown in culture medium without the iron chelator.

Embodiment 28

The method of Embodiment 27 wherein the at least two polypeptides comprise two or more of:
a first polypeptide natively expressed by a *Bacillus* spp. having a molecular weight of 36 kDa as determined by SDS-PAGE and at least 90% amino acid similarity to the amino acid sequence of SEQ ID NO:1;

a second polypeptide natively expressed by a *Bacillus* spp. having a molecular weight of 35 kDa as determined by SDS-PAGE and at least 90% amino acid similarity to the amino acid sequence of SEQ ID NO:2;

a third polypeptide natively expressed by a *Bacillus* spp. having a molecular weight of 35 kDa as determined by SDS-PAGE and at least 90% amino acid similarity to the amino acid sequence of SEQ ID NO:3;

a fourth polypeptide natively expressed by a *Bacillus* spp. having a molecular weight of 39 kDa as determined by SDS-PAGE and at least 90% amino acid similarity to the amino acid sequence of SEQ ID NO:4;

a fifth polypeptide natively expressed by a *Bacillus* spp. having a molecular weight of 35 kDa as determined by SDS-PAGE and at least 90% amino acid similarity to the amino acid sequence of SEQ ID NO:5;

a sixth polypeptide natively expressed by a *Bacillus* spp. having a molecular weight of 36 kDa as determined by SDS-PAGE and at least 90% amino acid similarity to the amino acid sequence of SEQ ID NO:6;

a seventh polypeptide natively expressed by a *Bacillus* spp. having a molecular weight of 62 kDa as determined by SDS-PAGE and at least 90% amino acid similarity to the amino acid sequence of SEQ ID NO:7;

an eighth polypeptide natively expressed by a *Bacillus* spp. having a molecular weight of 32 kDa as determined by SDS-PAGE and at least 90% amino acid similarity to the amino acid sequence of SEQ ID NO:8;

a ninth polypeptide natively expressed by a *Bacillus* spp. having a molecular weight of 36 kDa as determined by SDS-PAGE and at least 90% amino acid similarity to the amino acid sequence of SEQ ID NO:9;

a tenth polypeptide natively expressed by a *Bacillus* spp. having a molecular weight of 38 kDa as determined by SDS-PAGE and at least 90% amino acid similarity to the amino acid sequence of SEQ ID NO:10;

an eleventh polypeptide natively expressed by a *Bacillus* spp. having a molecular weight of 39 kDa as determined by SDS-PAGE and at least 90% amino acid similarity to the amino acid sequence of SEQ ID NO:11;

a twelfth polypeptide natively expressed by a *Bacillus* spp. having a molecular weight of 36 kDa as determined by SDS-PAGE and at least 90% amino acid similarity to the amino acid sequence of SEQ ID NO:14;

a thirteenth polypeptide natively expressed by a *Bacillus* spp. having a molecular weight of 36 kDa as determined by SDS-PAGE and at least 90% amino acid similarity to the amino acid sequence of SEQ ID NO:15; or a fourteenth polypeptide natively expressed by a *Bacillus* spp. having a molecular weight of 35 kDa as determined by SDS-PAGE and at least 90% amino acid similarity to the amino acid sequence of SEQ ID NO:16.

Embodiment 29

The method of Embodiment 28 wherein the composition comprises:
the first polypeptide;
the second polypeptide;
the third polypeptide;
the fifth polypeptide;
the sixth polypeptide;
the eleventh polypeptide; and
the twelfth polypeptide.

Embodiment 30

The method of Embodiment 28 or Embodiment 29 wherein the composition further comprises:
a fifteenth polypeptide natively expressed by a *Bacillus* spp. having a molecular weight of 17 kDa as determined by SDS-PAGE and at least 90% amino acid similarity to the amino acid sequence of SEQ ID NO:12; or a sixteenth polypeptide natively expressed by a *Bacillus* spp. having a molecular weight of 100 kDa as determined by SDS-PAGE and at least 90% amino acid similarity to the amino acid sequence of SEQ ID NO:13.

Embodiment 31

A kit for detecting antibody that specifically binds a polypeptide, comprising in separate containers:

an isolated polypeptide natively expressed by a *Bacillus* spp. at greater level when the *Bacillus* spp. is grown in culture medium comprising an iron chelator compared to when the *Bacillus* spp. is grown in culture medium without the iron chelator; and a reagent that detects an antibody that specifically binds the polypeptide.

Embodiment 32

The kit of Embodiment 31 wherein the polypeptide comprises:

a first polypeptide natively expressed by a *Bacillus* spp. having a molecular weight of 36 kDa as determined by SDS-PAGE and at least 90% amino acid similarity to the amino acid sequence of SEQ ID NO:1;

a second polypeptide natively expressed by a *Bacillus* spp. having a molecular weight of 35 kDa as determined by SDS-PAGE and at least 90% amino acid similarity to the amino acid sequence of SEQ ID NO:2;

a third polypeptide natively expressed by a *Bacillus* spp. having a molecular weight of 35 kDa as determined by SDS-PAGE and at least 90% amino acid similarity to the amino acid sequence of SEQ ID NO:3;

a fourth polypeptide natively expressed by a *Bacillus* spp. having a molecular weight of 39 kDa as determined by SDS-PAGE and at least 90% amino acid similarity to the amino acid sequence of SEQ ID NO:4;

a fifth polypeptide natively expressed by a *Bacillus* spp. having a molecular weight of 35 kDa as determined by SDS-PAGE and at least 90% amino acid similarity to the amino acid sequence of SEQ ID NO:5;

a sixth polypeptide natively expressed by a *Bacillus* spp. having a molecular weight of 36 kDa as determined by SDS-PAGE and at least 90% amino acid similarity to the amino acid sequence of SEQ ID NO:6;

a seventh polypeptide natively expressed by a *Bacillus* spp. having a molecular weight of 62 kDa as determined by SDS-PAGE and at least 90% amino acid similarity to the amino acid sequence of SEQ ID NO:7;

an eighth polypeptide natively expressed by a *Bacillus* spp. having a molecular weight of 32 kDa as determined by SDS-PAGE and at least 90% amino acid similarity to the amino acid sequence of SEQ ID NO:8;

a ninth polypeptide natively expressed by a *Bacillus* spp. having a molecular weight of 36 kDa as determined by SDS-PAGE and at least 90% amino acid similarity to the amino acid sequence of SEQ ID NO:9;

a tenth polypeptide natively expressed by a *Bacillus* spp. having a molecular weight of 38 kDa as determined by SDS-PAGE and at least 90% amino acid similarity to the amino acid sequence of SEQ ID NO:10;

an eleventh polypeptide natively expressed by a *Bacillus* spp. having a molecular weight of 39 kDa as determined by SDS-PAGE and at least 90% amino acid similarity to the amino acid sequence of SEQ ID NO:11;

a twelfth polypeptide natively expressed by a *Bacillus* spp. having a molecular weight of 36 kDa as determined by SDS-PAGE and at least 90% amino acid similarity to the amino acid sequence of SEQ ID NO:14;

a thirteenth polypeptide natively expressed by a *Bacillus* spp. having a molecular weight of 36 kDa as determined by SDS-PAGE and at least 90% amino acid similarity to the amino acid sequence of SEQ ID NO:15; or a fourteenth polypeptide natively expressed by a *Bacillus* spp. having a molecular weight of 35 kDa as determined by SDS-PAGE and at least 90% amino acid similarity to the amino acid sequence of SEQ ID NO:16.

Embodiment 33

A kit for detecting a polypeptide, comprising in separate containers:

antibody that specifically binds a polypeptide natively expressed by a *Bacillus* spp. at greater level when the *Bacillus* spp. is grown in culture medium comprising an iron chelator compared to when the *Bacillus* spp. is grown in culture medium without the iron chelator; and a second reagent that specifically binds the polypeptide.

Embodiment 34

The kit of Embodiment 33 wherein the polypeptide comprises:

a first polypeptide natively expressed by a *Bacillus* spp. having a molecular weight of 36 kDa as determined by SDS-PAGE and at least 90% amino acid similarity to the amino acid sequence of SEQ ID NO:1;

a second polypeptide natively expressed by a *Bacillus* spp. having a molecular weight of 35 kDa as determined by SDS-PAGE and at least 90% amino acid similarity to the amino acid sequence of SEQ ID NO:2;

a third polypeptide natively expressed by a *Bacillus* spp. having a molecular weight of 35 kDa as determined by SDS-PAGE and at least 90% amino acid similarity to the amino acid sequence of SEQ ID NO:3;

a fourth polypeptide natively expressed by a *Bacillus* spp. having a molecular weight of 39 kDa as determined by SDS-PAGE and at least 90% amino acid similarity to the amino acid sequence of SEQ ID NO:4;

a fifth polypeptide natively expressed by a *Bacillus* spp. having a molecular weight of 35 kDa as determined by SDS-PAGE and at least 90% amino acid similarity to the amino acid sequence of SEQ ID NO:5;

a sixth polypeptide natively expressed by a *Bacillus* spp. having a molecular weight of 36 kDa as determined by SDS-PAGE and at least 90% amino acid similarity to the amino acid sequence of SEQ ID NO:6;

a seventh polypeptide natively expressed by a *Bacillus* spp. having a molecular weight of 62 kDa as determined by SDS-PAGE and at least 90% amino acid similarity to the amino acid sequence of SEQ ID NO:7;

an eighth polypeptide natively expressed by a *Bacillus* spp. having a molecular weight of 32 kDa as determined by SDS-PAGE and at least 90% amino acid similarity to the amino acid sequence of SEQ ID NO:8;

a ninth polypeptide natively expressed by a *Bacillus* spp. having a molecular weight of 36 kDa as determined by SDS-PAGE and at least 90% amino acid similarity to the amino acid sequence of SEQ ID NO:9;

a tenth polypeptide natively expressed by a *Bacillus* spp. having a molecular weight of 38 kDa as determined by SDS-PAGE and at least 90% amino acid similarity to the amino acid sequence of SEQ ID NO:10;

an eleventh polypeptide natively expressed by a *Bacillus* spp. having a molecular weight of 39 kDa as determined by SDS-PAGE and at least 90% amino acid similarity to the amino acid sequence of SEQ ID NO:11;

a twelfth polypeptide natively expressed by a *Bacillus* spp. having a molecular weight of 36 kDa as determined by SDS-PAGE and at least 90% amino acid similarity to the amino acid sequence of SEQ ID NO:14;

a thirteenth polypeptide natively expressed by a *Bacillus* spp. having a molecular weight of 36 kDa as determined by SDS-PAGE and at least 90% amino acid similarity to the amino acid sequence of SEQ ID NO:15; or a fourteenth polypeptide natively expressed by a *Bacillus* spp. having a molecular weight of 35 kDa as determined by SDS-PAGE and at least 90% amino acid similarity to the amino acid sequence of SEQ ID NO:16.

Embodiment 35

A composition comprising:

an isolated whole cell that comprises at least two polypeptides natively expressed by a *Bacillus* spp. at greater level when the *Bacillus* spp. is grown in culture medium comprising an iron chelator compared to when the *Bacillus* spp. is grown in culture medium without the iron chelator; and an adjuvant.

Embodiment 36

The composition of Embodiment 35 wherein the at least two polypeptides comprise two or more of:

a first polypeptide natively expressed by a *Bacillus* spp. having a molecular weight of 36 kDa as determined by SDS-PAGE and at least 90% amino acid similarity to the amino acid sequence of SEQ ID NO:1;

a second polypeptide natively expressed by a *Bacillus* spp. having a molecular weight of 35 kDa as determined by SDS-PAGE and at least 90% amino acid similarity to the amino acid sequence of SEQ ID NO:2;

a third polypeptide natively expressed by a *Bacillus* spp. having a molecular weight of 35 kDa as determined by SDS-PAGE and at least 90% amino acid similarity to the amino acid sequence of SEQ ID NO:3;

a fourth polypeptide natively expressed by a *Bacillus* spp. having a molecular weight of 39 kDa as determined by SDS-PAGE and at least 90% amino acid similarity to the amino acid sequence of SEQ ID NO:4;

a fifth polypeptide natively expressed by a *Bacillus* spp. having a molecular weight of 35 kDa as determined by SDS-PAGE and at least 90% amino acid similarity to the amino acid sequence of SEQ ID NO:5;

a sixth polypeptide natively expressed by a *Bacillus* spp. having a molecular weight of 36 kDa as determined by SDS-PAGE and at least 90% amino acid similarity to the amino acid sequence of SEQ ID NO:6;

a seventh polypeptide natively expressed by a *Bacillus* spp. having a molecular weight of 62 kDa as determined by SDS-PAGE and at least 90% amino acid similarity to the amino acid sequence of SEQ ID NO:7;

an eighth polypeptide natively expressed by a *Bacillus* spp. having a molecular weight of 32 kDa as determined by SDS-PAGE and at least 90% amino acid similarity to the amino acid sequence of SEQ ID NO:8;

a ninth polypeptide natively expressed by a *Bacillus* spp. having a molecular weight of 36 kDa as determined by SDS-PAGE and at least 90% amino acid similarity to the amino acid sequence of SEQ ID NO:9;

a tenth polypeptide natively expressed by a *Bacillus* spp. having a molecular weight of 38 kDa as determined by SDS-PAGE and at least 90% amino acid similarity to the amino acid sequence of SEQ ID NO:10;

an eleventh polypeptide natively expressed by a *Bacillus* spp. having a molecular weight of 39 kDa as determined by SDS-PAGE and at least 90% amino acid similarity to the amino acid sequence of SEQ ID NO:11;

a twelfth polypeptide natively expressed by a *Bacillus* spp. having a molecular weight of 36 kDa as determined by SDS-PAGE and at least 90% amino acid similarity to the amino acid sequence of SEQ ID NO:14;

a thirteenth polypeptide natively expressed by a *Bacillus* spp. having a molecular weight of 36 kDa as determined by SDS-PAGE and at least 90% amino acid similarity to the amino acid sequence of SEQ ID NO:15; or a fourteenth polypeptide natively expressed by a *Bacillus* spp. having a molecular weight of 35 kDa as determined by SDS-PAGE and at least 90% amino acid similarity to the amino acid sequence of SEQ ID NO:16.

Embodiment 37

The composition of Embodiment 36 wherein the isolated whole cell expresses at least:
the first polypeptide;
the second polypeptide;
the third polypeptide;
the fifth polypeptide;
the sixth polypeptide;
the eleventh polypeptide; and
the twelfth polypeptide.

Embodiment 38

The composition of Embodiment 36 or Embodiment 37 wherein the whole cell further expresses:

a fifteenth polypeptide natively expressed by a *Bacillus* spp. having a molecular weight of 17 kDa as determined by SDS-PAGE and at least 90% amino acid similarity to the amino acid sequence of SEQ ID NO:12; or a sixteenth polypeptide natively expressed by a *Bacillus* spp. having a molecular weight of 100 kDa as determined by SDS-PAGE and at least 90% amino acid similarity to the amino acid sequence of SEQ ID NO:13.

Embodiment 39

A recombinant cell that exhibits increased expression of a *Bacillus* spp. iron-regulated polypeptide compared to a wild-type control.

Embodiment 40

The recombinant cell of Embodiment 39 wherein the cell expresses the *Bacillus* spp. iron-regulated polypeptide at a detectable level after the recombinant cell is grown in culture medium that comprises iron.

Embodiment 41

A composition comprising:

isolated antibody that specifically binds to a polypeptide natively expressed by a *Bacillus* spp. at greater level when the *Bacillus* spp. is grown in culture medium comprising an iron chelator compared to when the *Bacillus* spp. is grown in culture medium without the iron chelator, wherein the polypeptide comprises:

a first polypeptide natively expressed by a *Bacillus* spp. having a molecular weight of 36 kDa as determined by SDS-PAGE and at least 90% amino acid similarity to the amino acid sequence of SEQ ID NO:1;

a second polypeptide natively expressed by a *Bacillus* spp. having a molecular weight of 35 kDa as determined by SDS-PAGE and at least 90% amino acid similarity to the amino acid sequence of SEQ ID NO:2;

a third polypeptide natively expressed by a *Bacillus* spp. having a molecular weight of 35 kDa as determined by SDS-PAGE and at least 90% amino acid similarity to the amino acid sequence of SEQ ID NO:3;

a fourth polypeptide natively expressed by a *Bacillus* spp. having a molecular weight of 39 kDa as determined by SDS-PAGE and at least 90% amino acid similarity to the amino acid sequence of SEQ ID NO:4;

a fifth polypeptide natively expressed by a *Bacillus* spp. having a molecular weight of 35 kDa as determined by SDS-PAGE and at least 90% amino acid similarity to the amino acid sequence of SEQ ID NO:5;

a sixth polypeptide natively expressed by a *Bacillus* spp. having a molecular weight of 36 kDa as determined by SDS-PAGE and at least 90% amino acid similarity to the amino acid sequence of SEQ ID NO:6;

a seventh polypeptide natively expressed by a *Bacillus* spp. having a molecular weight of 62 kDa as determined by SDS-PAGE and at least 90% amino acid similarity to the amino acid sequence of SEQ ID NO:7;

an eighth polypeptide natively expressed by a *Bacillus* spp. having a molecular weight of 32 kDa as determined by SDS-PAGE and at least 90% amino acid similarity to the amino acid sequence of SEQ ID NO:8;

a ninth polypeptide natively expressed by a *Bacillus* spp. having a molecular weight of 36 kDa as determined by SDS-PAGE and at least 90% amino acid similarity to the amino acid sequence of SEQ ID NO:9;

a tenth polypeptide natively expressed by a *Bacillus* spp. having a molecular weight of 38 kDa as determined by SDS-PAGE and at least 90% amino acid similarity to the amino acid sequence of SEQ ID NO:10;

an eleventh polypeptide natively expressed by a *Bacillus* spp. having a molecular weight of 39 kDa as determined by SDS-PAGE and at least 90% amino acid similarity to the amino acid sequence of SEQ ID NO:11;

a twelfth polypeptide natively expressed by a *Bacillus* spp. having a molecular weight of 36 kDa as determined by SDS-PAGE and at least 90% amino acid similarity to the amino acid sequence of SEQ ID NO:14;

a thirteenth polypeptide natively expressed by a *Bacillus* spp. having a molecular weight of 36 kDa as determined by SDS-PAGE and at least 90% amino acid similarity to the amino acid sequence of SEQ ID NO:15; or a fourteenth polypeptide natively expressed by a *Bacillus* spp. having a molecular weight of 35 kDa as determined by SDS-PAGE and at least 90% amino acid similarity to the amino acid sequence of SEQ ID NO:16.

Embodiment 42

The composition of Embodiment 41 wherein the composition comprises:

a first antibody that specifically binds to the first polypeptide;

a second antibody that specifically binds to the second polypeptide;

a third antibody that specifically binds to the third polypeptide;

a fourth antibody that specifically binds to the fifth polypeptide;

a fifth antibody that specifically binds to the sixth polypeptide;

a sixth antibody that specifically binds to the eleventh polypeptide; and a seventh antibody that specifically binds to the twelfth polypeptide.

Embodiment 43

The composition of Embodiment 42 wherein the composition further comprises:

an eighth antibody that specifically binds a fifteenth polypeptide natively expressed by a *Bacillus* spp. having a molecular weight of 17 kDa as determined by SDS-PAGE and at least 90% amino acid similarity to the amino acid sequence of SEQ ID NO:12; or an eighth antibody that specifically binds a sixteenth polypeptide natively expressed by a *Bacillus* spp. having a molecular weight of 100 kDa as determined by SDS-PAGE and at least 90% amino acid similarity to the amino acid sequence of SEQ ID NO:13.

---

What is claimed is:

1. A composition comprising:
   at least two polypeptides natively expressed by a *Bacillus* spp. at greater level when the *Bacillus* spp. is grown in culture medium comprising an iron chelator compared to when the *Bacillus* spp. is grown in culture medium without the iron chelator; and
   an adjuvant.

2. The composition of claim 1 further comprising:
   a polypeptide natively expressed by a *Bacillus* spp. having a molecular weight of 17 kDa as determined by SDS-PAGE and at least 90% amino acid similarity to the amino acid sequence of SEQ ID NO:12; or
   a polypeptide natively expressed by a *Bacillus* spp. having a molecular weight of 100 kDa as determined by SDS-PAGE and at least 90% amino acid similarity to the amino acid sequence of SEQ ID NO:13.

3. The composition of claim 1 wherein the at least two polypeptides comprise two or more of:
   a first polypeptide natively expressed by a *Bacillus* spp. having a molecular weight of 36 kDa as determined by SDS-PAGE and at least 90% amino acid similarity to the amino acid sequence of SEQ ID NO:1;
   a second polypeptide natively expressed by a *Bacillus* spp. having a molecular weight of 35 kDa as determined by SDS-PAGE and at least 90% amino acid similarity to the amino acid sequence of SEQ ID NO:2;
   a third polypeptide natively expressed by a *Bacillus* spp. having a molecular weight of 35 kDa as determined by SDS-PAGE and at least 90% amino acid similarity to the amino acid sequence of SEQ ID NO:3;
   a fourth polypeptide natively expressed by a *Bacillus* spp. having a molecular weight of 39 kDa as determined by SDS-PAGE and at least 90% amino acid similarity to the amino acid sequence of SEQ ID NO:4;
   a fifth polypeptide natively expressed by a *Bacillus* spp. having a molecular weight of 35 kDa as determined by SDS-PAGE and at least 90% amino acid similarity to the amino acid sequence of SEQ ID NO:5;
   a sixth polypeptide natively expressed by a *Bacillus* spp. having a molecular weight of 36 kDa as determined by SDS-PAGE and at least 90% amino acid similarity to the amino acid sequence of SEQ ID NO:6;
   a seventh polypeptide natively expressed by a *Bacillus* spp. having a molecular weight of 62 kDa as determined by SDS-PAGE and at least 90% amino acid similarity to the amino acid sequence of SEQ ID NO:7;

an eighth polypeptide natively expressed by a *Bacillus* spp. having a molecular weight of 32 kDa as determined by SDS-PAGE and at least 90% amino acid similarity to the amino acid sequence of SEQ ID NO:8;

a ninth polypeptide natively expressed by a *Bacillus* spp. having a molecular weight of 36 kDa as determined by SDS-PAGE and at least 90% amino acid similarity to the amino acid sequence of SEQ ID NO:9;

a tenth polypeptide natively expressed by a *Bacillus* spp. having a molecular weight of 38 kDa as determined by SDS-PAGE and at least 90% amino acid similarity to the amino acid sequence of SEQ ID NO:10;

an eleventh polypeptide natively expressed by a *Bacillus* spp. having a molecular weight of 39 kDa as determined by SDS-PAGE and at least 90% amino acid similarity to the amino acid sequence of SEQ ID NO:11;

a twelfth polypeptide natively expressed by a *Bacillus* spp. having a molecular weight of 36 kDa as determined by SDS-PAGE and at least 90% amino acid similarity to the amino acid sequence of SEQ ID NO:14;

a thirteenth polypeptide natively expressed by a *Bacillus* spp. having a molecular weight of 36 kDa as determined by SDS-PAGE and at least 90% amino acid similarity to the amino acid sequence of SEQ ID NO:15; or a fourteenth polypeptide natively expressed by a *Bacillus* spp. having a molecular weight of 35 kDa as determined by SDS-PAGE and at least 90% amino acid similarity to the amino acid sequence of SEQ ID NO:16.

4. The composition of claim 3 comprising:
the first polypeptide;
the second polypeptide;
the third polypeptide;
the fifth polypeptide;
the sixth polypeptide;
the eleventh polypeptide; and
the twelfth polypeptide.

5. The composition of claim 3 further comprising:
a fifteenth polypeptide natively expressed by a *Bacillus* spp. having a molecular weight of 17 kDa as determined by SDS-PAGE and at least 90% amino acid similarity to the amino acid sequence of SEQ ID NO:12; or a sixteenth polypeptide natively expressed by a *Bacillus* spp. having a molecular weight of 100 kDa as determined by SDS-PAGE and at least 90% amino acid similarity to the amino acid sequence of SEQ ID NO:13.

6. The composition of claim 1 wherein the composition protects against challenge by *Bacillus anthracis*.

* * * * *

SEQUENCE LISTING

```
<160> NUMBER OF SEQ ID NOS: 30

<210> SEQ ID NO 1
<211> LENGTH: 337
<212> TYPE: PRT
<213> ORGANISM: Bacillus anthracis

<400> SEQUENCE: 1

Met Lys Lys Thr Met Leu Leu Lys Leu Val Ser Ile Leu Ala Ile Phe
1               5                   10                  15

Thr Leu Met Leu Val Ala Cys Ser Asp Ser Gly Lys Glu Thr Ser Lys
```

```
            20                  25                  30
Ala Thr Lys Asp Asn Ser Ser Asp Lys Pro Lys Thr Val Glu Ile Thr
            35                  40                  45

Asp Ala His Gly Lys Val Lys Val Pro Val Asn Pro Lys Asn Val Val
        50                  55                  60

Ala Leu Asp Asn Arg Thr Phe Glu Thr Leu Ala Asp Trp Gly Ile Lys
65                  70                  75                  80

Leu Ala Ala Ala Pro Lys Asp Ile Met Pro Ala Asp Ser Ala Tyr Lys
                85                  90                  95

Lys Asp Glu Lys Val Gln Asn Ile Gly Asn His Arg Glu Pro Asn Leu
            100                 105                 110

Glu Ile Ile Ala Ala Ala Asn Pro Glu Leu Val Ile Val Gly Gln Arg
        115                 120                 125

Phe Ala Asp His Tyr Glu Glu Ile Lys Lys Leu Val Pro Asn Ala Ala
        130                 135                 140

Val Ile Asp Leu Asn Val Asp Val Ser Glu Lys Ala Thr Lys Pro Gly
145                 150                 155                 160

Glu Asn Leu Val Lys Gly Leu Lys Asp Ser Thr Ile Thr Leu Gly Lys
                165                 170                 175

Ile Phe Asn Lys Asp Lys Glu Ala Lys Gln Leu Val Ala Asp Phe Asp
                180                 185                 190

Lys Ser Ile Glu Lys Ala Lys Ser Ala Tyr Asn Gly Lys Asp Lys Val
            195                 200                 205

Met Ser Val Ile Val Thr Gly Gly Asn Ile Gly Phe Ala Ala Pro His
        210                 215                 220

Ser Gly Arg Val Trp Gly Pro Met Tyr Glu Ile Phe Gly Trp Thr Pro
225                 230                 235                 240

Ala Leu Glu Val Ser Asn Ser Thr Ala Gly His Lys Gly Asp Asp Val
                245                 250                 255

Ser Val Glu Ala Ile Ala Gln Thr Asn Pro Asp Trp Leu Phe Val Leu
            260                 265                 270

Asp Arg Asp Ala Ala Thr Ser Asp Ala Ala Lys Ser Ala Pro Ala Gln
        275                 280                 285

Asp Val Ile Ser Lys Ser Pro Ala Leu Gln Asn Thr Thr Ala Val Ser
        290                 295                 300

Lys Lys Gln Val Val Tyr Ala Pro Ala Asp Thr Tyr Thr Asn Glu Ser
305                 310                 315                 320

Ile Gln Thr Tyr Ile Glu Leu Phe Gly Asn Leu Ala Lys Thr Leu Ala
                325                 330                 335

Lys

<210> SEQ ID NO 2
<211> LENGTH: 314
<212> TYPE: PRT
<213> ORGANISM: Bacillus anthracis

<400> SEQUENCE: 2

Met Lys Asn Phe Lys Met Ala Leu Leu Ala Met Val Leu Val Val Thr
1               5                   10                  15

Ser Val Leu Phe Ala Ala Cys Ser Asn Lys Glu Glu Lys Lys Ala Asp
                20                  25                  30

Ala Lys Asp Ala Lys Thr Glu Glu Arg Thr Val Gln His Ala Lys Gly
            35                  40                  45

Glu Ile Lys Ile Pro Ala Asn Pro Lys Lys Ile Ala Asp Leu Ser Gly
```

```
                 50                  55                  60
Ser Thr Glu Glu Leu Leu Ile Phe Gly Met Lys Pro Ile Ile Thr Ala
 65                  70                  75                  80

Asn Thr Ser Gln Glu Lys Ile Asp Ala His Ile Glu Lys Lys Leu Lys
                 85                  90                  95

Asp Val Lys Pro Val Gly Ser Ala Trp Gly Asp Lys Ile Asn Ile Glu
            100                 105                 110

Ala Val Ala Ala Ala Lys Pro Asp Leu Ile Leu Val Asn Asn Arg Gln
        115                 120                 125

Glu Lys Ile Tyr Asp Gln Leu Ser Lys Ile Ala Pro Thr Val Met Leu
    130                 135                 140

Lys Thr Pro Leu Asp Gln Trp Arg Pro Lys Phe Glu Glu Val Gly Gln
145                 150                 155                 160

Ile Phe Gly Lys Glu Lys Glu Thr Lys Glu Trp Phe Lys Gln Tyr Asp
                165                 170                 175

Glu Lys Ala Ser Lys Leu His Asp Lys Ile Val Ala Lys Thr Gly Asp
            180                 185                 190

Ala Lys Phe Met Lys Met Ala Ala Tyr Pro Asn Ala Phe Arg Val Tyr
        195                 200                 205

Gly Asp Tyr Gly Tyr Gly Ser Val Ile Phe Asn Asp Leu Lys Leu Pro
    210                 215                 220

Ala Val Lys Gly Thr Pro Thr Asp Lys Pro Leu Val Gln Val Gln Lys
225                 230                 235                 240

Glu Ala Leu Ile Asp Tyr Asn Pro Asp Tyr Leu Phe Val Phe Thr Thr
                245                 250                 255

Gly Asp Gly Ser Gln Arg Leu Lys Glu Phe Gln Glu Glu Ser Ile Trp
            260                 265                 270

Lys Asn Met Asn Ala Val Lys Asn Asn His Val Phe Thr Ile Lys Asn
        275                 280                 285

Glu Glu Leu Asn Lys Gly Tyr Phe Pro Leu Gly Lys Glu Met Ile Leu
    290                 295                 300

Asp Glu Val Ala Glu Phe Val Leu Gly Lys
305                 310

<210> SEQ ID NO 3
<211> LENGTH: 305
<212> TYPE: PRT
<213> ORGANISM: Bacillus anthracis

<400> SEQUENCE: 3

Met Lys Lys Leu Phe Ile Ser Leu Thr Val Leu Phe Val Leu Val Met
  1               5                  10                  15

Ser Ala Cys Ser Asn Gly Ser Thr Asp Lys Lys Asn Asp Ala Lys Gly
                 20                  25                  30

Ser Lys Ser Glu Thr Ile Thr Tyr Gln Ser Glu Asn Gly Lys Val Glu
            35                  40                  45

Val Pro Ala Asn Pro Lys Arg Val Val Leu Ser Ser Phe Ala Gly
        50                  55                  60

Asn Val Met Ser Leu Gly Val Asn Leu Val Gly Val Asp Ser Trp Ser
 65                  70                  75                  80

Lys Gln Asn Pro Arg Phe Asp Ser Lys Leu Lys Asp Val Ala Glu Val
                 85                  90                  95

Ser Asp Glu Asn Val Glu Lys Ile Ala Glu Leu Asn Pro Asp Leu Ile
            100                 105                 110
```

```
Ile Gly Leu Ser Asn Ile Lys Asn Val Asp Lys Leu Lys Ile Ala
            115                 120                 125

Pro Thr Val Thr Tyr Thr Tyr Gly Lys Val Asp Tyr Leu Thr Gln His
130                 135                 140

Leu Glu Ile Gly Lys Leu Leu Asn Lys Glu Lys Glu Ala Lys Thr Trp
145                 150                 155                 160

Val Asp Asp Phe Lys Lys Arg Ala Gln Asp Ala Gly Lys Glu Ile Lys
                165                 170                 175

Ala Lys Ile Gly Glu Asp Ala Thr Val Ser Val Val Glu Asn Phe Asn
            180                 185                 190

Lys Gln Leu Tyr Val Tyr Gly Glu Asn Trp Gly Arg Gly Thr Glu Ile
        195                 200                 205

Leu Tyr Gln Glu Met Lys Leu Lys Met Pro Glu Lys Val Lys Glu Lys
210                 215                 220

Ala Leu Lys Glu Gly Tyr Tyr Ala Leu Ser Thr Glu Val Leu Pro Glu
225                 230                 235                 240

Phe Ala Gly Asp Tyr Leu Ile Val Ser Lys Asn Lys Asp Thr Asp Asn
                245                 250                 255

Ser Phe Gln Glu Thr Glu Ser Tyr Lys Asn Ile Pro Ala Val Lys Asn
            260                 265                 270

Asn Arg Val Tyr Glu Ala Asn Met Met Glu Phe Tyr Phe Asn Asp Pro
        275                 280                 285

Leu Thr Leu Asp Phe Gln Leu Asp Phe Phe Lys Lys Ser Phe Leu Gly
290                 295                 300

Lys
305

<210> SEQ ID NO 4
<211> LENGTH: 354
<212> TYPE: PRT
<213> ORGANISM: Bacillus anthracis

<400> SEQUENCE: 4

Met Ile Thr Leu Asp Tyr Arg Asn Lys Glu Asn Val Glu Val Asp Ser
1               5                   10                  15

Ser Leu His Asn Glu Ser Arg Ser Ala Ser Ala Phe Arg Ser Lys Lys
            20                  25                  30

Glu Ala Arg Arg Tyr Trp Ile Val Leu Ile Thr Leu Ile Ala Leu Gly
        35                  40                  45

Leu Leu Ser Ser Tyr Gly Leu Leu Val Tyr Asn Asn Pro Val Pro Ile
50                  55                  60

Asp Ser Pro Ser Phe Ile Pro Val Val Lys Arg Arg Ile Val Ala Ile
65                  70                  75                  80

Val Ala Met Ile Ile Ala Ala Val Cys His Ser Leu Ser Thr Val Ala
                85                  90                  95

Phe Gln Ser Ile Thr Asn Asn Lys Ile Ile Thr Pro Ser Leu Leu Gly
            100                 105                 110

Phe Glu Ser Leu Tyr Ser Ala Ile Gln Thr Ser Thr Val Phe Phe Phe
        115                 120                 125

Gly Ala Ser Ala Leu Ile Asn Phe Asn Gly Ile Gly Ser Phe Leu Phe
130                 135                 140

Gln Val Val Val Met Val Phe Met Ser Leu Ile Leu Tyr Gly Trp Leu
145                 150                 155                 160

Leu Ser Gly Lys Tyr Gly Asn Leu Gln Leu Met Leu Leu Val Gly Ile
                165                 170                 175
```

-continued

```
Ile Ile Gly Thr Gly Leu Asn Ser Val Ser Thr Phe Met Arg Lys Leu
            180                 185                 190

Leu Ala Pro Ser Glu Phe Asp Ile Leu Gln Ala Arg Leu Phe Gly Ser
        195                 200                 205

Val Asn His Ala Asp Pro Ala Tyr Phe Pro Ile Val Ile Pro Met Ile
    210                 215                 220

Ile Ile Val Ala Val Leu Ile Phe Ala His Ser Lys Asn Leu Asn Val
225                 230                 235                 240

Leu Ser Leu Gly Lys Asp Val Ala Thr Ser Phe Gly Val Lys Tyr Gln
                245                 250                 255

Pro Ser Val Ile Tyr Thr Leu Val Leu Val Ala Ile Leu Met Ser Ile
            260                 265                 270

Ser Thr Ala Leu Ile Gly Pro Leu Thr Phe Tyr Gly Phe Leu Val Ala
        275                 280                 285

Thr Leu Ser Tyr Gln Ala Ala Ala Thr Tyr Asp His Arg Tyr Ile Phe
    290                 295                 300

Pro Met Ala Phe Ala Ile Gly Phe Leu Ile Met Thr Ser Ala Tyr Phe
305                 310                 315                 320

Leu Met Tyr His Val Phe His Ala Gln Gly Val Val Ser Val Ile Ile
                325                 330                 335

Glu Leu Phe Gly Gly Ile Ile Phe Leu Thr Ile Val Leu Arg Lys Arg
            340                 345                 350

Ala Leu

<210> SEQ ID NO 5
<211> LENGTH: 315
<212> TYPE: PRT
<213> ORGANISM: Bacillus anthracis

<400> SEQUENCE: 5

Met Lys Lys Ser Ile Thr Leu Phe Thr Ala Ile Leu Ser Ile Phe Phe
1               5                   10                  15

Leu Leu Ile Gly Cys Ser Ala Lys Gly Asp Glu Lys Ala Ser Ala Thr
            20                  25                  30

Lys Thr Glu Lys Gly Lys Glu Lys Ile Glu Val Thr Asp Leu Ser Gly
        35                  40                  45

Arg Lys Val Thr Phe Asp Lys Val Pro Glu Ser Phe Ala Thr Leu Ser
    50                  55                  60

Met Gly Asp Met Asn Ile Ile His Ala Leu Gly Gly Lys Ile Val Gly
65                  70                  75                  80

Arg Pro Asp Ala Lys Ile Thr Leu Pro Glu Asp Ile Lys Lys Ile Gln
                85                  90                  95

Val Ile Gly Asn Ala His Gln Pro Asn Phe Glu Gln Ile Ala Ser Leu
            100                 105                 110

Lys Pro Asp Val Leu Ile Ala Asn Asn Gly Phe Gln Lys Asn Ile Pro
        115                 120                 125

Thr Val Glu Gly Gln Gly Thr Lys Val Met Ile Ser Ser Ala Asn Ser
    130                 135                 140

Val Gln Asp Ile Gln Lys Asn Ile Glu Leu Tyr Gly Thr Ile Met Lys
145                 150                 155                 160

Lys Glu Asp Lys Ala Asn Glu Leu Asn Gln Lys Ile Asn Val Gln Met
                165                 170                 175

Lys Lys Tyr Glu Lys Lys Ser Asp Val Lys Ala Leu Leu Val Tyr Gly
            180                 185                 190
```

```
Ala Pro Gly Thr Tyr Leu Ala Ala Leu Pro Thr Ser Leu Ser Gly Asp
        195                 200                 205

Ile Leu Glu Lys Thr Gly Gly Lys Asn Ile Ala Ala Asp Phe Pro Glu
    210                 215                 220

Met Lys Glu Tyr Pro Gln Tyr Ala Gln Leu Ser Val Glu Arg Ile Ile
225                 230                 235                 240

Glu Ala Asn Pro Asp Val Ile Tyr Leu Ile Thr His Gly Asp Pro Asn
            245                 250                 255

Ser Val Lys Lys Ala Phe Glu Gly Glu Met Met Lys Asn Glu Ala Trp
        260                 265                 270

Lys Asn Leu Asp Ala Val Lys Gln Asn Arg Val Val Ile Leu Pro Pro
            275                 280                 285

Asp Leu Phe Gly Ser Asn Pro Gly Thr Lys Val Thr Glu Ala Met Asp
    290                 295                 300

Phe Met Tyr Lys Ser Ile Gln Asp Val Arg Lys
305                 310                 315
```

<210> SEQ ID NO 6
<211> LENGTH: 324
<212> TYPE: PRT
<213> ORGANISM: Bacillus anthracis

<400> SEQUENCE: 6

```
Met Lys Lys Ile Leu Ser Ile Phe Ile Val Val Phe Leu Phe Ala Val
1               5                   10                  15

Gly Cys Gly Gln Gln Lys Glu Glu Lys Glu Thr Lys Ala Asp Asn
            20                  25                  30

Lys Asn Gln Ala Ile Thr Ile Lys His Ala Glu Gly Glu Thr Lys Leu
        35                  40                  45

Asp Lys Pro Ala Lys Lys Val Val Leu Glu Trp Val Tyr Ser Glu
    50                  55                  60

Asp Leu Leu Ala Leu Gly Val Gln Pro Val Gly Met Ala Asp Ile Lys
65                  70                  75                  80

Asn Tyr Asn Lys Trp Val Asn Thr Lys Thr Lys Pro Ser Lys Asp Val
                85                  90                  95

Val Asp Val Gly Thr Arg Gln Gln Pro Asn Leu Glu Glu Ile Ser Arg
            100                 105                 110

Leu Lys Pro Asp Leu Ile Ile Thr Ala Ser Phe Arg Gly Lys Ala Ile
        115                 120                 125

Lys Asn Glu Leu Glu Gln Ile Ala Pro Thr Val Met Phe Asp Pro Ser
    130                 135                 140

Thr Ser Asn Asn Asp His Phe Ala Glu Met Thr Glu Thr Phe Lys Gln
145                 150                 155                 160

Ile Ala Lys Ala Val Gly Lys Glu Glu Gly Lys Lys Val Leu Ala
                165                 170                 175

Asp Met Asp Lys Ala Phe Ala Asp Ala Lys Ala Lys Ile Glu Lys Ala
            180                 185                 190

Asp Leu Lys Asp Lys Asn Ile Ala Met Ala Gln Ala Phe Thr Ala Lys
        195                 200                 205

Asn Val Pro Thr Phe Arg Ile Leu Thr Asp Asn Ser Leu Ala Leu Gln
    210                 215                 220

Val Thr Lys Lys Leu Gly Leu Thr Asn Thr Phe Glu Ala Gly Lys Ser
225                 230                 235                 240

Glu Pro Asp Gly Phe Lys Gln Thr Thr Val Glu Ser Leu Gln Ser Val
```

```
            245                 250                 255
Gln Asp Ser Asn Phe Ile Tyr Ile Val Ala Asp Glu Asp Asn Ile Phe
            260                 265                 270

Asp Thr Gln Leu Lys Gly Asn Pro Ala Trp Glu Glu Leu Lys Phe Lys
            275                 280                 285

Lys Glu Asn Lys Met Tyr Lys Leu Lys Gly Asp Thr Trp Ile Phe Gly
290                 295                 300

Gly Pro Glu Ser Ala Thr Ser Leu Ala Thr Gln Val Ala Asp Val Met
305                 310                 315                 320

Thr Ala Lys Lys

<210> SEQ ID NO 7
<211> LENGTH: 543
<212> TYPE: PRT
<213> ORGANISM: Bacillus anthracis

<400> SEQUENCE: 7

Met Lys Lys Lys Ile Pro Leu Leu Leu Ala Ser Thr Leu Thr Val Ser
1               5                   10                  15

Met Leu Gly Ala Cys Ser Tyr Gln Lys Glu Asp Asn Lys Ala Gly Ala
            20                  25                  30

Lys Glu Lys Ser Ser Asn Lys Gln Val Leu Asn Leu Thr Glu Thr Ala
        35                  40                  45

Glu Ile Pro Thr Met Asp Thr Thr Leu Ser Thr Asp Ala Thr Ser Ser
    50                  55                  60

Asn Ile Met Asn Asn Thr Met Glu Gly Leu Tyr Arg Leu Gly Lys Glu
65                  70                  75                  80

Asp Lys Leu Val Pro Gly Val Ala Lys Ser Tyr Glu Lys Ser Glu Asp
                85                  90                  95

Gly Lys Lys Tyr Val Phe Lys Leu Arg Glu Asp Ala Lys Trp Ser Asn
            100                 105                 110

Gly Glu Pro Val Thr Ala Lys Asp Phe Val Tyr Ser Trp Arg Arg Ala
        115                 120                 125

Val Asp Ser Asn Thr Gly Ala Lys Phe Ala Tyr Ile Leu Phe Asp Val
    130                 135                 140

Lys Asn Ala Glu Lys Val Asn Lys Lys Glu Leu Pro Val Glu Glu Leu
145                 150                 155                 160

Gly Val Lys Ala Ile Asp Asp His Thr Leu Glu Val Glu Leu Asp Asn
                165                 170                 175

Pro Val Pro Tyr Phe Val Ser Leu Thr Val Tyr Pro Thr Leu Tyr Pro
            180                 185                 190

Leu Asn Glu Lys Phe Val Thr Glu Gln Gly Ala Lys Phe Gly Leu Glu
        195                 200                 205

Ser Asn Thr Thr Leu Tyr Asn Gly Pro Phe Val Leu Asn Glu Trp Lys
    210                 215                 220

His Glu Gln Ser Phe Gln Leu Lys Lys Asn Pro Ser Tyr Trp Glu Asn
225                 230                 235                 240

Lys Glu Val Lys Leu Glu Glu Ile Asn Phe Asn Ile Val Lys Asp Arg
                245                 250                 255

Ser Thr Ala Ile Asn Leu Tyr Glu Thr Lys Ala Ile Asp Arg Val Val
            260                 265                 270

Leu Thr Ser Glu Phe Val Asp Lys Tyr Lys Ser Asp Ala Asp Phe Lys
        275                 280                 285

Thr Ile Lys Lys Pro Ser Thr Gln Phe Ile Arg Leu Asn Glu Lys Asn
```

```
                    290                 295                 300

Lys Phe Leu Ala Asn Lys Asn Ile Arg Lys Ala Ile Ala Met Ser Phe
305                 310                 315                 320

Glu Arg Glu Asn Ile Gly Lys Val Ile Leu Asn Asp Gly Ser Glu Gly
                325                 330                 335

Ile Tyr Gly Phe Val Pro Lys Gly Leu Ala Lys Gly Pro Asn Gly Lys
            340                 345                 350

Asp Phe Arg Glu Glu Asn Gly Lys Leu Ile Lys Glu Asp Met Lys Glu
        355                 360                 365

Ala Gln Lys Tyr Trp Glu Ala Gly Lys Glu Leu Gly Val Asp Lys
    370                 375                 380

Val Glu Leu Glu Leu Leu Asn Phe Asp Thr Asp Ala Lys Lys Ile
385                 390                 395                 400

Gly Glu Tyr Leu Lys Gly Gln Phe Glu Lys Asn Leu Pro Gly Leu Thr
                405                 410                 415

Val Pro Thr Lys Met Gln Pro Phe Ala Gln Lys Leu Lys Leu Glu Ala
            420                 425                 430

Ser Gly Asp Tyr Ala Met Ser Tyr Ala Gly Trp Ser Pro Asp Tyr Met
        435                 440                 445

Asp Pro Met Ser Phe Leu Glu Met Tyr Thr Thr Gly Asn Ala Gln Asn
    450                 455                 460

Lys Val His Tyr Ala Asn Pro Ala Tyr Asp Asp Leu Ile Lys Lys Ala
465                 470                 475                 480

Lys Thr Glu Val Asp Val Gln Ala Arg Trp Asp Ala Leu Leu Gln Ala
                485                 490                 495

Glu Lys Gln Leu Leu Glu Asp Ala Ala Ile Ala Pro Val Tyr Gln Pro
        500                 505                 510

Gly Lys Ala Tyr Leu Gln Arg Gly Ser Ile Thr Gly Leu Leu Glu His
    515                 520                 525

Lys Tyr Gly Gly Glu Phe Ser Tyr Lys Trp Val Glu Leu Lys Asn
530                 535                 540

<210> SEQ ID NO 8
<211> LENGTH: 291
<212> TYPE: PRT
<213> ORGANISM: Bacillus anthracis

<400> SEQUENCE: 8

Met Lys Lys Ile Ala Ser Val Leu Met Ala Ile Ile Leu Leu Val Ser
1               5                   10                  15

Ile Ala Gly Cys Ser Ala Pro Lys Lys Glu Ala Ala Lys Gln Val Lys
                20                  25                  30

Ser Glu Ser Lys Glu Arg Val Val Ala Thr Thr Val Ala Val Thr Glu
        35                  40                  45

Ile Met Asp Ala Leu Glu Val Asp Leu Val Gly Val Pro Thr Ser Thr
    50                  55                  60

Lys Asp Leu Pro Lys Arg Tyr Lys Gly Leu Pro Glu Val Gly Asn Pro
65                  70                  75                  80

Met Ser Pro Asp Met Glu Lys Val Lys Ser Leu Lys Pro Ser Glu Val
                85                  90                  95

Leu Ser Val Thr Thr Leu Glu Tyr Glu Leu Lys Pro Val Phe Asp Gly
        100                 105                 110

Val Gly Met Lys Ala Asn Phe Val Asp Leu Thr Ser Leu Lys Asn Met
    115                 120                 125
```

Gln Asn Ala Ile Ser Asn Leu Gly Lys Gln Tyr Gly Arg Glu Lys Gln
130                 135                 140

Ala Glu Ala Val Val Thr Lys Leu Asp Lys Lys Val Ala Ser Ile Arg
145                 150                 155                 160

Lys Glu Val Lys Gly Lys Arg Glu Pro Thr Val Leu Ile Leu Leu Gly
            165                 170                 175

Val Pro Gly Ser Tyr Leu Val Ala Thr Glu His Ser Tyr Ile Gly Asp
            180                 185                 190

Leu Val Lys Gln Leu Gly Gly Lys Asn Ile Val Gln Gly Glu Lys Val
        195                 200                 205

Glu Tyr Leu Ala Ser Asn Thr Glu Tyr Leu Lys Lys Ala Asp Pro Asp
210                 215                 220

Ile Ile Leu Arg Ala Ala His Gly Met Pro Asp Glu Val Val Lys Met
225                 230                 235                 240

Phe Asp Lys Glu Phe Lys Thr Asn Asp Ile Trp Lys His Phe Ala Ala
                245                 250                 255

Val Lys Asn Asn Arg Val Tyr Asp Leu Glu Glu Arg Leu Phe Gly Thr
            260                 265                 270

Thr Gly Asn Leu Ala Ala Ile Glu Ala Leu Asp Glu Leu Lys Lys Met
        275                 280                 285

Met Tyr Pro
290

<210> SEQ ID NO 9
<211> LENGTH: 320
<212> TYPE: PRT
<213> ORGANISM: Bacillus anthracis

<400> SEQUENCE: 9

Met Thr Arg Thr Lys Asn Met Leu Ile Phe Cys Ile Met Leu Leu Thr
1               5                   10                  15

Ile Ile Ile Ala Gly Cys Ser Lys Glu Glu Lys Lys Glu Asn Asp Thr
                20                  25                  30

Ser Ala Lys Ala Lys Asp Ser Tyr Thr Ile Lys His Ala Met Gly Glu
            35                  40                  45

Thr Thr Val Asp Gly Thr Pro Lys Arg Val Val Leu Thr Asn Glu
50                  55                  60

Gly Ala Glu Ala Leu Leu Ser Val Gly Val Thr Pro Val Gly Thr Thr
65                  70                  75                  80

Lys Pro Arg Ala Gly Asp Glu Trp Tyr Pro His Leu Ala Lys Glu Leu
                85                  90                  95

Lys Asn Thr Lys Val Val Gly Thr Glu Arg Asp Ile Asn Leu Glu Ala
            100                 105                 110

Val Met Lys Leu Gln Pro Asp Leu Ile Ile Gly Asn Lys Met Arg His
        115                 120                 125

Glu Lys Ile Tyr Glu Gln Leu Lys Glu Ile Ala Pro Thr Val Tyr Ala
130                 135                 140

Glu Thr Leu Arg Gly Asp Trp Lys Glu Asn Phe Thr Leu Tyr Thr Lys
145                 150                 155                 160

Ala Val Asn Lys Glu Lys Glu Gly Gln Asn Ala Leu Asn Asp Tyr Lys
                165                 170                 175

Lys Arg Ile Ala Gly Ile Lys Glu Lys Leu Gly Glu Lys Val Asn Ser
            180                 185                 190

Lys Val Ser Ile Ile Arg Phe Val Pro Gly Asp Val Arg Ile Tyr Gln
        195                 200                 205

```
Lys Asn Ser Phe Ser Gly Val Val Leu Asn Asp Ile Gly Phe Lys Arg
            210                 215                 220

Pro Pro Leu Gln Asp Lys Asp Glu Phe Ala Ile Lys Gly Ile Thr Lys
225                 230                 235                 240

Glu Gln Ile Pro Asn Met Asp Gly Asp Tyr Leu Phe Tyr Phe Thr Ser
                    245                 250                 255

Asp Lys Asp Ala Asp Lys Asn Asn Glu Gly Asn Thr Leu Ala Lys Glu
                260                 265                 270

Trp Thr Glu Asp Pro Leu Phe Lys Gln Leu Gln Ala Ser Lys Asp Asn
            275                 280                 285

Lys Val Phe Gln Val Asp Glu Val Ile Trp Asn Thr Ala Gly Gly Ile
290                 295                 300

Val Ala Ala Asn Leu Met Leu Asp Asp Ile Glu Lys Tyr Phe Leu Lys
305                 310                 315                 320

<210> SEQ ID NO 10
<211> LENGTH: 355
<212> TYPE: PRT
<213> ORGANISM: Bacillus anthracis

<400> SEQUENCE: 10

Met Lys Lys Lys Thr Gly Leu Leu Ser Leu Thr Leu Ala Ala Ser
1               5                   10                  15

Ala Val Leu Gly Ala Cys Gly Asn Ser Asp Lys Ala Ser Ser Asp Lys
                20                  25                  30

Lys Glu Phe Lys Val Gly Met Val Thr Asp Val Gly Gly Val Asp Asp
                35                  40                  45

Lys Ser Phe Asn Gln Ser Ala Trp Glu Gly Leu Thr Lys Phe Gly Lys
            50                  55                  60

Asp Asn Asn Leu Lys Lys Asn Glu Gly Tyr Arg Tyr Leu Gln Ser Ser
65              70                  75                  80

Lys Asp Ala Asp Tyr Ile Pro Asn Leu Thr Lys Phe Ala Lys Asp His
                85                  90                  95

Tyr Asn Thr Thr Phe Gly Ile Gly Tyr Leu Met Glu Lys Ser Ile Glu
                100                 105                 110

Lys Val Ala Glu Gln Tyr Pro Lys Glu Gln Phe Ala Ile Val Asp Thr
            115                 120                 125

Val Val Glu Lys Pro Asn Val Thr Ser Ile Thr Phe Lys Asp His Glu
130                 135                 140

Gly Ser Phe Leu Val Gly Ala Val Ala Ala Met Thr Thr Lys Ser Asn
145                 150                 155                 160

Lys Val Gly Phe Val Gly Gly Val Lys Ser Pro Leu Ile Thr Lys Phe
                165                 170                 175

Glu Ser Gly Phe Lys Ala Gly Ala Lys Ala Val Asn Pro Asn Ile Glu
            180                 185                 190

Ile Val Ser Gln Tyr Ala Asp Ala Phe Asp Lys Pro Glu Lys Gly Ser
            195                 200                 205

Val Leu Ala Ser Ala Met Tyr Gly Gly Gly Val Asp Val Ile Tyr His
            210                 215                 220

Ala Ser Gly Ala Thr Gly Asn Gly Val Phe Thr Glu Ala Lys Asn Arg
225                 230                 235                 240

Lys Lys Lys Gly Glu Asn Val Trp Val Ile Gly Val Asp Arg Asp Gln
                245                 250                 255

Asn Gln Glu Gly Met Pro Glu Asn Val Thr Leu Thr Ser Met Val Lys
```

```
                        260                 265                 270
Arg Val Asp Val Ala Val Ala Lys Val Ala Gln Glu Ala Lys Asp Gly
            275                 280                 285
Lys Leu Lys Gly Gly Lys Val Glu Glu Phe Gly Leu Lys Asp Asp Gly
            290                 295                 300
Val Gly Ile Ala Lys Thr Thr Asp Asn Val Lys Lys Val Asn Pro Glu
305                 310                 315                 320
Ile Leu Thr Lys Val Glu Glu Phe Glu Lys Lys Ile Thr Asp Gly Glu
                325                 330                 335
Ile Lys Val Pro Ala Thr Asp Glu Glu Tyr Lys Ala Tyr Glu Ala Ser
            340                 345                 350
Leu Lys Lys
        355

<210> SEQ ID NO 11
<211> LENGTH: 346
<212> TYPE: PRT
<213> ORGANISM: Bacillus anthracis

<400> SEQUENCE: 11

Met Ile Met Ile Lys Lys Tyr Met Asn Ala Phe Val Ile Ala Ala
1               5                   10                  15
Thr Leu Ala Val Pro Phe Ser Ser Ile Met Ala Pro Ile Ala Lys Ala
                20                  25                  30
Glu Ala Ala Val Glu Met Lys Ala Ala Ser Lys Leu Ala Asp Gly Thr
            35                  40                  45
Tyr Asp Val Ile Leu Lys Thr Tyr Lys Asp Lys Thr Asn Asp Thr Ser
        50                  55                  60
Val Ala Ser Thr Tyr Leu Lys Asn Leu Lys Val Thr Ile Gln Gly Asp
65                  70                  75                  80
Lys Lys Ile Val Thr Leu Thr Val Gln Asp Ser Ser Tyr Phe Gln Tyr
                85                  90                  95
Leu Arg Val Glu Asp Thr Asn Lys Val Gly Thr Phe His Asp Val Lys
            100                 105                 110
Val Ile Ser Glu Asp Lys Ala Asn Asn Gly Thr Lys Val Val Gln Phe
        115                 120                 125
Glu Ile Asp Glu Phe Ser Lys Lys Tyr Asn Met Gln Met His Ile Leu
130                 135                 140
Ile Pro Ala Ile Lys Tyr Asp His Lys Tyr Gln Val Gln Phe Glu Ile
145                 150                 155                 160
Asp Ala Ser Ala Ile Glu Gln Lys Pro Lys Phe Ser Asp Val Pro Thr
                165                 170                 175
Trp Ala Gln Glu Ser Val Gln Tyr Leu Val Asp Lys Glu Ala Val His
            180                 185                 190
Gly Lys Pro Asp Gly Thr Phe Ala Pro Ala Glu Ser Ile Asp Arg Ser
        195                 200                 205
Ser Ala Ala Lys Ile Leu Ala Thr Val Leu Arg Leu Glu Ile Lys Lys
210                 215                 220
Asp Ala Lys Pro Ser Phe Pro Asp Ala Gln Asn His Trp Ala Thr Pro
225                 230                 235                 240
Tyr Ile Ala Ala Val Glu Lys Ala Gly Ile Val Lys Gly Asp Glu Lys
                245                 250                 255
Gly Asn Phe Asn Pro Ser Gly Leu Ile Asn Arg Ala Ser Met Ala Ser
            260                 265                 270
```

```
Met Leu Val Asn Ala Tyr Lys Leu Glu Arg Asn Glu Asn Ile Lys Leu
            275                 280                 285

Pro Lys Glu Phe Ala Asp Leu Asn Asn His Trp Gly Ala Lys Tyr Ala
    290                 295                 300

Asn Ile Leu Ile Gln Glu Lys Ile Ser Ile Gly Thr Asp Asn Gly Trp
305                 310                 315                 320

Ala Pro Asn Lys Ala Val Ser Arg Ala Glu Ala Gln Phe Ile Ala
                325                 330                 335

Lys Ala Asp Lys Leu Lys Lys Glu Met Lys
            340                 345

<210> SEQ ID NO 12
<211> LENGTH: 152
<212> TYPE: PRT
<213> ORGANISM: Bacillus anthracis

<400> SEQUENCE: 12

Met Phe Lys Gln Phe Lys Met Ile Ile Ala Val Phe Ala Val Leu Phe
1               5                   10                  15

Thr Phe Ile Ala Thr Leu Gly Leu Gln Asp Ala Lys Ala Ala Thr Lys
            20                  25                  30

Leu Ala Asp Gly Lys Tyr Asn Ile Ala Phe Thr Val Trp Lys Gly Asp
        35                  40                  45

Lys Asp Glu Ser Ser Arg Met Asn Arg Tyr Phe Glu Ser Pro Ala Thr
    50                  55                  60

Leu Thr Val Lys Asn Gly Lys Gln Tyr Val Ser Phe Lys Val Lys Asp
65                  70                  75                  80

Ser Thr Ser Ile Lys Ser Phe Gln Val Glu Lys Asp Gly Gln Phe Val
                85                  90                  95

Glu Thr Thr Val Leu Ser Glu Asn Lys Lys Asp Asn Thr Arg Val Val
            100                 105                 110

Glu Phe Glu Val Ala Asp Leu Ser Lys Lys Leu Asn Gly Lys Val Lys
        115                 120                 125

Ile Asn Ile Pro Ile Ile Asn Tyr Asn Ala Ser Tyr Asp Ile Arg Phe
    130                 135                 140

Val Phe Asp Gly Asn Ser Ile Lys
145                 150

<210> SEQ ID NO 13
<211> LENGTH: 885
<212> TYPE: PRT
<213> ORGANISM: Bacillus anthracis

<400> SEQUENCE: 13

Met Asn Arg Tyr Thr Lys Ile Ile Val Ala Met Phe Leu Met Ile Phe
1               5                   10                  15

Thr Phe Val Ser Thr Leu Gln Pro Leu Ala Val Gln Ala Ala Thr Lys
            20                  25                  30

Leu Ala Asp Gly Glu Tyr Ser Ile Gly Phe Lys Val Leu Lys Asp Thr
        35                  40                  45

Ser Asp Glu Glu Ser Met Met Asn Gln Tyr Ser Val Ser Pro Gly Thr
    50                  55                  60

Leu Lys Val Lys Asp Gly Lys Lys Val Ser Phe Thr Leu Thr Asn
65                  70                  75                  80

Ser Ser Trp Ile Thr Lys Phe Glu Thr Glu Lys Ala Gly Lys Leu Val
                85                  90                  95
```

-continued

```
Ala Thr Asn Val Ile Ser Glu Asp Lys Glu Lys Asp Thr Arg Val Val
            100                 105                 110
Glu Phe Asp Val Glu Asp Val Glu Lys Val Leu Asn Ala Lys Val Lys
        115                 120                 125
Val Asp Ile Asp Phe Leu Asn Tyr His His Glu Tyr Asp Val Arg Ile
    130                 135                 140
Ala Phe Asp Gln Asn Ser Ile Thr Pro Ile His Val Glu Gln Pro Asn
145                 150                 155                 160
Glu Lys Glu Asp Pro Ala Asn Lys Pro Asp Pro Asn Glu Lys Pro Asp
                165                 170                 175
Pro Ser Gln Lys Pro Asp Gln Lys Pro Asp Pro Asp Gln Gln Pro Asn
            180                 185                 190
Ser Asn Thr Ile Lys Asp Gly Glu Tyr Ser Ile Pro Phe Lys Val Leu
        195                 200                 205
Lys Asn Gln Thr Asp Glu Glu Ser Lys Met Asn Thr Tyr Met Val Asn
    210                 215                 220
Pro Gly Val Leu Lys Ile Glu Asn Gly Lys Lys Ala Ile Val Thr
225                 230                 235                 240
Leu Lys Ser Ser Leu Ile Lys Asn Phe Gln Thr Glu Lys Asp Gly
                245                 250                 255
Ala Phe Val Asp Ala Lys Val Val Ser Glu Asn Lys Glu Lys Asp Thr
            260                 265                 270
Arg Val Val Glu Phe Glu Val Ala Asp Leu Ser Lys Lys Leu Asn Thr
        275                 280                 285
Lys Val Phe Ile Glu Met Ala Ser Arg Asn Tyr Lys Gln Thr His Asp
    290                 295                 300
Val Gln Leu Leu Phe Glu Gln Asp Lys Leu Glu Gln Ile Lys Asn Glu
305                 310                 315                 320
Glu Lys Gln Pro Glu Val Lys Pro Glu Val Lys Pro Glu Val
                325                 330                 335
Glu Lys Pro Glu Val Glu Lys Pro Asp Glu Asn Lys Lys Thr Asp Ala
            340                 345                 350
Glu Thr Ile Lys Asp Gly Glu Tyr Ser Ile Asn Phe Lys Ala Leu Lys
        355                 360                 365
Asp Gln Thr Asp Glu Ile Ser Met Met Asn Thr Tyr Thr Lys Ser Pro
    370                 375                 380
Gly Leu Leu Lys Val Lys Asp Gly Lys Lys Tyr Val Ser Phe Thr Leu
385                 390                 395                 400
Thr Asn Ser Ser Trp Ile Thr Lys Phe Glu Phe Glu Lys Asn Gly Ser
                405                 410                 415
Phe Val Asp Ala Asn Val Ile Ser Glu Asp Lys Lys Ala Asp Thr Arg
            420                 425                 430
Val Val Glu Val Ala Val Asp Asp Leu Ser Lys Lys Leu Asn Ala Lys
        435                 440                 445
Val Lys Val Asp Ile Asp Ser Met Asn Tyr His His Phe Tyr Asp Ile
    450                 455                 460
Gln Phe Ala Phe Asp Lys Gly Ser Ile Lys Pro Leu Asp Asn Gln Gly
465                 470                 475                 480
Gly Asn Asp Asn Gln Gly Gly Asn Asn Gln Gly Gly Asn Asn Asn
                485                 490                 495
His Asp Asp Asn Lys Thr Ile Asp Pro Asn Ala Leu Lys Asp Gly Glu
            500                 505                 510
Tyr Ser Ile Gly Phe Lys Val Leu Lys Asp Lys Thr Glu Glu Ile Ser
```

```
            515                 520                 525
Met Met Asn Thr Tyr Thr Lys Asn Pro Gly Val Leu Lys Val Lys Asp
        530                 535                 540

Gly Lys Lys Tyr Val Ser Phe Thr Leu Thr Asn Ser Ser Trp Ile Thr
545                 550                 555                 560

Lys Phe Glu Phe Glu Lys Asn Gly Ala Phe Val Asp Ala Lys Val Leu
                565                 570                 575

Gly Thr Asn Lys Glu Gln Asp Thr Arg Val Val Glu Val Glu Val Ala
            580                 585                 590

Asp Leu Ser Lys Lys Leu Asn Ala Lys Val Lys Val Asp Ile Asp Ser
            595                 600                 605

Met Asn Tyr His His Phe Tyr Asp Ile Gln Phe Ala Phe Asp Lys Gly
        610                 615                 620

Ser Ile Lys Ser Leu Gly Asn Gln Gly Gly Asp Thr Asn Gln Asp Gly
625                 630                 635                 640

Asn Gly Asn Gln Gly Gly Asn Asp Asn Gln Gly Gly Ser Asn Asn Gln
                645                 650                 655

Asp Asp Asn Asn Asn Gln Asp Gly Thr Asn Asn Leu Asn Glu Asn Pro
            660                 665                 670

Thr Val Asp Pro Lys Asn Leu Lys Asp Gly Gln Tyr Asp Ile Ala Phe
            675                 680                 685

Lys Val Leu Lys Asp Lys Thr Glu Glu Ile Ser Met Met Asn Gln Tyr
        690                 695                 700

Val Val Ser Pro Ala Arg Leu Thr Val Lys Asp Gly Lys Lys Tyr Ile
705                 710                 715                 720

Ala Met Thr Leu Lys Asn Ser Glu Trp Ile Thr Lys Phe Gln Thr Glu
                725                 730                 735

Lys Asn Gly Gly Phe Ala Asp Ala Lys Val Val Ser Glu Asp Lys Ala
            740                 745                 750

Ala Asn Thr Arg Val Val Glu Phe Glu Ala Asn Asp Leu Phe Ala Lys
            755                 760                 765

Leu Asn Ala Lys Val Lys Val Asp Ile Asp Ser Met Asn Tyr His His
        770                 775                 780

Phe Tyr Asp Val Gln Ile Gln Phe Asp Pro Thr Lys Ile Gly Ala Val
785                 790                 795                 800

Gly Thr Val Lys Glu Glu Pro Lys Asn Glu Pro Lys Asn Pro Val Ile
                805                 810                 815

Thr Pro Lys Val Asp Asn Val Lys Thr Ile Ala Thr Pro Asp Phe Asn
            820                 825                 830

Arg Asn Ala Asp Gly Lys Lys Asn Glu Ala Thr Asn Asn Asp Ala
            835                 840                 845

Lys Lys Glu Lys Asn Ser Lys Thr Ala Asp Thr Ala Gln Leu Gly Leu
        850                 855                 860

Tyr Met Val Leu Leu Leu Gly Ser Leu Ala Leu Leu Val Arg Lys Tyr
865                 870                 875                 880

Arg Ala Gly Arg Leu
                885

<210> SEQ ID NO 14
<211> LENGTH: 321
<212> TYPE: PRT
<213> ORGANISM: Bacillus anthracis

<400> SEQUENCE: 14
```

Met Asn Phe Met Arg Lys Lys Ser Phe Thr Val Phe Val Phe Ser Leu
1               5                   10                  15
Ala Phe Ser Leu Leu Leu Ser Ala Cys Gly Lys Ser Asn Thr Lys Glu
                20                  25                  30
Glu Ser Lys Glu Asp Thr Lys Lys Glu Met Ile Pro Val Glu His Ala
            35                  40                  45
Met Gly Lys Thr Glu Val Pro Ala Asn Pro Lys Arg Val Val Ile Leu
50                  55                  60
Thr Asn Glu Gly Thr Glu Ala Leu Leu Glu Leu Gly Val Lys Pro Val
65                  70                  75                  80
Gly Ala Val Lys Ser Trp Thr Gly Asp Pro Trp Tyr Pro His Ile Lys
                85                  90                  95
Asp Lys Met Lys Asp Val Lys Val Val Gly Asp Glu Gly Gln Val Asn
            100                 105                 110
Val Glu Thr Ile Ala Ser Leu Lys Pro Asp Leu Ile Ile Gly Asn Lys
            115                 120                 125
Met Arg His Glu Lys Val Tyr Glu Gln Leu Lys Ala Ile Ala Pro Thr
130                 135                 140
Val Phe Ser Glu Thr Leu Arg Gly Glu Trp Lys Asp Asn Phe Lys Phe
145                 150                 155                 160
Tyr Ala Lys Ala Leu Asn Lys Glu Lys Asp Gly Gln Lys Val Leu Ala
                165                 170                 175
Ala Tyr Asp Lys Arg Met Lys Asp Leu Lys Ala Lys Leu Gly Asp Lys
            180                 185                 190
Val Asn Gln Glu Ile Ser Met Val Arg Phe Met Pro Gly Asp Val Arg
            195                 200                 205
Ile Tyr His Gly Asp Thr Phe Ser Gly Val Ile Leu Lys Glu Leu Gly
210                 215                 220
Phe Lys Arg Pro Gly Asp Gln Asn Lys Asn Asp Phe Ala Glu Arg Asn
225                 230                 235                 240
Val Ser Lys Glu Arg Ile Ser Ala Met Asp Gly Asp Val Leu Phe Tyr
                245                 250                 255
Phe Thr Phe Asp Lys Gly Asn Glu Lys Lys Gly Ser Glu Leu Glu Lys
            260                 265                 270
Glu Tyr Ile Asn Asp Pro Leu Phe Lys Asn Leu Asn Ala Val Lys Asn
            275                 280                 285
Gly Lys Ala Tyr Lys Val Asp Asp Val Ile Trp Asn Thr Ala Gly Gly
            290                 295                 300
Val Met Ala Ala Asn Leu Leu Leu Asp Asp Ile Glu Lys Arg Phe Val
305                 310                 315                 320
Lys

<210> SEQ ID NO 15
<211> LENGTH: 314
<212> TYPE: PRT
<213> ORGANISM: Bacillus anthracis

<400> SEQUENCE: 15

Met Lys Arg Lys Leu Phe Ile Leu Phe Thr Ile Met Leu Val Val Leu
1               5                   10                  15
Ser Ile Val Gly Cys Ser Ser Gln Lys Glu Glu Ser Lys Ala Lys Glu
                20                  25                  30
Gln Pro Lys Thr Lys Val Val Lys His Ala Lys Gly Glu Ala Thr Ile
            35                  40                  45

-continued

Pro Val Asn Pro Lys Arg Ile Val Asp Leu Ser Gly Ser Thr Glu Glu
            50                  55                  60

Leu Leu Leu Leu Gly His Lys Pro Val Gly Thr Ala Asn Thr Tyr Lys
 65                  70                  75                  80

Asp Lys Ile Gln Lys His Leu Thr Glu Lys Leu Asp Gly Val Lys Ala
                85                  90                  95

Val Gly Trp Tyr Trp Ala Pro Lys Val Asp Leu Glu Ala Val Thr Ala
            100                 105                 110

Leu Lys Pro Asp Leu Ile Ile Leu Asn Asn Arg Gln Leu Lys Ile Tyr
        115                 120                 125

Asp Gln Leu Glu Lys Val Ala Pro Thr Val Val Leu Glu Thr Asn Leu
130                 135                 140

Glu Asp Trp Arg Gly Lys Phe Lys Glu Val Gly Lys Leu Phe Asp Glu
145                 150                 155                 160

Glu Lys Lys Ala Asp Lys Trp Ile Ala Asp Tyr Asp Lys Lys Ala Asp
                165                 170                 175

Ser Leu Ser Lys Lys Ile Lys Glu Lys Thr Lys Asp Asp Ser Phe Met
            180                 185                 190

Phe Val Ala Val Thr Pro Gln Asn Phe Arg Val Tyr Gly Ser Phe Gly
        195                 200                 205

Tyr Gly Asp Ile Ile Phe Asn Asp Leu Lys Leu Pro Ala Thr Lys Gly
210                 215                 220

Thr Asp Leu Lys Gln Thr Met Ala Gln Val Ser Leu Glu Gly Leu Val
225                 230                 235                 240

Ala Phe Gln Pro Asp Gln Met Phe Ile Val Asn Phe Gly Gly Glu Ala
                245                 250                 255

Asp Lys Val Tyr Glu Asp Tyr Lys Asn Ser Ala Val Trp Lys Asp Asn
            260                 265                 270

Lys Ala Val Lys Asn Asn His Val Tyr Glu Val Ser Asn Glu Val Phe
        275                 280                 285

Asn Thr Lys Ala Phe Asn Pro Ile Gly Lys Asp Met Leu Ile Asp Glu
        290                 295                 300

Ile Ala Lys Glu Ile Leu Ala Lys Asn Lys
305                 310

<210> SEQ ID NO 16
<211> LENGTH: 311
<212> TYPE: PRT
<213> ORGANISM: Bacillus anthracis

<400> SEQUENCE: 16

Met Lys Phe Lys Asn Val Val Leu Ser Ile Leu Cys Ile Phe Val Phe
1               5                   10                  15

Ala Leu Thr Ala Cys Ser Ser Asn Thr Asn Gly Lys Glu Glu Gly Ser
            20                  25                  30

Gly Lys Leu Lys Val Val Thr Thr Tyr Ser Ile Ile Tyr Asp Met Val
        35                  40                  45

Lys Gln Ile Gly Gly Glu Lys Val Glu Ile His Ser Leu Val Pro Ile
    50                  55                  60

Gly Ala Asn Pro His Glu Tyr Asp Pro Leu Pro Lys Val Met Lys
65                  70                  75                  80

Met Thr Asp Ala Asp Met Val Leu Tyr Asn Gly Leu Asn Leu Glu Glu
                85                  90                  95

Gly Gly Ala Trp Phe Lys Lys Leu Leu Lys Thr Ala Asn Lys Ser Glu
            100                 105                 110

-continued

Lys Asp Ala Pro Val Tyr Lys Val Ser Glu Gly Val Glu Ala Ile Tyr
            115                 120                 125
Leu Glu Thr Lys Gly Leu Glu Lys Glu Pro Asp Pro His Ala Trp Met
        130                 135                 140
Asn Ile Lys Asn Gly Ile Leu Tyr Ala Glu Asn Val Lys Lys Ala Leu
145                 150                 155                 160
Ile Lys Glu Asp Pro Lys Asn Lys Glu Phe Tyr Thr Lys Asn Ala Asp
                165                 170                 175
Asn Tyr Val Ala Glu Leu Gln Lys Leu His Asp Glu Thr Val Asn Arg
            180                 185                 190
Ile His Gln Ile Pro Glu Glu Lys Arg Phe Leu Ile Ser Ser Glu Gly
        195                 200                 205
Ala Phe Lys Tyr Phe Gly Lys Ala Tyr Asp Ile Lys Thr Gly Tyr Ile
    210                 215                 220
Trp Glu Ile Asn Ser Glu Asn Gln Gly Thr Pro Asp Gln Ile Arg Asp
225                 230                 235                 240
Val Val Ser Val Ile Gln Thr Asn Lys Val Pro Ala Leu Phe Val Glu
                245                 250                 255
Thr Ser Val Asp Arg Arg Ser Met Glu Thr Val Ser Lys Glu Thr Asn
            260                 265                 270
Val Pro Ile Ala Gly Thr Ile Phe Thr Asp Ser Leu Gly Lys Ser Gly
        275                 280                 285
Glu Asp Gly Asp Thr Tyr Leu Lys Met Met Lys Trp Asn Ile Asp Thr
    290                 295                 300
Ile Ile Asn Gly Leu Gln Lys
305                 310

<210> SEQ ID NO 17
<211> LENGTH: 31
<212> TYPE: DNA
<213> ORGANISM: artificial
<220> FEATURE:
<223> OTHER INFORMATION: primer

<400> SEQUENCE: 17
gactaggcct gattcaggta agaaacttc g                                    31

<210> SEQ ID NO 18
<211> LENGTH: 31
<212> TYPE: DNA
<213> ORGANISM: artificial
<220> FEATURE:
<223> OTHER INFORMATION: primer

<400> SEQUENCE: 18
gactaagctt ctacttagct aaagttttg c                                    31

<210> SEQ ID NO 19
<211> LENGTH: 29
<212> TYPE: DNA
<213> ORGANISM: artificial
<220> FEATURE:
<223> OTHER INFORMATION: primer

<400> SEQUENCE: 19
gactaggcct aaggatgcga agactgaag                                      29

<210> SEQ ID NO 20
<211> LENGTH: 31

-continued

<212> TYPE: DNA
<213> ORGANISM: artificial
<220> FEATURE:
<223> OTHER INFORMATION: primer

<400> SEQUENCE: 20
gactgtcgac ttatttccct aaaacgaact c                               31

<210> SEQ ID NO 21
<211> LENGTH: 29
<212> TYPE: DNA
<213> ORGANISM: artificial
<220> FEATURE:
<223> OTHER INFORMATION: primer

<400> SEQUENCE: 21
gactaggcct tctacagaca aaaagaacg                                  29

<210> SEQ ID NO 22
<211> LENGTH: 32
<212> TYPE: DNA
<213> ORGANISM: artificial
<220> FEATURE:
<223> OTHER INFORMATION: primer

<400> SEQUENCE: 22
gactaagctt ttatttacca agaaagctct tc                              32

<210> SEQ ID NO 23
<211> LENGTH: 30
<212> TYPE: DNA
<213> ORGANISM: artificial
<220> FEATURE:
<223> OTHER INFORMATION: primer

<400> SEQUENCE: 23
gactaggcct gacgaaaaag catcggcaac                                 30

<210> SEQ ID NO 24
<211> LENGTH: 33
<212> TYPE: DNA
<213> ORGANISM: artificial
<220> FEATURE:
<223> OTHER INFORMATION: primer

<400> SEQUENCE: 24
gactaagctt tcatttcctt acatcttgta tac                             33

<210> SEQ ID NO 25
<211> LENGTH: 33
<212> TYPE: DNA
<213> ORGANISM: artificial
<220> FEATURE:
<223> OTHER INFORMATION: primer

<400> SEQUENCE: 25
gactaggcct gacaataaaa atcaagctat aac                             33

<210> SEQ ID NO 26
<211> LENGTH: 31
<212> TYPE: DNA
<213> ORGANISM: artificial
<220> FEATURE:
<223> OTHER INFORMATION: primer

<400> SEQUENCE: 26

```
gactaagctt tcacttcttc gctgtcatta c                                          31

<210> SEQ ID NO 27
<211> LENGTH: 32
<212> TYPE: DNA
<213> ORGANISM: artificial
<220> FEATURE:
<223> OTHER INFORMATION: primer

<400> SEQUENCE: 27
cgcagggatc cgttgaaatg aaagcagcta gc                                         32

<210> SEQ ID NO 28
<211> LENGTH: 30
<212> TYPE: DNA
<213> ORGANISM: artificial
<220> FEATURE:
<223> OTHER INFORMATION: primer

<400> SEQUENCE: 28
cgcagaagct tctatttcat ttctttcttc                                            30

<210> SEQ ID NO 29
<211> LENGTH: 30
<212> TYPE: DNA
<213> ORGANISM: artificial
<220> FEATURE:
<223> OTHER INFORMATION: primer

<400> SEQUENCE: 29
gactaggcct gctacaaaac tagctgatgg                                            30

<210> SEQ ID NO 30
<211> LENGTH: 31
<212> TYPE: DNA
<213> ORGANISM: artificial
<220> FEATURE:
<223> OTHER INFORMATION: primer

<400> SEQUENCE: 30
gactaagctt ttatttaata ctgttcccat c                                          31
```